US007763426B2

(12) United States Patent
Haake et al.

(10) Patent No.: US 7,763,426 B2
(45) Date of Patent: Jul. 27, 2010

(54) PROBES AND METHODS FOR DETECTION OF *ESCHERIDIA COLI* AND ANTIBIOTIC RESISTANCE

(75) Inventors: David A. Haake, Culver City, CA (US); Bernard M. Churchill, Pacific Palisades, CA (US); Joseph C. Liao, Los Altos, CA (US); Marc A. Suchard, Los Angeles, CA (US); Yang Li, Northridge, CA (US); Mitra Mastali, Marina Del Rey, CA (US)

(73) Assignees: The Regents of the University of California, Oakland, CA (US); The United States of America as represented by the Department of Veterans Affairs, Washington, DC (US)

( * ) Notice: Subject to any disclaimer, the term of this patent is extended or adjusted under 35 U.S.C. 154(b) by 349 days.

(21) Appl. No.: 11/743,071

(22) Filed: May 1, 2007

(65) Prior Publication Data
US 2008/0199863 A1 Aug. 21, 2008

Related U.S. Application Data

(63) Continuation-in-part of application No. PCT/US2005/039292, filed on Nov. 1, 2005.

(60) Provisional application No. 60/865,780, filed on Nov. 14, 2006, provisional application No. 60/623,903, filed on Nov. 1, 2004.

(51) Int. Cl.
*C12Q 1/68* (2006.01)
*C07H 21/02* (2006.01)
*C07H 21/04* (2006.01)

(52) U.S. Cl. ........................ 435/6; 536/23.1; 536/24.32; 536/24.33

(58) Field of Classification Search ........................ None
See application file for complete search history.

(56) References Cited

U.S. PATENT DOCUMENTS

| 6,348,314 | B1 | 2/2002 | Prudent et al. | |
|---|---|---|---|---|
| 6,391,558 | B1 | 5/2002 | Henkens et al. | |
| 6,582,908 | B2 * | 6/2003 | Fodor et al. | 506/9 |
| 2002/0123048 | A1 | 9/2002 | Gau | |

OTHER PUBLICATIONS

Liao et al. Journal of Molecular Diagnostics. Apr. 1, 2007. 9: 158-168.*
Elsholz, B. "Automated detection and quantitation of bacterial RNA by using electrical microarrays", Anal. Chem, Jul. 15, 2006, 78, 4794-4802.
Fuchs, B.M., "Flow cytometric analysis of the in situ accessibility of . . . probes", Applied & Environmental Microbiology, Dec. 1998, V64, No. 12, 4973-4982.
Gau, J., "A MEMS based amperometric detector for *E. coli* bacteria using self-assembled monolayers", Biosensors & Bioelectronics, 2001, V16, 745-755.

* cited by examiner

*Primary Examiner*—Carla Myers
(74) *Attorney, Agent, or Firm*—Karen S. Canady; canady + lortz LLP

(57) ABSTRACT

Described are probes and methods for detecting pathogens and antibiotic resistance of a specimen. The method comprises contacting the specimen with a growth medium; and lysing the specimen to release nucleic acid molecules from the specimen. The lysate of the specimen is contacted with a capture probe immobilized on a substrate, wherein the capture probe comprises an oligonucleotide that specifically hybridizes with a first target nucleic acid sequence region of ribosomal RNA. The lysate is in contact with a detector probe that comprises a detectably labeled oligonucleotide that specifically hybridizes with a second target nucleic acid sequence region of ribosomal RNA. The presence or absence of labeled oligonucleotide complexed with the substrate is determined. Detection of labeled oligonucleotide complexed with the substrate is indicative of the presence of pathogen. Performing the method in the presence and absence of an antibiotic permits detection of antibiotic resistance.

26 Claims, 13 Drawing Sheets

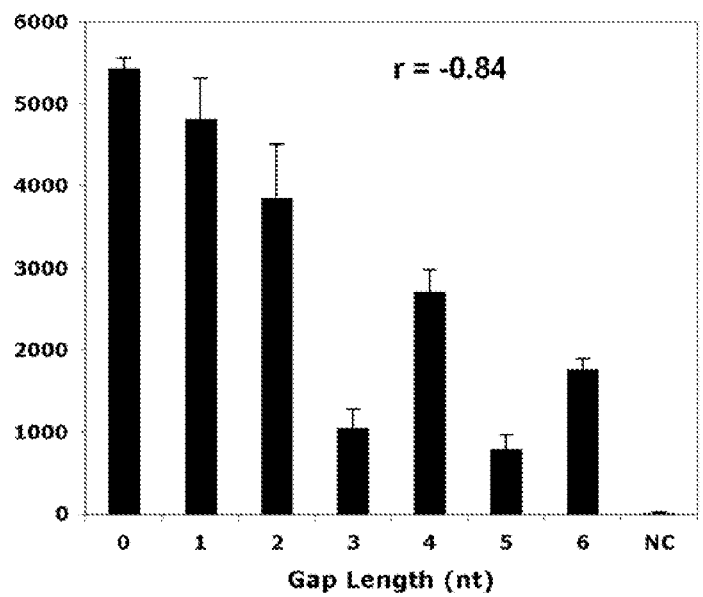
FIG. 10
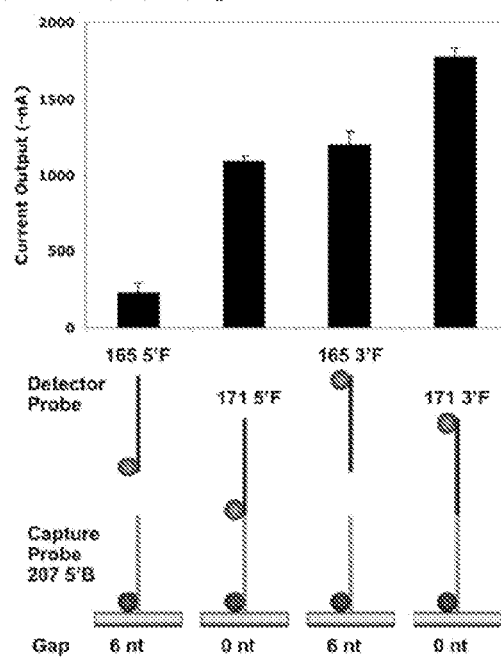 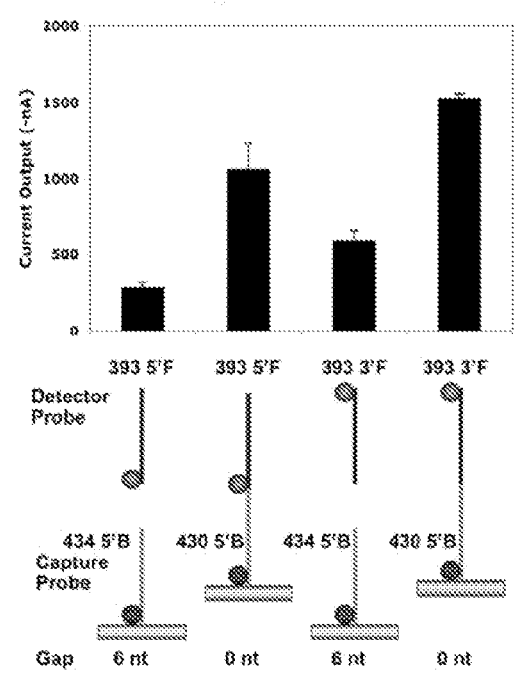
FIG. 11

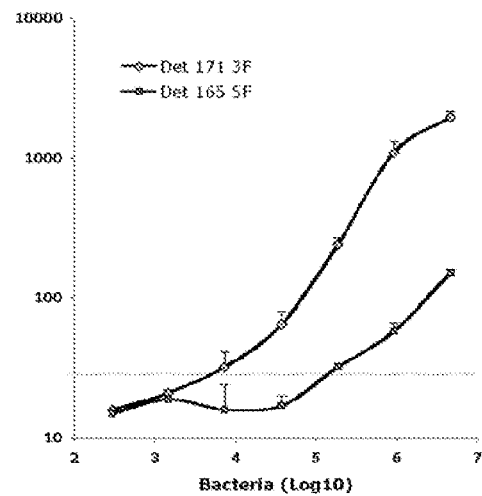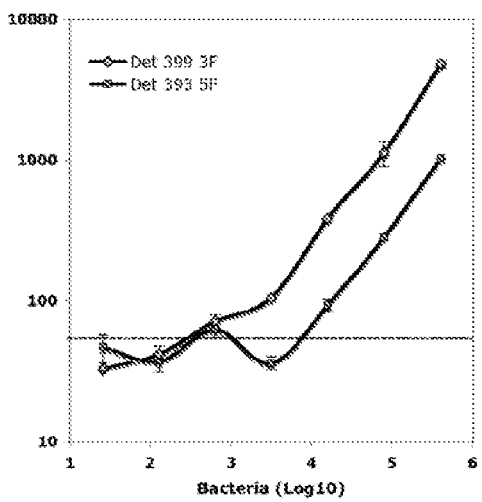
FIG. 12
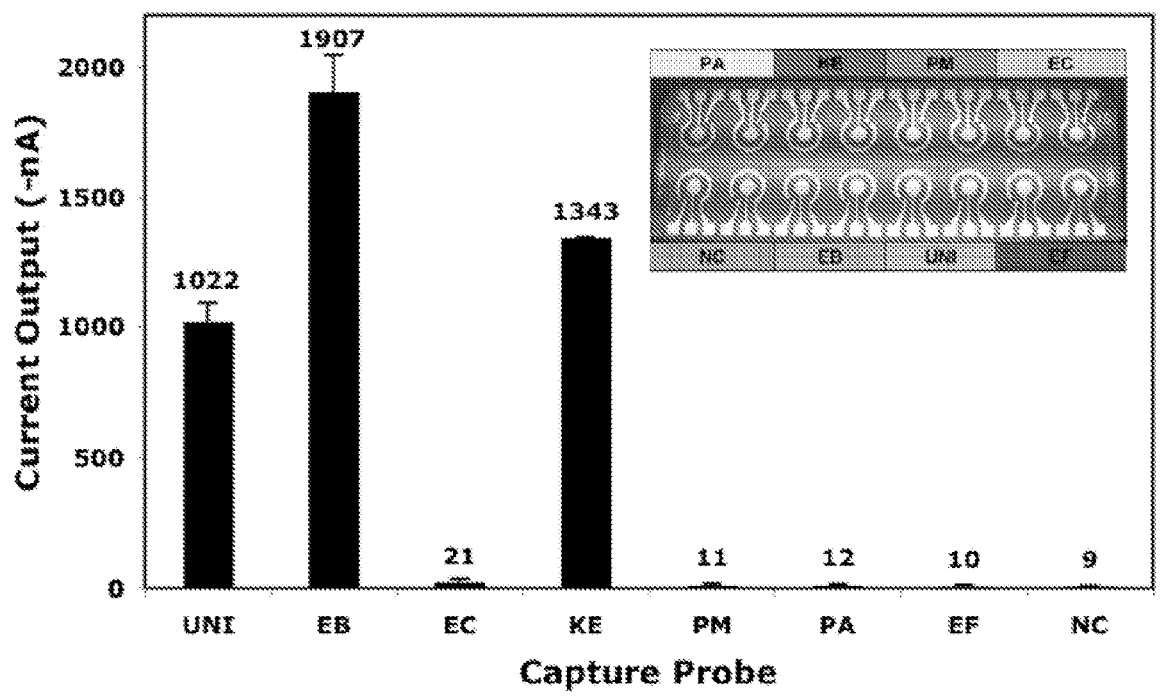
FIG. 13

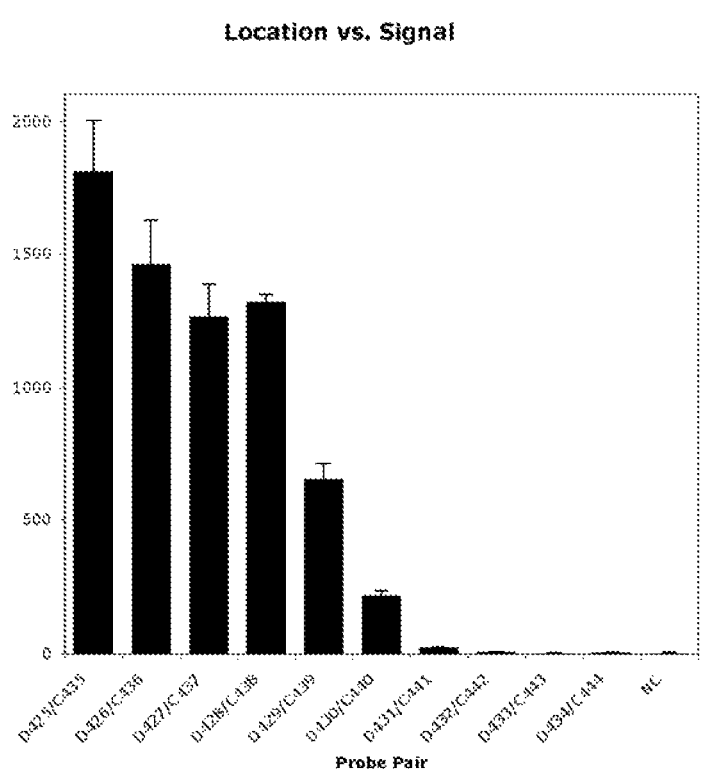
FIG. 16A    FIG. 16B
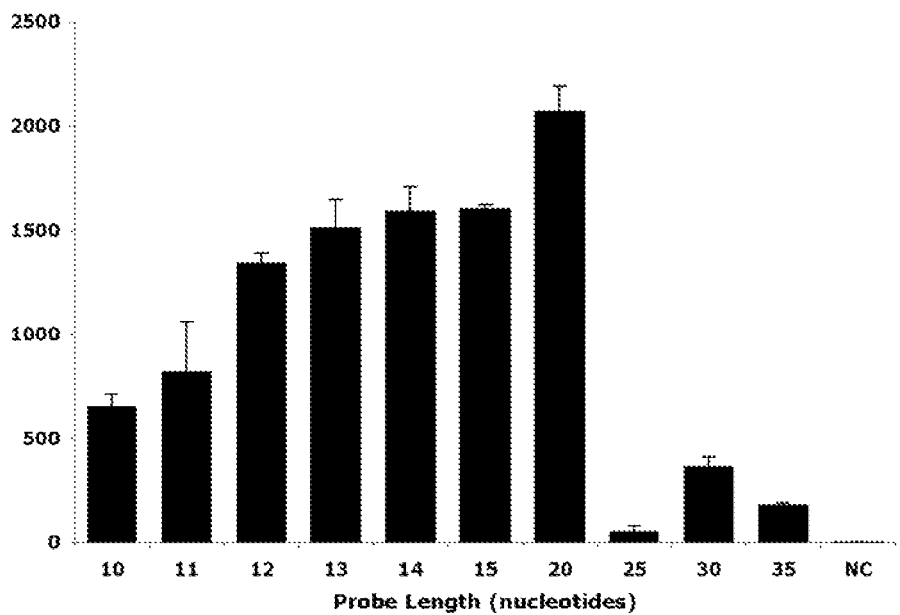
FIG. 17

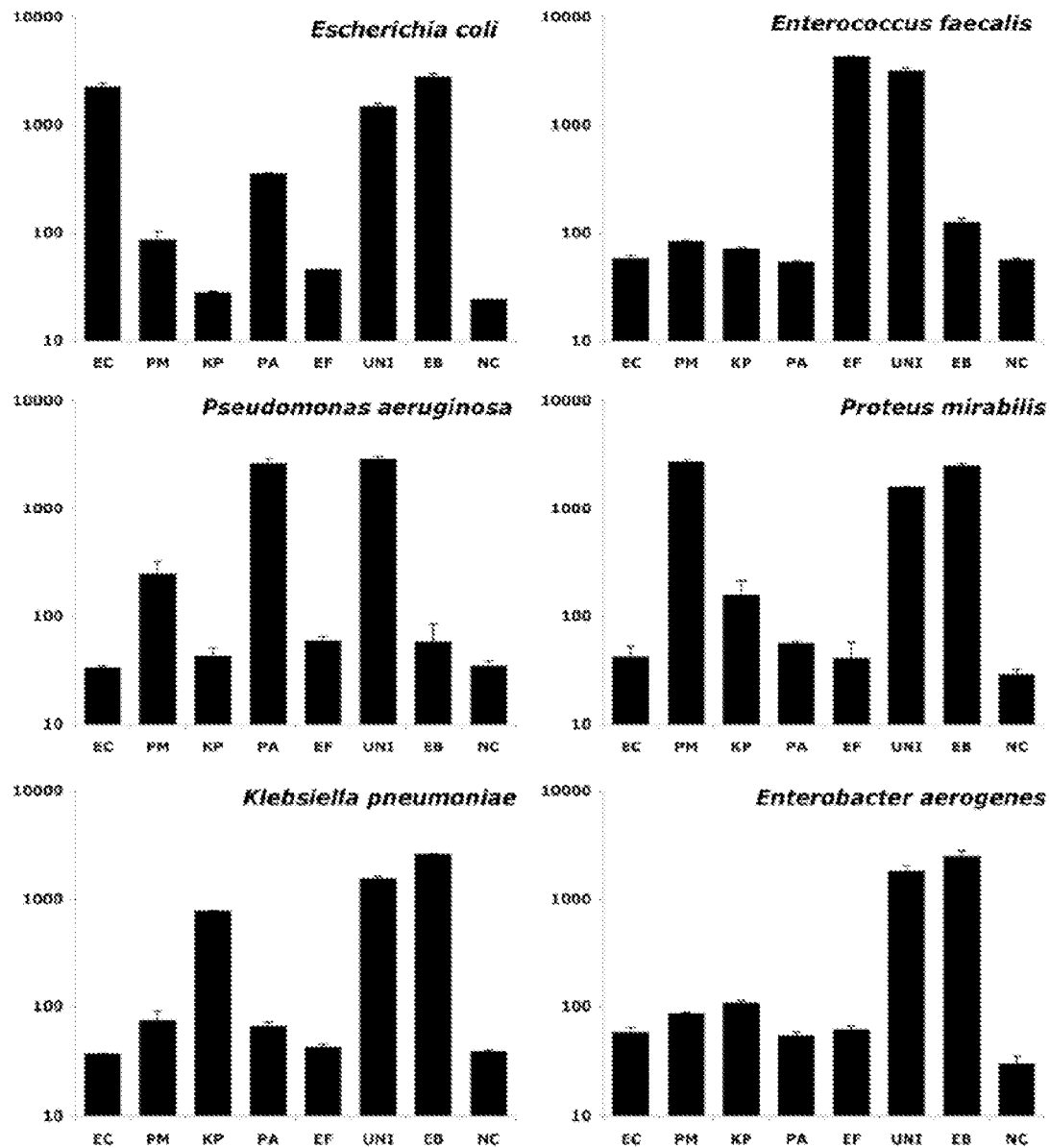
FIG. 21A-F

PROBES AND METHODS FOR DETECTION OF *ESCHERIDIA COLI* AND ANTIBIOTIC RESISTANCE

This application claims the benefit of U.S. provisional patent application No. 60/865,780, filed Nov. 14, 2006, and is a continuation-in-part of PCT application number US2005/39292, filed Nov. 1, 2005, which claims the benefit of U.S. provisional patent application No. 60/623,903, filed Nov. 1, 2004, the entire contents of which are incorporated herein by reference. Throughout this application various publications are referenced. Some of these references are indicated with numerals that refer to the list of references that can be found at the end of Example 1. Additional references noted in the other examples can be found in the list of literature cited at the end of the corresponding example. The disclosures of these publications in their entireties are hereby incorporated by reference into this application in order to describe more fully the state of the art to which this invention pertains.

This invention was made with Government support via Grant No. EB00127, awarded by the National Institutes of Health (NIH). The United States Government has certain rights in this invention.

TECHNICAL FIELD OF THE INVENTION

The present invention relates generally to materials and methods for rapid detection of pathogens, and of antimicrobial susceptibility using bacterial 16S rRNA, and suitable for use with an electrochemical sensor.

BACKGROUND OF THE INVENTION

Urinary tract infection (UTI) is the most common urological disease in the United States and the second most common bacterial infection of any organ system, UTIs are a major cause of patient morbidity and health-care expenditure for all age groups. UTIs account for approximately 7 million office visits, more than 1 million visits to emergency departments, and approximately 100,000 hospitalizations each year. The estimated annual cost to the United States health-care system is approximately $1.6 billion. In patients who are at risk for complicated UTIs (e.g. obstructive uropathy, immunocompromised state, neurogenic bladder, congenital urinary tract anomalies, and indwelling foreign bodies), delay in diagnosis and initiation of appropriate medical intervention can lead to life threatening systemic infections or permanently reduced renal function.

The traditional basis for the identification of urinary pathogens (uropathogens) is urine culture. The major drawback of the urine culture is the time lapse of approximately 1-2 days between specimen collection and pathogen identification. In the absence of expeditious laboratory diagnosis, clinicians frequently need to decide whether to initiate empiric outpatient or inpatient antimicrobial treatment without supportive laboratory evidence. Injudicious use of antimicrobial agents contributes to the incidence of adverse drug reactions and the emergence of antibiotic resistant pathogens. Urine specimens are the most common type of body fluid submitted for culture to clinical microbiology laboratories. Significant resources at these clinical laboratories are devoted to the time-consuming processing of urine specimens, although the majority of these specimens are negative or yield insignificant quantities of bacteria. A rapid test that could identify the uropathogens, or confirm the presence or absence of clinically significant bacteria with high sensitivity and specificity, would significantly reduce the workload of clinical microbiology laboratories. In addition a test that determined the susceptibility of a given specimen to antibiotic treatment would avoid the health risks associated with administering antibiotics to a patient with an antibiotic-resistant infection.

Molecular biological techniques based on DNA hybridization are increasingly utilized in clinical diagnostic testing, and are especially useful in the identification of infectious agents that cannot be cultured. Hybridization of oligonucleotides to the unique molecular sequence of an organism's DNA or RNA is highly sensitive for pathogen-specific identification, surpassing culturing methods that depend on morphological and biochemical characteristics. More rapid real-time polymerase chain reaction (PCR) quantification involving amplification of target DNA or RNA currently requires technically demanding specimen processing procedures. Despite the inherent advantages of molecular diagnostic approaches, this issue has thus far precluded widespread application of molecular techniques in clinical diagnostics.

Recent advances in sensors and actuators based on microfabrication and bionanotechnology have led to an intense interest in their development for biomedical applications. Microscale devices are particularly compatible to detect and manipulate biological molecules of interest, such as nucleic acids and proteins, with nanoscale precision. As an example of micro-devices well-suited for clinical diagnostic testing, electrochemical sensors offer sensitivity, selectivity, portability and relative low cost for nucleic acids detection. The basic electrochemical sensor design is comprised of a nucleic acid layer coupled with electrochemical transducers to detect sequence-specific hybridization events.

There remains a need for improved tools to permit the rapid detection of pathogens, and to permit assessment of the susceptibility of bacterial pathogens to antimicrobial treatment. In particular, there is a need for probes capable of detecting and distinguishing the various bacterial pathogens, as well as more rapid methods to obtain assay results needed to guide effective treatment.

SUMMARY OF THE INVENTION

The invention disclosed herein addresses these needs and others by providing methods and materials for rapid, species-specific detection of pathogens, as well as methods and materials for rapid detection of antimicrobial susceptibility. The invention provides oligonucleotide probes that can be used separately or in combination for the detection and distinction of bacterial pathogens commonly found in urological and other patient specimens. In addition, the invention provides methods for using such probes to rapidly assay for pathogens. The invention provides a universal lysis buffer that enables lysis of both gram-negative and gram-positive bacteria, and permits immediate assay of lysed specimens (e.g., urine) without requiring a bacterial purification step, further accelerating the assay. In addition, the universal assay can be used to detect susceptibility to antimicrobial treatment.

The invention provides a method for detecting the presence of a pathogen in a specimen. In one embodiment, the method comprises contacting a lysate of the specimen with a capture probe immobilized on a substrate. The capture probe comprises a first oligonucleotide that specifically hybridizes with a first target nucleic acid sequence region of the pathogen to be detected. Typically, the first target nucleic acid sequence is selected from the group consisting of SEQ ID NOS: 22, 24, 26, 28, 30, 32, 34, 36, 38, 40 and 42. The contacting occurs under conditions that permit hybridization of the capture probe with the first target nucleic acid sequence.

The lysate has been brought into contact with a detector probe that comprises a detectably labeled oligonucleotide that specifically hybridizes with a second target nucleic acid sequence region of the pathogen. Typically, the second target nucleic acid sequence is selected from the group consisting of SEQ ID NOS: 23, 25, 27, 29, 31, 33, 35, 37, 39, 41 and 43. The lysate can be brought into contact with the detector probe simultaneous with, prior to or subsequent to, the contacting of the lysate with the capture probe.

The method further comprises determining the presence of the detector probe. Detection of the second detectable label, or detection of the detector probe complexed with the substrate is indicative of the presence of the corresponding pathogen.

Typically, the conditions that permit hybridization are a temperature of less than 39° C. and a saline solution, such as a phosphate buffered saline (PBS). Typically, the PBS is 1M PBS. The method can be performed at ambient temperature, e.g., room temperature or 20° C., or at body temperature, such as 37° C. In one embodiment, the method is performed at 20-25° C.

The invention additionally provides a method for detecting antibiotic resistance of a specimen. The method comprises contacting the specimen with an antibiotic and a growth medium; lysing the specimen to produce a lysate of the specimen, wherein the lysing releases nucleic acid molecules from the specimen; and contacting the lysate of the specimen with a capture probe immobilized on a substrate, wherein the capture probe comprises an oligonucleotide that specifically hybridizes with a first target nucleic acid sequence region of 16S ribosomal RNA, wherein the lysate is in contact with a detector probe that comprises a detectably labeled oligonucleotide that specifically hybridizes with a second target nucleic acid sequence region of 16S ribosomal RNA. The method further comprises determining the presence or absence of labeled oligonucleotide complexed with the substrate, whereby detection of the labeled oligonucleotide complexed with the substrate is indicative of resistance to the antibiotic. Likewise, the method can be used to detect susceptibility to antibiotic treatment.

Typically, the method for detecting antibiotic resistance or susceptibility is performed after first identifying and quantifying the pathogen of interest. The method of detecting the presence of a pathogen set forth above can be used to identify the pathogen. Identification of the pathogen guides the selection of antibiotic to be tested for resistance. Quantitation of the pathogen guides the selection of an appropriate ratio of antibiotic to pathogen for subsequent testing. The method is then carried out by inoculation of the pathogen-containing specimen into a growth medium. This inoculation is preferably done in both the presence and absence of antibiotic. The presence or amount of pathogen is then determined, typically by comparing the specimens inoculated in the presence and in the absence of antibiotic. A reduced or lesser pathogen amount in the presence of antibiotic is indicative of susceptibility to the antibiotic.

In one embodiment, the first and second nucleic acid sequences of the pathogen are adjacent to each other, such that no gap remains between the capture probe and the detector probe upon hybridization with the target nucleic acid sequences of the pathogen. In another embodiment, a gap between the first and second nucleic acid sequences is not greater than about 6 base pairs.

The lysate can be prepared by contacting the specimen with a universal lysis buffer capable of lysing both gram-negative and gram-positive bacteria. A representative universal lysis buffer contains Triton X-100, $KH_2PO_4$, EDTA and lysozyme. Alternatively, the lysate can be prepared by contacting the specimen with a first lysis buffer comprising a non-denaturing detergent (e.g., Triton X-100) and lysozyme, or a second lysis buffer comprising NaOH. In another embodiment, the lysing comprises contacting the specimen with both buffers in series, e.g. with the second lysis buffer, either before or after contacting the specimen with the first lysis buffer. The contacting of the specimen with the buffer(s) typically occurs at room temperature. Typically, the specimen is in contact with the lysis buffer for a total of about 10 minutes. Where a first and second lysis buffer is used, the contact with each buffer is typically about 5 minutes. Those skilled in the art are aware that the time and temperature under which the contact with lysis buffer occurs can be varied (e.g. higher temperatures will accelerate the lysis) and also optimized for a particular specimen, target pathogen and other assay conditions.

The oligonucleotide probes are typically less than 60 bases in length, preferably 10-50 bases in length, and in most embodiments, the oligonucleotide probes are 10-35 bases in length. In one embodiment, the probe is about 15-25 bases in length. Capture and detector probes of the invention are typically selected that specifically hybridize under highly stringent conditions to a target capture region and a target detector region, respectively, of bacterial ribosomal RNA (rRNA), wherein the target capture region and target detector region are, or are fully complementary to and of the same length as nucleic acid molecules corresponding to, a pair of sequences selected from the group of paired sequences shown in Table 12 in the Examples below. Representative capture probes have a sequence selected from those shown in SEQ ID NOS: 44, 46, 48, 50, 52, 54, 56, 58, 60, 62 and 64. Representative detector probes have a sequence selected from those shown in SEQ ID NOS: 45, 47, 49, 51, 53, 55, 57, 59, 61, 63 and 65. The bacterial ribosomal RNA can be 5S, 16S or 23S rRNA. Typically, the rRNA is 16S rRNA.

The detectable labels for use with the invention can be selected from many such labels known in the art. In one embodiment, the label comprises a reporter enzyme, such as horseradish peroxidase (HRP). In another embodiment, the HRP is conjugated to an antibody or other binding partner and serves as a secondary label that binds to a primary label on the detector probe. In one example, the primary label on the detector probe is fluorescein and the secondary label is HRP conjugated to an anti-fluorescein antibody. The detectable label can be at the 3' and/or 5' end of the detector probe. In some embodiments, the detectable label is at the 3' end of the detector probe.

The pathogen is typically a microorganism that can be found in bodily fluids. In one embodiment, the pathogen is a uropathogen. Uropathogens include bacterial and fungal pathogens. In one embodiment, the pathogen is a bacterial pathogen, such as *Escherichia coli, Proteus mirablilis, Pseudomonas aeruginosa, Enterococcus* spp., *Klebsiella pneumonae, Enterobacter aerogenes, Enterobacter clocae.*

The specimen can be any specimen believed to contain or suspected of containing a pathogen, such as a bodily fluid. Representative bodily fluids include blood and blood products, saliva, sputum, semen, prostatic secretions, cerebrospinal fluids and urine. Typically, for the detection of uropathogens, the specimen is urine.

The invention additionally provides an assay kit for use in carrying out the method of the invention. The kit comprises one or more of the probes described herein, and, optionally, a container or substrate therefor. In one embodiment, the kit comprises a substrate to which one or more capture probes of the invention are bound or otherwise immobilized. Optionally, the kit further comprises a container and one or more detector probes corresponding to the capture probes. In one embodiment, the substrate is an electrochemical sensor array.

BRIEF DESCRIPTION OF THE FIGURES

FIG. 10. Electrochemical signal intensity as a function of the distance (in nucleotides) between the capture and detector probe hybridization sites on the 16S rRNA target, Current output (in nanoAmperes) was measured using capture probe EC434C and various 3'-fluorescein modified detector probes hybridized to 16S rRNA released from $4.2 \times 10^7$ *E. coli*. Mean and standard deviation of experiments performed in duplicate are shown. Background signal was determined in negative control (NC) experiments performed with capture and detector probes but without bacterial lysate. There was a negative correlation (r=−0.84) between signal intensity and size of the gap between the capture and detector probe hybridization sites. The signal intensity obtained using capture and detector probes hybridizing to adjacent (0 nt gap) sites produced an electrochemical signal significantly (>0.31 log units) greater than that obtained using detector probes hybridizing ≧3 nt away from the capture probe hybridization site.

FIG. 11. Electrochemical signal intensity as a function of location of probe hybridization and fluorescein modification. In Panel A, signal intensity was measured using the *Enterococcus*-specific capture probe EF C207 paired with 3'- or 5'-fluorescein modified detector probes hybridizing to the enterococcal 16S target at a site adjacent to (EF D171) or 6 nt removed from (EF D165 the capture probe. In Panel B, signal intensity was measured using 3'- or 5'-fluorescein modified detector probe EC393 D paired with the *E. coli*-specific capture probes hybridizing to the *E. coli* 16S target at a site adjacent to (EC430C) or 6 nt removed from (EC434C) the detector probe. The configurations of the capture and detector probes are shown schematically. Mean and standard deviation of experiments performed in duplicate are shown.

FIG. 12. Sensitivity of the electrochemical sensor assay as a function of locations of probe hybridization and fluorescein modification. Panel A shows electrochemical sensor results from five-fold serial dilutions of enterococcal cells using capture probe EF207C paired with detector probes EF165D or EF171D modified by fluorescein at the 5'- and 3'-positions, respectively. Panel B shows electrochemical sensor results from five-fold serial dilutions of *E. coli* cells using capture probe EC434C paired with detector probes EC393C or EC399C modified by fluorescein at the 5'- and 3'-positions, respectively. The current output thresholds for results significantly (>0.31 log units) greater than background are indicated by dashed horizontal lines, 3'-fluorescein modification of the detector probe combined with continuity between the detector and capture probe hybridization sites resulted in a 24-25 fold improvement in sensitivity of electrochemical sensor assay for detection of enterococci (from 232,000 down to 9,400 cells) and *E. coli* (from 6,200 down to 260 cells).

FIG. 13. Representative results testing the specificity of capture probes using the electrochemical sensor array. Lysate of *Klebsiella pneumonia* strain 13883 containing 16S rRNA was combined with a mixture of seven detector probes and applied to the surface of 16 sensor array (inset) functionalized with seven different capture probes. Negative control (NC) sensors to which no cell lysates were applied were used to measure background signal intensity. Mean and standard deviation of signal intensity from duplicate sensors is shown. Sensors functionalized with the universal bacterial probe (UNI), the Enterobacteriaceae group probe (EB), and the *Klebsiella* & *Enterobacter* group probe (KE) produced current output that was significantly greater (>0.31 log units) than background.

FIG. 16A. Electrochemical signal intensity as a function of probe hybridization location, Current output (in nanoamperes) was measured using a series of *E. coli*-specific 10mer capture and detector probes hybridized to 16S rRNA released from $9.1 \times 10^6$ *E. coli*. Numbers on the horizontal axis refer to the position of the first nucleotide of the detector (D) and capture (C) probe hybridization locations. Mean and SD of experiments performed in duplicate are shown. Background signal was determined in negative control (NC) experiments performed with capture and detector probes but without bacterial lysate.

FIG. 16B. Structure of *E. coli* 16S rRNA helix 18 (SEQ ID NO: 168). Signal intensity is dependent on the first nucleotide of the capture probe hybridization site being located in the bulge between positions 432 and 439.

FIG. 17. Electrochemical signal intensity as a function of probe length. Current output (in nanoamperes) was measured using a series of capture and detector probes of increasing length hybridized to 16S rRNA released from $9.1 \times 10^6$ *E. coli*. In each experiment, the capture and detector probes were of equal length, with the junction between the capture and detector probe hybridization sites between nucleotides 438 and 439. Mean and SD of experiments performed in duplicate are shown, Background signal was determined in negative control (NC) experiments performed with capture and detector probes but without bacterial lysate.

In FIG. 18A, a detector probe 13 nucleotides in length was used in combination with capture probes of varying length. In FIG. 18B, a capture probe 13 nucleotides in length was used in combination with detector probes of varying length. In both sets of experiments, the junction between the capture and detector probe hybridization sites was located between nucleotides 438 and 439. Mean and SD of experiments performed in duplicate are shown. Background signal was determined in negative control (NC) experiments performed with capture and detector probes but without bacterial lysate.

FIG. 21A-F. Results testing the specificity of the electrochemical sensor array. Lysates of six ATCC strains were combined with a mixture of seven detector probes and applied to the surface of the 16 sensor array functionalized with seven different capture probes. Negative control (NC) sensors to which no cell lysates were applied were used to measure background signal intensity. Mean and SD of log signal intensity from duplicate sensors are plotted on the vertical axes in antilog (nanoamperes) scale.

DETAILED DESCRIPTION OF THE INVENTION

Figure 1:
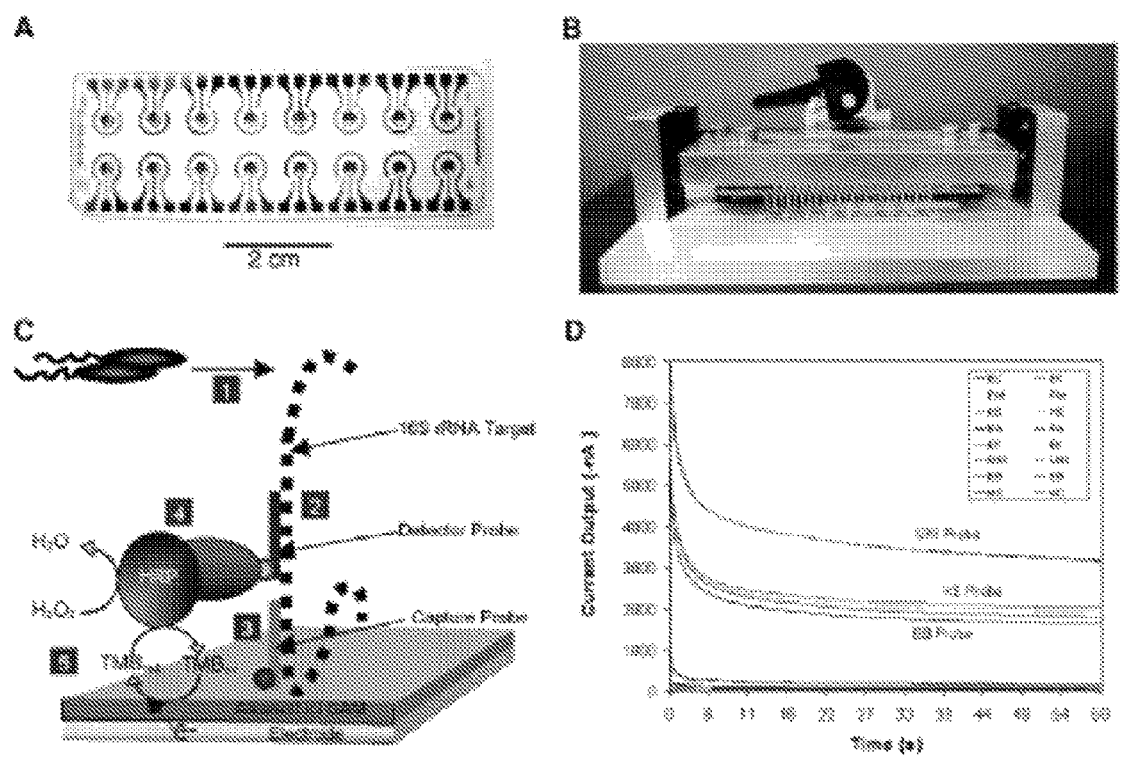
FIG. 1A-1D. Components and performance of the electrochemical sensor. (A) The 16-sensor array (2.5×7.5 cm) was microfabricated with a thin, optical-grade layer of gold electrodes deposited on plastic (GeneFluidics Inc., Monterey Park, Calif.). Each sensor in the array contained three electrodes: a central working electrode, a circumferential reference electrode, and a short auxiliary electrode. (B) The chip mounter with contact pins for simultaneous so reading of the current output from each of the sensors in the array. (C) Detection strategy: 1. Bacterial lysis to release 16s rRNA target (dashed line); 2. Hybridization of the target with the fluorescein-labeled detector probe: 3. Hybridization of the target with the biotin-labeled capture probe; 4. Binding of anti-fluorescein antibody conjugated with horseradish peroxidase (HRP) to the target-probe sandwich; and 5. Generation of current by transfer of electrons to the electron transfer mediator, TMB. (D) Current output in an experiment involving a clinical urine specimen containing *K. pneumoniae* showing signal stabilization from all 16 sensors in the array within 60 seconds.
Figure 2:
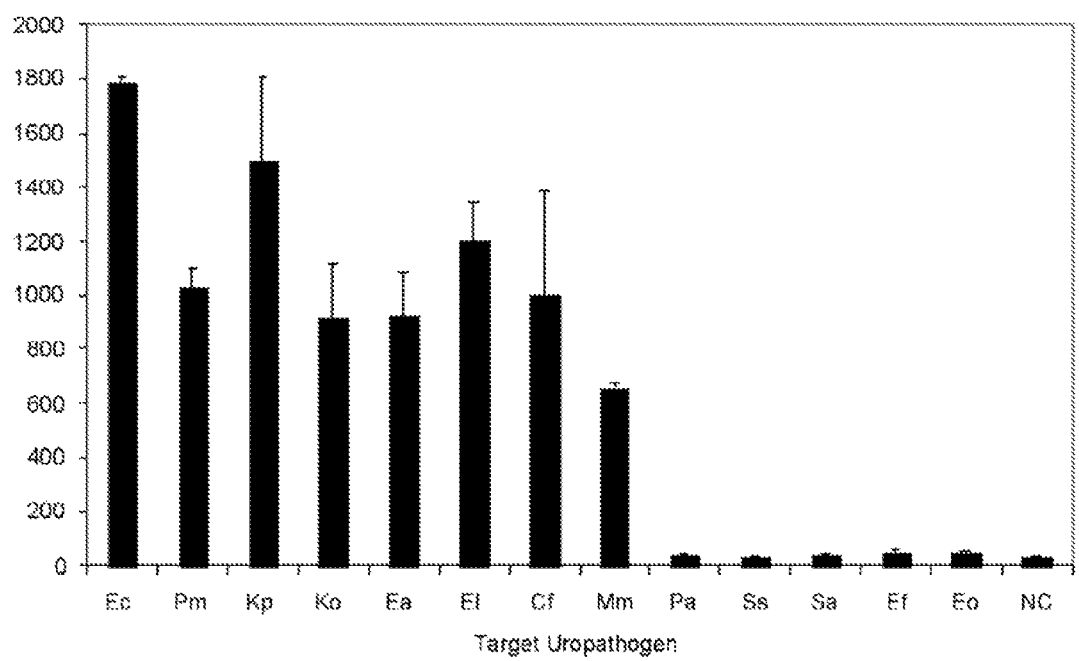
FIG. 2. Specificities of Enterobacteriaceae-specific probe pairs. Positive signals were seen for all Enterobacteriaceae species tested but not for gram-positive uropathogens (Eo, Ef, Ss, and Sa) or *P. aeruginosa* (Pa). (See the footnote to Table 2 for bacterial species abbreviations.) Means and standard deviations of experiments performed in duplicate are shown. NC refers to the negative control experiments performed with capture and detector probes but without bacterial lysate.

The present invention is based on the discovery and development of materials and methods for a rapid detection assay that permits species-specific detection of pathogens in clinical specimens. Also provided is a means of detecting antibiotic susceptibility. The invention provides an electrochemical sensor array and oligonucleotide probes specific for clinically relevant pathogen species as well as methods for rapid and efficient use of same.

DEFINITIONS

All scientific and technical terms used in this application have meanings commonly used in the art unless otherwise specified. As used in this application, the following words or phrases have the meanings specified.

As used herein, an "oligonucleotide probe" is an oligonucleotide having a nucleotide sequence sufficiently complementary to its target nucleic acid sequence to be able to form a detectable hybrid probe target duplex under high stringency hybridization conditions. An oligonucleotide probe is an isolated chemical species and may include additional nucleotides outside of the targeted region as long as such nucleotides do not prevent hybridization under high stringency hybridization conditions. Non-complementary sequences, such as promoter sequences, restriction endonuclease recognition sites, or sequences that confer a desired secondary or tertiary structure such as a catalytic active site can be used to facilitate detection using the invented probes. An oligonucleotide probe optionally may be labeled with a detectable marker such as a radioisotope, a fluorescent moiety, a chemiluminescent moiety, an enzyme or a ligand, which can be used to detect or confirm probe hybridization to its target sequence. "Probe specificity" refers to the ability of a probe to distinguish between target and non-target sequences.

The term "nucleic acid", "oligonucleotide" or "polynucleotide" refers to a deoxyribo-nucleotide or ribonucleotide polymer in either single- or double-stranded form, and unless otherwise limited, encompasses known analogs of natural nucleotides that hybridize to nucleic acids in a manner similar to naturally-occurring nucleotides.

As used herein, a "detectable marker" or "label" is a molecule attached to, or synthesized as part of a nucleic acid probe. This molecule should be uniquely detectable and will allow the probe to be detected as a result. These detectable moieties are often radioisotopes, chemiluminescent molecules, enzymes, haptens, or even unique oligonucleotide sequences.

As used herein, a "hybrid" or a "duplex" is a complex formed between two single-stranded nucleic acid sequences by Watson-Crick base pairings or non-canonical base pairings between the complementary bases.

As used herein, "hybridization" is the process by which two complementary strands of nucleic acid combine to form a double-stranded structure ("hybrid" or "duplex"), "Stringency" is used to describe the temperature and solvent composition existing during hybridization and the subsequent processing steps. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. Stringency conditions are chosen to maximize the difference in stability between the hybrid formed with the target and the non-target nucleic acid. Exemplary stringency conditions are described herein below.

As used herein, "complementarity" is a property conferred by the base sequence of a single strand of DNA or RNA which may form a hybrid or double-stranded DNA:DNA, RNA:RNA or DNA:RNA through hydrogen bonding between Watson-Crick base pairs on the respective strands. Adenine (A) ordinarily complements thymine T) or Uracil (U), while guanine (G) ordinarily complements cytosine (C). "Fully complementary", when describing a probe with respect to its target sequence, means that complementarity is present along the full length of the probe.

As used herein, "adjacent", in the context of nucleotide sequences and oligonucleotides, means immediately next to one another (end to end), such that two adjacent molecules do not overlap with one another and there is no gap between them. For example, two oligonucleotide probes hybridized to adjacent regions of a target nucleic acid molecule have no nucleotides of the target sequence (unpaired with either of the two probes) between them.

As used herein, the phrases "consist essentially of" or "consisting essentially of" mean that the oligonucleotide has a nucleotide sequence substantially similar to a specified nucleotide sequence. Any additions or deletions are non-material variations of the specified nucleotide sequence which do not prevent the oligonucleotide from having its claimed property, such as being able to preferentially hybridize under high stringency hybridization conditions to its target nucleic acid over non-target nucleic acids.

One skilled in the art will understand that substantially corresponding probes of the invention can vary from the referred-to sequence and still hybridize to the same target nucleic acid sequence. This variation from the nucleic acid may be stated in terms of a percentage of identical bases within the sequence or the percentage of perfectly complementary bases between the probe and its target sequence. Probes of the present invention substantially correspond to a nucleic acid sequence if these percentages are from 100% to 80% or from 0 base mismatches in a 10 nucleotide target sequence to 2 bases mismatched in a 10 nucleotide target sequence. In preferred embodiments, the percentage is from 100% to 85%. In more preferred embodiments, this percentage is from 90% to 1100%, in other preferred embodiments, this percentage is from 95% to 100%.

By "sufficiently complementary" or "substantially complementary" is meant nucleic acids having a sufficient amount of contiguous complementary nucleotides to form, under high stringency hybridization conditions, a hybrid that is stable for detection.

By "preferentially hybridize" is meant that, under high stringency hybridization conditions, oligonucleotide probes can hybridize with their target nucleic acids to form stable probe:target hybrids (thereby indicating the presence of the target nucleic acids) without forming stable probe:non-target hybrids (that would indicate the presence of non-target nucleic acids from other organisms). Thus, the probe hybridizes to target nucleic acid to a sufficiently greater extent than to non-target nucleic acid to enable one skilled in the art to accurately detect the presence of *E. coli, P. mirabilis, P. aeruginosa, Enterococcus* spp., the *Klebsiella-Enterobacter* group, and the Enterobacteriaceae group and distinguish their presence from that of other organisms. Preferential hybridization can be measured using techniques known in the art and described herein.

As used herein, a "target nucleic acid sequence region" of a pathogen refers to a nucleic acid sequence present in the nucleic acid of an organism or a sequence complementary thereto, which is not present in the nucleic acids of other species. Nucleic acids having nucleotide sequences complementary to a target sequence may be generated by target amplification techniques such as polymerase chain reaction (PCR) or transcription mediated amplification.

As used herein, "room temperature" means about 20-25° C.

As used herein, "a" or "an" means at least one, unless clearly indicated otherwise.

Probes of the Invention

The invention provides oligonucleotide probes that are specific for *E. coli, P. mirabilis, P. aeruginosa, Enterococcus* spp., *Acinetobacter baumannii, Serratia marcescens, Stenotrophomonas maltophilia*, the *Klebsiella-Enterobacter* group, and the Enterobacteriaceae group, as well as a universal bacterial detection probe. Direct detection of pathogens using these probes has been demonstrated in both inoculated urine and clinical urine samples from symptomatic patients. The probes include capture probes and detector probes, described in greater detail below. Additional probes are listed in the Examples below.

| Target Organism | Target Capture Sequence | Target Detector Sequence |
|---|---|---|
| P. mirabilis | CGGACCTTGCACTATCGGATG (SEQ ID NO: 22) | CGGACCAAAGCAGGGGCTCTT (SEQ ID NO: 23) |
| E. faecalis | CTGATGGATGGACCCGCGGT (SEQ ID NO: 24) | AAAGGCGCTTTCGGGTGTCG (SEQ ID NO: 25) |
| K. pneumoniae | AAGGCGD*TR*AG (SEQ ID NO: 26) | CAGCGGGGAGG (SEQ ID NO: 27) |
| E. coli | GGAGTAAAGTTAATA (SEQ ID NO: 28) | TCAGCGGGGAGGAAG (SEQ ID NO: 29) |
| Enterobacteriaceae | AGAGCAAGCGGACCTCATAAAGT (SEQ ID NO: 30) | ATACAAAGGAAGGCGACCTCGCG (SEQ ID NO: 31) |
| P. aeruginosa | GAGGGAGAAAGTGGG (SEQ ID NO: 32) | TACCGCATACGTCCT (SEQ ID NO: 33) |
| Acinetcbacter beumani | GGAGCCTACTTTAGTT (SEQ ID NO: 34) | CACTTTAAGCGAGGA (SEQ ID NO: 35) |
| Enterbacter aerogenes | GCGATAAGGTTAATAACCTTGT (SEQ ID NO: 36) | AGTACTTTCAGCGAGGAGGAAG (SEQ ID NO: 37) |
| Serratia marcescens | GGAAGGTGGTGAACTT (SEQ ID NO: 38) | CACTTTCAGCGAGGA (SEQ ID NO: 39) |
| Stenotrophomonas maltophilia | AGAAATCCAGCTGGTT (SEQ ID NO: 40) | AAGCCCTTTTGTTGGGAA (SEQ ID NO: 41) |
| Universal Bacterial Target | CCCTGGTAGTCCACGCCGT (SEQ ID NO. 42) | GAGCAAACAGGATTAGATA (SEQ ID NO: 43) |

*where D = A, G, T and R = A, G

Representative Probe Pairs

*Escherichia coli*

| | | |
|---|---|---|
| Capture | TATTAACTTTACTCC | (SEQ ID NO: 44) |
| Detector | CTTCCTCCCCCCTGA | (SEQ ID NO: 45) |

*Proteus mirabilis*

| | | |
|---|---|---|
| Capture | CATCCGATAGTGCAAGGTCCG | (SEQ ID NO: 46) |
| Detector | AAGAGCCCCTGCTTTGGTCCG | (SEQ ID NO: 47) |

*Klebsiella pneumoniae*

| | | |
|---|---|---|
| Capture | CT(TC)A(ACT)CGCCTT | (SEQ ID NO: 48) |
| Detector | CCTCCCCGCTG | (SEQ ID NO: 49) |

*Pseudomonas aeruginosa*

| | | |
|---|---|---|
| Capture | CCCACTTTCTCCCTC | (SEQ ID NO: 50) |
| Detector | AGGACGTATGCGGTA | (SEQ ID NO: 51) |

*Enterococcus spp.*

| | | |
|---|---|---|
| Capture | ACCGCGGGTCCATCCATCAG | (SEQ ID NO: 52) |
| Detector | CGACACCCGAAAGCGCCTTT | (SEQ ID NO: 53) |

Representative Probe Pairs (continued)

*Enterobacteriaceae*

| | | |
|---|---|---|
| Capture | ACTTTATGAGGTCCCCTTGCTCT | (SEQ ID NO: 54) |
| Detector | CGCGAGGTCGCCTTCCTTTGTAT | (SEQ ID NO: 55) |

*Acinetobacter baumani*

| | | |
|---|---|---|
| Capture | AACTAAAGTAGGCTCC | (SEQ ID NO: 56) |
| Detector | TCCTCGCTTAAAGTG | (SEQ ID NO: 57) |

*Enterobacter aerogenes*

| | | |
|---|---|---|
| Capture | ACAAGGTTATTAACCTTATCGC | (SEQ ID NO: 58) |
| Detector | CTTCCTCCTCGCTGAAAGTACT | (SEQ ID NO: 59) |

*Serratia marcescens*

| | | |
|---|---|---|
| Capture | AAGTTCACCACCTTCC | (SEQ ID NO: 60) |
| Detector | GTGAAAGTCGCTCCT | (SEQ ID NO: 61) |

*Stenotrophomonas maltophilia*

| | | |
|---|---|---|
| Capture | AACCAGCTGGATTTCT | (SEQ ID NO: 62) |
| Detector | TTCCCAACAAAAGGGCTT | (SEQ ID NO: 63) |

Universal Bacterial

| | | |
|---|---|---|
| Capture | ACGGCGTGGACTACCAGGG | (SEQ ID NO: 64) |
| Detector | TATCTAATCCTGTTTGCTC | (SEQ ID NO: 65) |

TABLE 1

Sequences of additional capture and detector probe pairs that have been used with the electrochemical sensor array. The capture and detector probes are chemically modified at the 5' end with biotin and fluorescein, respectively. The sequence position is with respect to the *E. coli* 16S rRNA.

| Probe | Position[a] (length) | Sequence (5'-3') | |
|---|---|---|---|
| *Escherichia coil* (EC) | | | |
| Capture | 449 (35 mer) | GTCAATGAGCAAAGGTATTAACTTTACTCCCTTCC | (SEQ ID NO: 1) |
| Detector | 408 (35 mer) | CTGAAAGTACTTTACAACCCGAAGGCCTTCTTCAT | (SEQ ID NO: 2) |
| *Proteus mirabilis* (PM) | | | |
| Capture | 202 (35 mer) | GGGTTCATCCGATAGTGCAAGGTCCGAAGAGCCCC | (SEQ ID NO: 3) |
| Detector | 162 (35 mer) | GGTCCGTAGACATTATGCGGTATTAGCCACCGTTT | (SEQ ID NO: 4) |
| *Klebsiella & Enterobacter* spp. (KE) | | | |
| Capture | 449 (35 mer) | GTCAATCGMCRAGGTTATTAACCTYAHCGCCTTCC | (SEQ ID NO: 5) |
| Detector | 408 (35 mer) | CTGAAAGTGCTTTACAACCCGAAGGCCTTCTTCAT | (SEQ ID NO: 6) |
| *Pseudomonas aeruginosa* (PA) | | | |
| Capture | 111 (35 mer) | CCCACTTTCTCCCTCAGGACGTATGCGGTATTAGC | (SEQ ID NO: 7) |
| Detector | 70 (35 mer) | TTCCGGACGTTATCCCCCACTACCAGGCACATTCC | (SEQ ID NO: 8) |
| *Enterococcus* spp (EF) | | | |
| Capture | 207 (35 mer) | TTGGTGAGCCGTTACCTCACCAACTAGCTAATGCA | (SEQ ID NO: 9) |
| Detector | 165 (35 mer) | GTCCATCCATCAGCGACACCCGAAAGCGCCTTTCA | (SEQ ID NO: 10) |
| *Enterobacteriaceae* (EB) | | | |
| Capture | 1241 (35 mer) | CGGACTACGACATACTTTATGAGGTCCGCTTGCTC | (SEQ ID NO: 11) |
| Detector | 1137 (35 mer) | GAGGTCGCTTCTCTTTGTATATGCCATTGTAGCAC | (SEQ ID NO: 12) |

TABLE 1-continued

Sequences of additional capture and detector probe pairs that have
been used with the electrochemical sensor array. The capture and
detector probes are chemically modified at the 5' end with biotin
and fluorescein, respectively. The sequence position is with respect
to the *E. coli* 16S rRNA.

| Probe | Position[a] (length) | Sequence (5'-3') | |
|---|---|---|---|
| Universal Bacterial (UNI) | | | |
| Capture | 797 (27 mer) | CATCGTTTACGGCGTGGACTACCAGGG | (SEQ ID NO: 13) |
| Detector | 766 (31 mer) | TATCTAATCCTGTTTGCTCCCCACGCTTTCG | (SEQ ID NO: 14) |

[a]Position of the 5' nucleotide in alignment with the *E. coli* 16S rRNA molecule.

Oligonucleotides may be prepared using any of a variety of techniques known in the art. Oligonucleotide probes of the invention include the sequences shown above and in Table 1, Table 5, Table 11, Table 12, and equivalent sequences that exhibit essentially the same ability to form a detectable hybrid probe:target duplex under high stringency hybridization conditions. Oligonucleotide probes typically range in size from 10 to 50 nucleotides in length. Preferred probes are 10-35 nucleotides in length, with 10-25 nucleotides being optimal for some conditions, as illustrated in the Examples below. A variety of detectable labels are known in the art, including but not limited to, enzymatic, fluorescent, and radioisotope labels.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

An advantage of the probes of the invention is their ability to hybridize to the target sequence with sufficient selectivity and strength at ambient temperature and without requiring the use of a denaturing agent. The probes of the invention can be used to detect species-specific targets at room temperature (or at body temperature), at native pH (7.0) in a 1M phosphate buffer. Accordingly, for the short (10-35 bases in length) probes of the invention, "highly stringent conditions" include hybridization and washes at 20° C. to 39° C. in 1M phosphate buffer, or other buffer containing an appropriate salt solution, at native pH (at or near 7.0).

Suitable "moderately stringent conditions" include pre-washing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

Any polynucleotide may be further modified to increase stability. Possible modifications include, but are not limited to, the addition of flanking sequences at the 5' and/or 3, ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Nucleotide sequences can be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include probe generation vectors. In general, a vector will contain an origin of replication functional in at least one organism, convenient restriction endonuclease sites and one or more selectable markers. Other elements will depend upon the desired use, and will be apparent to those of ordinary skill in the art.

Methods of the Invention

The invention provides a method for species-specific detection of pathogens in clinical and other specimens, including, e.g., sputum, urine, cerebrospinal fluid (CSF), blood, tissue sections, food, soil and water. The pathogens to be detected include those that infect human or animal subjects. Representative pathogens for detection include bacterial pathogens, such as those listed in the Tables and Examples herein, and those responsible for fungal infection in body fluids (e.g., *Candida albicans* and *Candida glabrata*), as well as others known to those skilled in the art. The method generally comprises contacting one or more probes of the invention with a specimen. For example, one can perform the method using one, two, three, four, five, six or all of the probes described herein, and/or using one or more of these probes in combination with other probes known in the art. The method can be carried out quickly, with a minimum of specimen preparation prior to assay. In one embodiment, the specimen is lysed with a lysis buffer prior to contact with the probes of the invention. The lysis buffer is sufficient to release nucleic acid molecules from the pathogen to be detected, such that the target regions of the nucleic acid molecules of the pathogen are able to hybridize with the probes. Those skilled in the art will appreciate that the lysis buffer(s) can be selected in accordance with the target pathogen(s). No denaturing agent is required, and the hybridization occurs at ambient temperature, eliminating the need for heating the specimens and allowing for rapid assay on site.

In one embodiment, the method is performed using an electrochemical sensor. One example of an electrochemical sensor suitable for use with the invention is described in the U.S. patent application assigned publication number 20020123048. The sensor array can be an integral component of a point-of-care system for molecular detection of pathogens in body fluids. Those skilled in the ad will appreciate the ease with which the particular method described in detail herein can be adapted for use with other materials, such as an automated sample preparation cartridge or optical sensors, as well as other conventional detection methods, employing the probes described herein.

In one embodiment, the method comprises contacting a lysate of the specimen with a capture probe immobilized on a substrate. The capture probe comprises a first oligonucleotide that specifically hybridizes with a first target nucleic acid sequence of the pathogen to be detected. Typically, for detection of bacterial pathogens, the target sequence is 16S rRNA (or 5S or 23S rRNA). The lysate has been brought into contact with a detector probe that comprises a detectably labeled oligonucleotide that specifically hybridizes with a second target nucleic acid sequence of the pathogen. The lysate can be brought into contact with the detector probe simultaneously with, prior to, or subsequent to, the contacting of the lysate with the capture probe. Detection of the second detectable label complexed with the substrate, e.g., detection of the presence of the detector probe, is indicative of the presence of the corresponding pathogen.

In one embodiment, the first and second nucleic acid sequences of the pathogen are adjacent to each other, such that no gap remains between the capture probe and the detector probe upon hybridization with the target nucleic acid sequences of the pathogen. In another embodiment, a gap between the first and second nucleic acid sequences is not greater than about 6 bases. As discussed in the examples below, an improved signal is observed with probes directed to adjacent regions of the target nucleic acid sequence. This observation is surprising, given the teaching in the art that a gap between sequences is necessary to avoid steric hindrance due to the presence of modifications in the probes (e.g., biotin and fluorescein) in such systems.

Bacteria contained within the specimen can be lysed using one of the lysis preparations described herein. In one embodiment, the lysis preparation comprises the universal lysis buffer containing 1% Triton X-100, 0.1 M $KH_2PO_4$, 2 mM EDTA and 1 mg/ml lysozyme. Use of the universal lysis buffer obviates the need to use separate lysis buffer for gram-positive and gram-negative bacteria. In this embodiment, the time-consuming steps of bacterial RNA and/or DNA purification are not necessary, permitting direct application of a lysed urine sample to the capture probes, improving speed and efficiency of the assay. Accordingly the method can be performed by first lysing a specimen of interest to release nucleic acid molecules of the pathogen.

Alternatively, the lysate can be prepared by contacting the specimen with a first lysis buffer comprising a non-denaturing detergent (e.g., Triton X-100) and lysozyme, or a second lysis buffer comprising NaOH. Typically the Triton X-100 is used at 0.1%, lysozyme at 1 mg/ml, and NaOH at 1M. In another embodiment, the lysing comprises contacting the specimen with both buffers in series, e.g. with the second lysis buffer, either before or after contacting the specimen with the first lysis buffer. The contacting of the specimen with the buffer(s) typically occurs at room temperature. Typically, the specimen is in contact with the lysis buffer for a total of about 10 minutes. Where a first and second lysis buffer is used, the contact with each buffer is typically about 5 minutes. Those skilled in the art are aware that the time and temperature under which the contact with lysis buffer occurs can be varied (e.g. higher temperatures will accelerate the lysis) and also optimized for a particular specimen, target pathogen and other assay conditions.

The method comprises contacting a specimen with one or more detector probes of the invention under conditions permitting hybridization of target nucleic acid molecules of pathogens (e.g., bacteria) present in the specimen with the detector probes, resulting in hybridized target nucleic acid molecules. One or more hybridized target probes are brought into contact with one or more capture probes, under conditions permitting hybridization of capture probes with target nucleic acid molecules.

Accordingly, the target nucleic acid ultimately hybridizes with both capture probe(s) and detector probe(s). Although these two hybridization steps can be performed in any order, in one embodiment, detector probe hybridizes with the target nucleic acid first, after which the hybridized material is brought into contact with an immobilized capture probe. Following a wash, the dectector:target:capture combination is immobilized on a surface to which the capture probe has been bound. Detection of probe bound to target nucleic acid is indicative of presence of pathogen.

For use with an electrochemical sensor, such as the sensor array available from GeneFluidics, inc. (Monterey Park, Calif.), the method comprises detection of current associated with binding of probe to target. In one embodiment illustrated in the example below, the capture probe is labeled with biotin and immobilized onto a surface treated with streptavidin. The detector probe in this example is tagged with fluorescein, providing an antigen to which a horse radish peroxidase-labeled antibody binds. This peroxidase, in the presence of its substrate (typically, hydrogen peroxide and tetramethylbenzidine), catalyzes a well-characterized redox reaction and generates a measurable electroreduction current under a fixed voltage potential, thereby providing an electrochemical signal to detect presence of the target nucleic acid. Those skilled in the art are aware of alternative labels and enzymes that can be used in an electrochemical assay.

The invention additionally provides a method for detecting antibiotic resistance of a specimen. The method comprises contacting the specimen with an antibiotic and a growth medium; lysing the specimen to produce a lysate of the specimen, wherein the lysing releases nucleic acid molecules from the specimen; and contacting the lysate of the specimen with a capture probe immobilized on a substrate, wherein the capture probe comprises an oligonucleotide that specifically hybridizes with a first target nucleic acid sequence region of 16S ribosomal RNA, wherein the lysate is in contact with a detector probe that comprises a detectably labeled oligonucleotide that specifically hybridizes with a second target nucleic acid sequence region of 16S ribosomal RNA. The method further comprises determining the presence or absence of labeled oligonucleotide complexed with the substrate, whereby detection of the labeled oligonucleotide complexed with the substrate is indicative of resistance to the antibiotic.

Preferably, the method for detecting antibiotic resistance is performed after first identifying and quantifying the pathogen of interest The method of detecting the presence of a pathogen set forth above can be used to identify the pathogen. Identification of the pathogen guides the selection of antibiotic to be tested for resistance. Quantitation of the pathogen guides the selection of an appropriate ratio of antibiotic to pathogen for subsequent testing. The method is then carried out by inoculation of the pathogen-containing specimen into a growth medium. The inoculation is performed at a dilution determined by the results of the quantitation. This inoculation is preferably done in both the presence and absence of antibiotic. The presence or amount of pathogen is then determined, typically by comparing the specimens inoculated in the presence and in the absence of antibiotic. A greater pathogen amount in the presence of antibiotic is indicative of resistance to the antibiotic. The comparison is typically based on comparing the amount of labeled oligonucleotide (detector probe) complexed with the substrate for inoculations into growth medium in the presence and absence of antibiotic, Kits For use in the diagnostic applications described herein, kits are also within the scope of the invention. Such kits can comprise a carrier package or container that is compartmentalized to receive one or more containers such as vials, tubes, and the like, each of the container(s) comprising one of the separate elements to be used in the method. For example, the container(s) can comprise a probe that is or can be detectably labeled. The probe(s) to be included in the kit can be selected from any of the probes disclosed herein. Preferably the probes specifically hybridize with the target sequences set forth in SEQ ID NOS: 22-43. Representative probes exhibiting this specificity are described in SEQ ID NOS: 45-65. The kit can also include a container comprising a reporter-means, such as a biotin-binding protein. e.g., avidin or streptavidin, bound to a detectable label, e.g., an enzymatic, fluorescent, or radioisotope label. In one embodiment, the kit comprises a container and one or more detector probes disclosed herein.

The kit of the invention will typically comprise the container described above and one or more other containers comprising materials desirable from a commercial and user standpoint, including buffers, diluents, filters, needles, syringes, and package inserts with instructions for use. In addition, a label can be provided on the container to indicate that the composition is used for a specific application, and can also indicate directions for use. Directions and or other information can also be included on an insert which is included with the kit.

In one embodiment, the kit further comprises a substrate to which one or more capture probes are immobilized. In one embodiment, the substrate comprises an electrochemical sensor array. Capture probes specific for different species of bacteria can be positioned on different sensors of the array. One example of an assay kit comprises all the materials to be used in performance of the assay with the exception of the specimen or sample to be assayed. A typical assay kit comprises an electrochemical sensor array to which a plurality of capture probes has been immobilized and a plurality of corresponding detector probes. In one embodiment, the plurality of probes includes probes specific for each of the bacterial pathogens disclosed herein. Optionally, the kit includes one or more control probes and/or a universal probe.

EXAMPLES

The following examples are presented to illustrate the present invention and to assist one of ordinary skill in making and using the same. The examples are not intended in any way to otherwise limit the scope of the invention.

Example 1

Rapid Species-Specific Detection of Uropathogens Using an Electrochemical Sensor Array This example demonstrates species-specific detection of bacterial pathogens in clinical specimens using an electrochemical sensor. The sensor array can be an integral component of a point-of-care system for molecular detection of pathogens in body fluids.

Uropathogen isolates and clinical urine specimens. Uropathogen isolates and clinical urine specimens were obtained from the UCLA Clinical Microbiology Laboratory with approval from the UCLA Institutional Review Board and appropriate Health Insurance Portability and Accountability Act exemption. Isolates were received in vials containing Brucella broth with 15% glycerol (BBL, Maryland) and were stored at −70° C. Overnight bacteria cultures were freshly inoculated into Luria Broth (LB) grown to logarithmic phase as measured by $OD_{600}$. Concentrations in the logarithmic phase specimens were determined by serial plating, typically yielding $10^7$-$10^8$ bacteria/ml. The uropathogens grown in LB were stored as frozen pellets at −70° C. until time of experimentation. Appropriate dilutions were made when determining the target specificity of the probes such that the different uropathogen numbers were within one order of magnitude of each other.

Probe design. Species- and group-specific capture and detector probe pairs were designed using a bioinformatics-based approach that compared 16S rDNA sequences obtained from the NCBI database (Bethesda, Md.) and from uropathogen isolates with estimated hybridization accessibility of 16S rRNA target sequences (14). In addition to species- and group-specific probe pairs, a universal probe pair was designed to hybridize with all bacterial 16S rDNA sequences. Both capture and detector probes were 27-35 bps in length, their hybridization sites typically separated by a gap of 6 bps. Capture and detector probes were synthesized with 5, biotin and 5' fluorescein modifications, respectively (MWG, High Point, N.C.).

Electrochemical sensor array. Electrochemical sensor arrays were provided by GeneFluidics (Monterey Park, Calif.). As shown in FIG. 1A, each sensor in the 16-sensor array consists of a central working electrode, surrounded by a reference electrode and an auxiliary electrode. The single layer electrode design populated with alkanethiolate self-assembled monolayer (SAM) surface modifications was described previously (16) with modifications in the electrode configuration and fabrication process. Sensor arrays used in the current study were batch fabricated by deposition of a 50 nm gold layer onto a plastic substrate. 40 μl of 0.1 mM $K_3Fe(CN)_6$ (potassium hexacyanoferrate, Sigma, St. Louis, Mo.) was applied to each sensor and cyclic voltammetry (CV) (3) was performed using a chip mounter (FIG. 1B) and a 16-channel potentiostat (GeneFluidics), as a quality control measure to characterize the alkanethiolate SAM on the sensor surface. Sensors found to have peak CV currents >100 nA were rejected to avoid sensors with incomplete SAM insulation, which would result in excessive background noise during amperometric measurement. This and each of the subsequent steps was followed by washing with a stream of deionized (DI) $H_2O$ applied to the sensor surface for approximately 2-3 sec and drying for 5 sec under a stream of nitrogen. The carboxyl termini of the SAM alkanethiols were activated and functionalized as previously described (17). In brief, each working electrode was incubated with 2.5 μl of NHS/EDC (100 mM N-hydroxysuccinimide, 400 mM N-3-dimethylaminopropyl-N-ethylcarbodiimide) for 10 min. Activated sensors were incubated in biotin (5 mg/ml in 50 mM sodium acetate) (Pierce, Rockford, Ill.) for 10 min. Biotinylated sensors were incubated in 4 μl of 0.5 U/ml of streptavidin in RNase-free $H_2O$ (Cat. No. 821739, MP Biomedicals, Aurora, Ohio) for 10 min. Streptavidin-coated sensors were incubated with biotinylated capture probes (4 µl, 1 µM in 1 M phosphate buffer, pH 7.4) for 30 min.

Figure 18A:
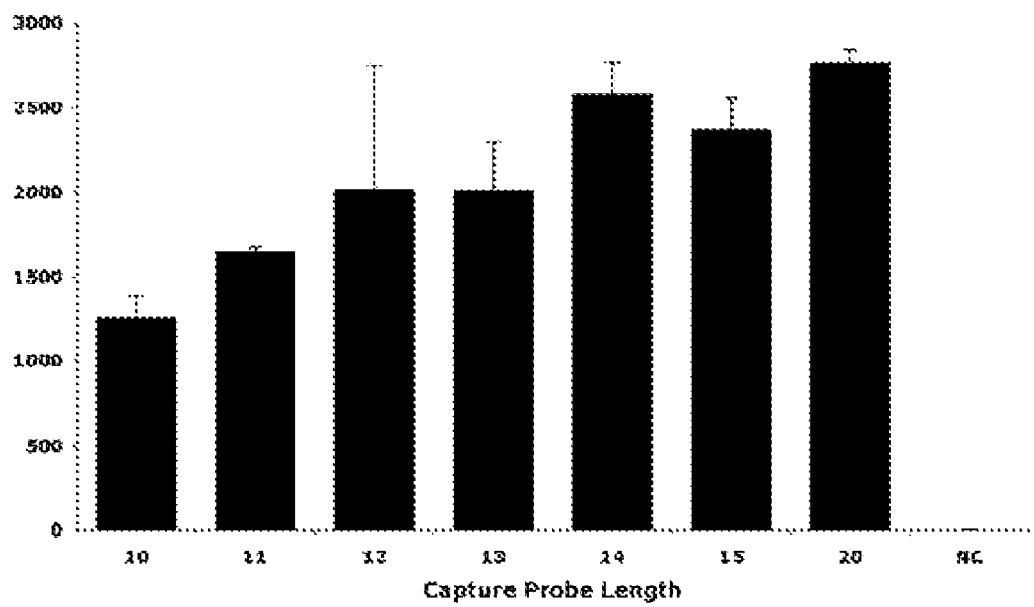
FIG. 18A-B. Electrochemical signal intensity as a function of probe length, varying the capture and detector probe (FIG. 18B) lengths independently. Current output (in nanoamperes) was measured using a series of capture and detector probes hybridized to 16S rRNA released from $9.1 \times 10^6$ *E. coli*.
Figure 18B:
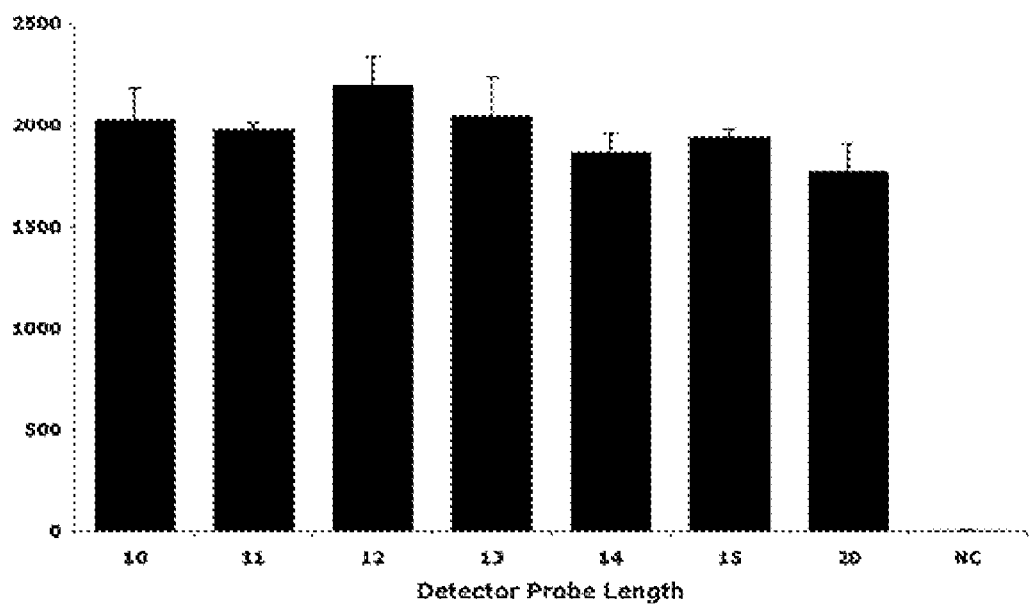
Figure 19:
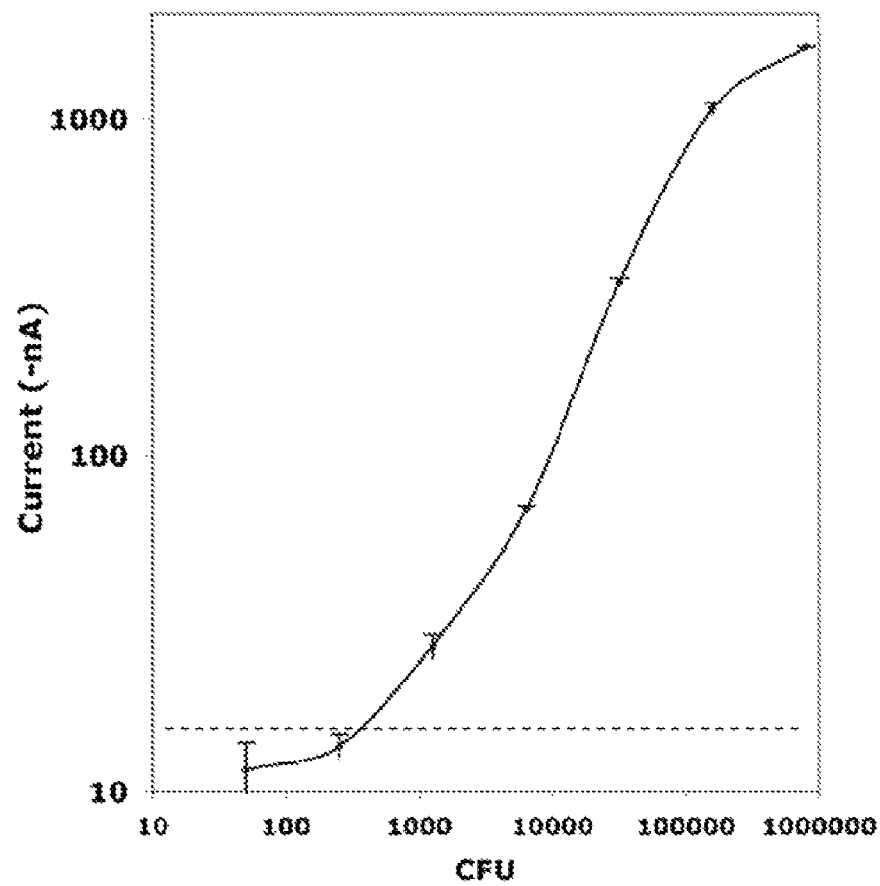
FIG. 19. Sensitivity of the electrochemical sensor assay using short probes at ambient temperature. Electrochemical sensor results from fivefold serial dilutions of E. coli cells using capture probe EC439C (15mer) paired with detector probe EC424D (15mer). Mean and SD of experiments performed in duplicate are shown. The dashed horizontal line indicates the current output threshold for duplicate results significantly greater than negative control (P<0.01).

Amperometric detection of bacterial 16S rRNA. An overview of the electrochemical sensor detection strategy is presented in panel C of FIG. 1. One ml of bacteria in Luria broth, inoculated clean urine, or clinical urine samples was centrifuged at 10,000×g for 5 min. The supernatant was discarded and the bacteria were lysed by resuspension of the pellet in 10 µl of 1 M NaOH and incubation at room temperature for 5 min. In some experiments, addition of 1M NaOH was preceded by resuspension of the bacterial pellet in 10 µl of 0.1% Triton X-100, 2 mM EDTA, and 1 mg/ml lysozyme (Sigma) in 20 mM Tris-HCl, pH 8.0, and incubation at room temperature for 5 min. 50 µl of the detector probe (0.25 µM) in 2.5% bovine serum albumin (Sigma, St. Louis, Mo.) 1 M phosphate buffer, pH 7.4, were added to the bacterial lysate and incubated for 10 min at 65° C. to allow target-probe hybridization. 4 µl of the bacterial lysate/detector probe mixture was deposited on each of the working electrodes in the sensor array and incubated for 15 min at 65° C. in a humidified chamber. After washing and drying, 4 µl of 0.5 U/ml anti-fluorescein horseradish peroxidase (HRP) Fab fragments (Roche, diluted in 0.5% casein in 10 mM phosphate buffered saline, pH 7.4) were deposited on each of the working electrodes for 15 min. After washing and drying, a prefabricated plastic well manifold (GeneFluidics, Monterey Park, Calif.) was bonded to the sensor array. The sensor array was put into the chip reader (FIG. 18) and 50 µl of 3,3',5,5'-tetramethylbenzidine (TMB), $H_2O_2$ solution (K-Blue Low Activity TMB Substrate, Neogen, Lexington, Ky.) was placed on each of the sensors in the array so as to cover all three electrodes of each sensor. Electrochemical measurements are immediately and simultaneously taken for all 16 sensors. For each array, negative control (NC) sensors were tested including the UNI capture probe, detector probe, and 2.5% bovine serum albumin (Sigma, St, Louis, Mo.) in 1 M phosphate buffer, pH 7.4, instead of bacterial lysate. The entire assay protocol was completed within 45 min from the time when bacterial lysis was commenced. Amperometric current vs. time was measured using a multichannel potentiostat (GeneFluidics). The voltage was fixed at −200 mV (vs. reference), and the electroreduction current was measured at 60 s after the HRP redox reaction reached steady state.

Clinical validity study design. Clinical urine specimens were received from routine urine cultures collected from inpatients and outpatients and submitted to the UCLA Clinical Microbiology Laboratory. Routine plating on trypticase soy agar with 5% sheep blood was performed on each specimen for phenotypic identification and colony counting while an aliquot of each specimen was held at 4° C. overnight. On the day after plating, specimens were selected for inclusion in the study on the basis of a rapid indole test for the purpose of including uropathogens other than *Escherichia coli* in approximately one-half of the specimens. The other half of the specimens were divided between *E. coli*-containing specimens and specimens determined to have ""no significant growth" or no growth" (see definitions below). Because most UTIs involve a single uropathogen, specimens determined by the clinical microbiology laboratory to have more than one organism present were excluded. Blinded specimens selected for inclusion in the study were stripped of patient identifiers and any microbiological data before delivery to the research laboratory for testing with the electrochemical sensor array.

Experiments were performed on all specimens using the 16-sensor array 'UTI Chip', in which the UNI, EB, EC, PM, KE, PA, and EF capture probes (defined in Tables 1 and 2) were tested in duplicate. The two remaining sensors served as negative controls (including capture and detector probes without bacterial lysate). The degree of variance in the electrochemical sensor measurements was determined by comparing duplicate measurements for all experiments. The background signal level was determined by averaging the $log_{10}$ results of the two negative control sensors and the $log_{10}$s results of the four lowest species-specific probe pairs (from among the EC, PM, KE, PA, and EF sensors). A receiver operating characteristic (ROC) curve analysis (29, 51) was performed to determine the optimal threshold for a positive result to maximize weighted accuracy, where weighted accuracy was defined as (5*sensitivity+specificity)/6 to account for the greater diagnostic importance of minimizing false negative results than of minimizing false positive results. Sensor results were determined in a three-step algorithm. First, the average of the $log_{10}$ UNI results was compared with background to determine whether the specimen contained bacteria, Second, for specimens predicted to contain bacteria, the identity of the bacteria in the specimen was determined by comparing the average $log_{10}$ result of the highest species-specific signal (from among the EC, PM, KE, PA, and ES sensors) with background. Third, if no species-specific signal was positive, then the average $log_{10}$ result of the EB probe pair was compared with background to determine if the bacteria present in the specimen were members of the Enterobacteriaceae family.

'UTI Chip' results were compared with clinical microbiology data after the electrochemical sensor experiment was completed. Standard clinical microbiology laboratory procedures were followed on all specimens selected for testing. Gram-negative bacilli present in specimens at a concentration $\geq 10,000$ bacteria/ml and any species present at a concentration of $\geq 100,000$ bacteria/ml were identified. Specimens with <10,000 bacterial/ml of 1-2 species or <50,000 bacteria/ml of >2 species were reported as "no significant growth". Specimens with <1,000 bacteria/ml were reported as "no growth", Results Amperometric detection of 16S rRNA using the electrochemical sensor array. When TMB and $H_2O_2$ were added to electrochemical sensors with surface-bound HRP-probe-target complexes bound to the surface, an amperometric signal was detected that rapidly increased to a steady state level within sixty seconds. In the example shown in panel D of FIG. 1, where *K. pneumoniae* 16S rRNA was bound in higher amounts to the UNI, ES, and KE sensors, the steady state current level correlated with the amount of HRP enzyme present on the sensor surface. HRP is involved in the production of amperometric signal because it catalyzes the reactions in the redox relay system that ultimately results in the transfer of electrons from the electrode to $H_2O_2$, resulting in the formation of $H_2O$. TMB functions as an electron transfer mediator between the electrode and HRP (11, 16, 27). The interactions of HRP, TMS, and $H_2O_2$ on the electrode surface are illustrated in schematic form in panel C of FIG. 1.

Development of probes for the 'UTI Chip'. The electrochemical sensor was used to determine which probe pairs had the greatest sensitivity and specificity for binding to 16S rRNA in lysates of uropathogens. Capture and detector probes were designed to hybridize to species- and group-specific regions of the 16S rRNA molecule and that are accessible to hybridization with oligonucleotide probes, as determined by prior flow cytometric analysis (14). Candidate probe pairs for *E. coli, P. mirabilis, P. aeruginosa, Enterococcus* spp, *Klebsiella* spp., *Enterobacter* spp., and the Enterobacteriaceae group were tested for uropathogen detection sensitivity and specificity using the electrochemical sensor to arrive at the optimal probe set shown in Table 1.

Figure 3:
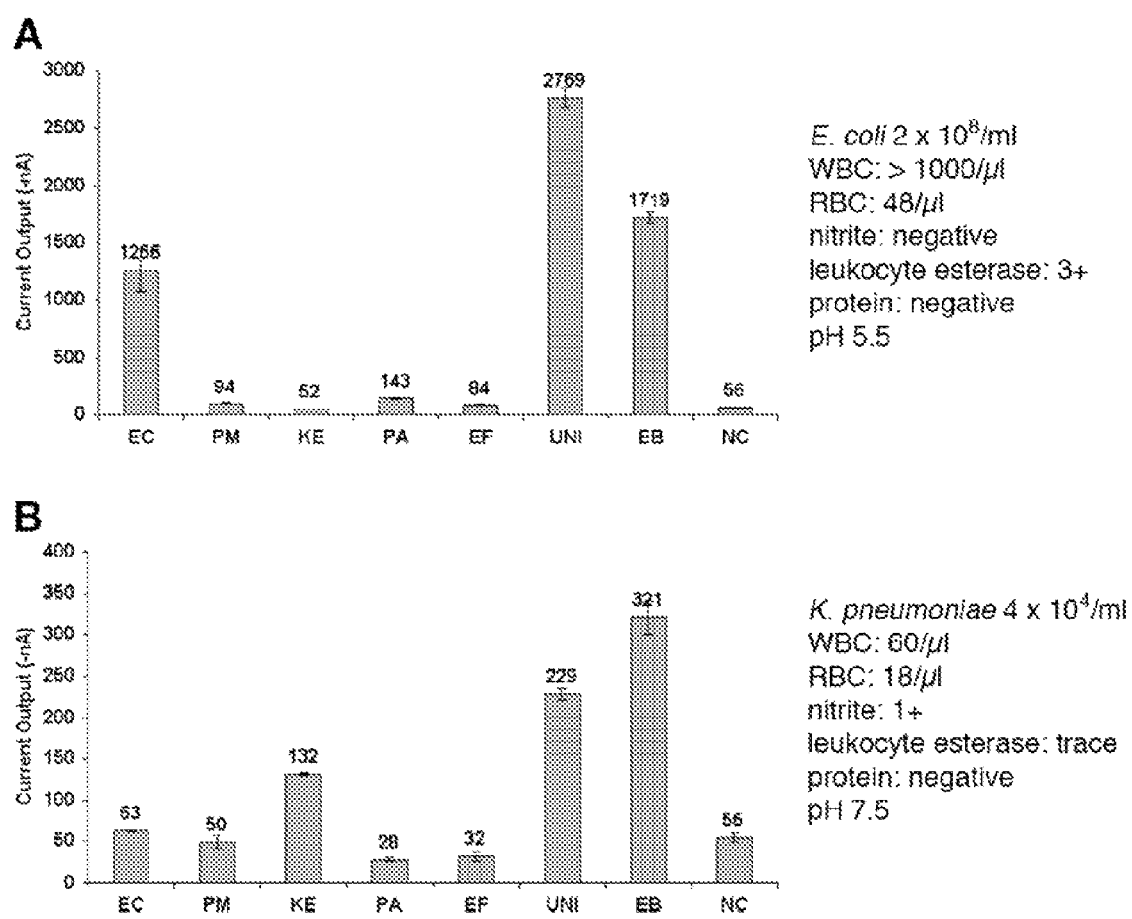
FIG. 3A-3B. Direct, species-specific detection of uropathogens in representative clinical urine specimens using the electrochemical sensor array. Current output for each of the probe pairs in the array are shown in nanoamperes. The mean current output of duplicate sensors is shown above each bar; error bars represent the standard deviation. The probe pair designation is shown below each bar, their species-specificity is given in Table 2. The urinalysis and microbiological characteristics of each specimen are shown to the right of the bar graph. Background signal level was determined by averaging the $\log_{10}$ results of the NC sensors and the sensors with the four lowest species-specific probe pairs (from among EC, PM, KE, PA, and EF) As described in the text, significant signals were 0.30 log units (5 standard deviations) above background. (A) *E. coli* in this clinical urine specimen produced significant signals in the UNI, EB, and EC sensors despite high numbers of white blood cells (WBCs). (B) 16S rRNA from as few as $4 \times 10^4$ *K. pneumoniae*/ml in urine produced significant signal levels in the UNI, EB, and KE sensors.

Table 2 summarizes of the observed specificity of the probe pairs using the electrochemical sensor array. Significant sequence similarities between *Klebsiella* and *Enterobacter* spp. 16S sequences precluded design of species-specific probes for these organisms. The Enterococcus probe pair (EF) was specific for both *E. faecalis* and *E. faecium*. The universal probe pair (UNI) detects all of the uropathogens tested. FIG. 3 shows detection by the EB probe pair of all members of the Enterobacteriaceae family tested, but not equal numbers of *P. aeruginosa, Staphylococcus* or *Enterococcus* spp. As shown in Table 2 and FIG. 3, both the UNI and ES probes detect less common uropathogens such as *Citrobacter* and *Morganella* spp., for which the species-specific probes are not yet available,

TABLE 2

Species specificity of the uropathogen probe pairs used with the electrochemical sensor array.

| Probe Pair | Species detected[a] | Species not detected[a] |
|---|---|---|
| EC | Ec | Cf, Ea, El Eo, Ko, Kp, Pa, Pm |
| PM | Pm Cf, Ea, Ec, El, Eo, Ko, Kp, Pa | |
| KE | Ea, El, Ko, Kp | Cf, Ec, Pa, Pm |
| PA | Pa | Ec, Ef, El, Eo, Kp, Pm |
| EF | Ef, Eo | Ec, Kp, Pa, Pm, Sa |
| EB | Cf, Ea, Ec, El, Ko, Kp, Mm, Pm, | Ef, Eo, Pa, Sa, Ss |
| UNI | Cf, Ea, Ec, Ef, El, Eo, Ko, Kp, Mm, Pa, Pm, Ss, Sa | None |

[a]Species abbreviations, Cf: *Citrobacter freundii*; Ea: *Enterobacter aerogenes*; Ec: *Escherichia coli*; Ef: *E. faecium*; El: *E. cloacae;* Eo: *Enterococcus faecalis*; Pm: *Proteus mirabilis*; Ko: *K. oxytoca*; Kp: *Klebsiella pneumoniae*; Pa: *Pseudomonas aeruginosa*; Mm: *Morganella morganii*; Sa: *Staphylococcus aureus*; Ss: *S. saprophyticus*.

Species-specific detection of uropathogens in clinical urine specimens. To determine analytic validity, bacteria in culture medium, inoculated urine, and clinical urine specimens were tested using the UTI Chip and 7 probe pairs with specificities relevant to the detection of the most prevalent uropathogens. Clinical urine specimens represented the most significant challenge to the electrochemical sensor detection strategy because they frequently also contained high concentrations of host proteins, white blood cells, red blood cells, cellular debris in addition to wide variations in pH. In pilot experiments, the UTI Chip produced accurate results with clinical urine specimens representing a broad range of uropathogen species and concentrations as well as broad range of urine specimen parameters related to the host inflammatory response to UTI. FIG. 3A illustrates that a high signal-to-noise ratio was maintained in the case of a clinical urine specimen from a patient with an *E. coli* UTI in which a high numbers of white blood cells were present and the pH of the urine was 5.5. The high amperometric signals using the UNI, EB, and EC sensors indicated that the streptavidin coating on the sensor surface remained intact and the target-probe hybridization step of the electrochemical sensor protocol was not inhibited by host cells or changes in urinary pH. The low background signals with the remaining sensors indicated that the SAM layer was also unaffected by exposure to urine. FIG. 38 illustrates result obtained in a urine specimen from a patient with a *K. pneumoniae* UTI containing a relatively low bacterial concentration of $4 \times 10^4$ organisms/ml, demonstrating that the detection sensitivity of the sensor was maintained despite urine specimen conditions. Table 3 summarizes the UTI Chip results for detection of uropathogens in clinical urine specimens containing these and several other bacterial species. Accurate results were obtained using the electrochemical sensor array despite high levels of protein, red blood cells and white blood cells, and variations in pH from 5.0-7.0.

TABLE 3

Urinalysis and microbiological characteristics of representative clinical urine specimens tested with the electrochemical sensor array containing 7 probe pairs ('UTI Chip'),

| Uropathogen | Concentration (cfu/ml) | Urinalysis | | | Positive Probes |
|---|---|---|---|---|---|
| | | pH | protein | RBC/μl | WBC/μl | |
| *E. coli* | $2.6 \times 10^8$ | 5.5 | Neg | 48 | >1000 | UNI, EB, EC |
| *P. mirabilis* | $>1.0 \times 10^5$ | 7.0 | 2+ | >1000 | >1000 | UNI, EB, PM |
| *K. pneumoniae* | $4.0 \times 10^4$ | 7.5 | Neg | 18 | 60 | UNI, EB, KE |
| *E. aerogenes* | $1.6 \times 10^7$ | 5.0 | Trace | 2 | 556 | UNI, EB, KE |
| *Pseudomonas* sp. | $>1.0 \times 10^5$ | 7.0 | 1+ | 177 | 103 | UNI, PA |
| *Enterococcus* sp. | $1.3 \times 10^6$ | 7.0 | Neg | 2 | 26 | UNI, EF |

Clinical validity study involving blinded clinical urine specimens A total of 89 blinded clinical urine specimens were received from the clinical microbiology laboratory. Eleven urine specimens were found to contain more than one organism and were excluded from further analysis. The remaining 78 specimens that were analyzed included 58 with bacteria speciated by the clinical microbiology laboratory, 8 specimens classified by the clinical microbiology laboratory as "no significant growth" and 12 specimens that were "no growth". The 58 positive specimens contained a broad diversity of uropathogens, 26 contained *E. coli,* 3 contained *P. mirabilis,* at 91% for a mean log positive over mean log background threshold of 0.25-0.33 log units. A 0.30 log unit threshold roughly equal to 5 standard deviations above background was applied for all sensor pairs in the array. As shown in Table 4, this approach yielded an overall sensitivity for detection of uropathogens in clinical urine specimens by the UNI probe pair of 54/58=93% (standard error +/−3.3%). UNI probe specificity to be estimated at 10/12=83% (standard error +/−10.8%), although this number could not be determined with great accuracy because there were only 12 "no growth" specimens in the sample.

TABLE 4

Detection of Gram-negative bacteria by the 'UTI Chip' in Blinded Specimens

| Clinical Microbiology Species/Result | Uni Sensors Positive/Total = Percent Mean (range)[1] | EB Sensors Positive/Total = Percent Mean (range)[1] | Species Sensors Positive/Total = Percent Mean (range)[1] |
|---|---|---|---|
| Gram-negative bacteria | 48/48 = 100% | 46/47 = 98%[2] | 43/44 = 98%[3] |
|  | 1.32 (0.40-1.84) | 1.17 (0.46-1.60) | 1.00 (0.34-1.59) |
| *Escherichia coli* | 26/26 = 100% | 25/26 = 96% | Ec 26/26 = 100% |
|  | 1.30 (0.54-1.77) | 1.17 (0.46-1.60) | 1.06 (0.48-1.59) |
| *Klebsiella pneumoniae* | 8/8 = 100% | 8/8 = 100% | KE 7/8 = 88% |
|  | 1.22 (0.40-1.84) | 1.13 (0.46-1.13) | 1.16 (0.76-1.50) |
| *Enterobacter aerogenes* | 5/5 = 100% | 5/5 = 100% | KE 5/5 = 100% |
|  | 1.35 (0.93-1.65) | 1.20 (0.82-1.52) | 0.86 (0.37-1.26) |
| *Enterobacter cloacae* | 1/1 = 100% | 1/1 = 100% | KE 1/1 = 100% |
|  | 1.43 | 1.08 | 0.34 |
| *Proteus mirabilis* | 3/3 = 100% | 3/3 = 100% | Pm 3/3 = 100% |
|  | 1.41 (1.16-1.66) | 1.14 (0.92-1.45) | 0.74 (0.48-0.96) |
| *Citrobacter freundii* | 2/2 = 100% | 2/2 = 100% | 0/2 = 0% |
|  | 1.49 (1.43-1.55) | 1.32 (1.25-1.38) | N.A. |
| *Citrobacter koseri* | 1/1 = 100% | 1/1 = 100% | 0/1 = 0% |
|  | 1.23 | 1.29 | N.A. |
| *Serratia marcescens* | 1/1 = 100% | 1/1 = 100% | False Positive |
|  | 1.67 | 1.36 | Pa 0.36 |
| *Enterobacteriaceae* | 47/47 = 100% | 46/47 = 98% | 46/47 = 98% |
|  | 1.32 (0.40-1.84) | 1.17 (0.46-1.60) | 1.02 (0.34-1.59) |
| *Pseudomonas aeruginosa* | 1/1 = 100% | 0/1 = 0% | Pa 1/1 = 100% |
|  | 1.33 | N.A. | 0.55 |
| Gram-positive bacteria | 6/10 = 60% | 0/10 = 0% | 2/8 = 25%[3] |
|  | 0.95 (0.33-1.78) | N.A. | 0.99 (0.63-1.36) |
| *Enterococcus* species | 5/8 = 63% | 0/8 = 0% | Ef 2/8 = 25% |
|  | 0.92 (0.33-1.78) | N.A. | 0.99 (0.63-1.36) |
| *Staph. saprophyticus* | 1/2 = 50% | 0/2 = 0% | 0/2 = 0% |
|  | 1.10 | N.A. | N.A. |
| All specimens with bacteria | 54/58 = 93% | 46/47 = 98%[2] | 45/52 = 87%[3] |
|  | 1.28 (0.33-1.84) | 1/17 (0/46-1.60) | 1.00 (0.34-1.59) |
| No Significant Growth | 5/3 = 63% | 0/8 = 0% | Ef 1/8 = 13% |
|  | 0.42 (0.31-0.57) | N.A. | 0.31 |
| No Growth | 2/12 = 17% | 0/12 = 0% | 0/12 = 0% |
|  | 0.38 (0.34-0.42) | N.A. | N.A. |

[1]Expressed in log10 units over background.
[2]Calculation of Enterobacteriaceae probe results does not include specimens containing Gram-positive bacteria or *P. aeruginosa,* which were not detectable using the Enterobacteriaceae probe.
[3]Calculation of species-specific probe results for Gram-negative and -positive bacteria does not include specimens containing bacteria for which no species-specific probes were included.

8 contained *K. pneumoniae,* 1 contained *E. cloacae,* 5 contained *E. aerogenes,* 1 contained *P. aeruginosa,* 2 contained *C. freundii,* 1 contained *C. koseri,* 1 contained *S. marcescens,* 8 contained *Enterococcus* spp., and 2 contained *S. saprophyticus.*

Figure 4:
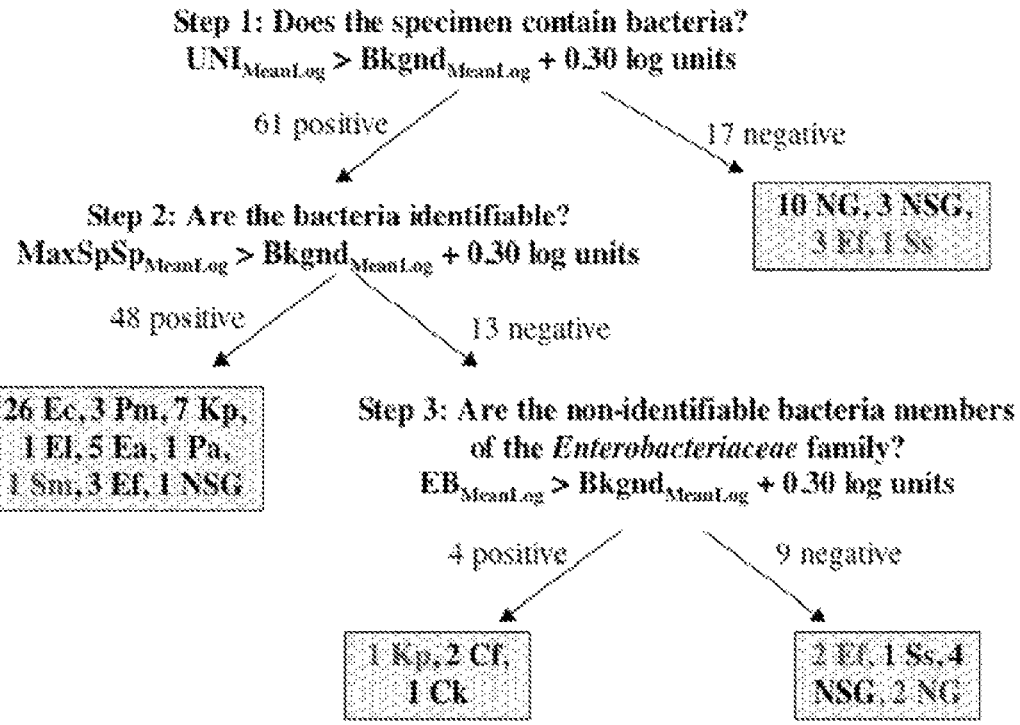
FIG. 4. 'UTI Chip' Signal Interpretation Algorithm. The three-step algorithm used to interpret the results of electrochemical sensor experiments on 78 specimens that met inclusion criteria is shown. Positive signals were those with a mean log of greater than 0.30 log units (5 standard deviations) over background. "UNI" and "EB" are eubacterial and Enterobacteriaceae-specific probe signals, respectively. "Bkgnd" is the background signal, as defined in the text of Example 1. "MaxSpSp" refers to the maximum species-specific signal. Clinical microbiology results are given in shaded boxes. Two-letter species abbreviations are given in the footnote of Table 2 (Example 1). NSG indicates "No Significant Growth". NG indicates "No Growth". Correct results are in black letters (darkest font), false-positive results are in medium dark letters (1 Sm; 2 NG), false-negative results are in red letters (gray font).

The 16 sensor array allowed each of 8 electrochemical sensor measurements (7 probe pairs plus 1 negative control) to be performed in duplicate. Sensor-to-sensor variance in the clinical study was determined by comparing the results from testing of all 78 samples, which yielded 1248 (=2×8×78) paired results. The duplicate residual errors were found to have a log normal distribution. The standard deviation of the duplicates was roughly constant at a value of 0.06 log units for all sensors in the UTI Chip array. An ROC curve analysis found that optimal UTI chip weighted accuracy was maximal The sensitivity of the UNI probe for detection of Gram-negative bacteria in clinical urine specimens was 48/48=100%, because all four falsely negative specimens contained Gram-positive bacteria. Both the Enterobacteriaceae and species-specific probe pairs demonstrated a similar 98% sensitivity for detection of Gram-negative bacteria in clinical urine specimens. FIG. 4 illustrates the three-step UTI Chip signal interpretation algorithm, which showed the high level of accuracy for detection and identification of Gram-negative bacteria in clinical urine specimens. One specimen containing *S. marcescens* was falsely positive by the PA probe pair and one specimen containing *K. pneumoniae* was falsely negative using the KE probe pair. The sensitivity of the 'UTI Chip' was lower for Gram-positive organisms; three specimens containing Enterococci and one specimen containing *S. saprophyticus* were falsely negative using the UNI probe pair.

In this study we describe a novel electrochemical sensor array platform that uses oligonucleotide capture and detector probes for detection and identification of bacterial uropathogens in clinical urine specimens. Amperometric biosensors for detection of in vitro cultivated bacteria have been previously described using antibody capture or nucleic acid hybridization approaches, but not for detection of bacteria in clinical specimens (1, 4, 9, 10, 15, 21, 26, 30, 35, 40, 43). A convergence of technological innovations from several disciplines including microfabrication, materials science, electrochemistry, and molecular microbiology contributed to the design of the electrochemical sensor array and the detection strategy utilized in the current study (16, 17, 42). The resulting biosensor demonstrated a high signal-to-noise ratio and low variance between duplicate sensors that is maintained despite contact with bacteria obtained directly from clinical urine specimens. This is the first report we are aware of describing detection of bacterial pathogens in human body fluids using an electrochemical sensor and the clinical validity of this approach.

The sensor technique utilized here is an electrochemical sandwich assay in which target 16S rRNA is bound by both a capture and detector probe (16). The capture probe anchors the target to the sensor and the detector probe provides a means for recognizing target bound on the sensor surface. This sandwich strategy has been successfully employed in several types of electrochemical sensors (5, 7, 46, 50). In our system, as in most electrochemical sandwich assays, the detector probe is linked directly or indirectly to HRP for amperometric detection of redox current (5)}(7, 50). An exception to this approach is an electrochemical sandwich assay involving a ferrocene-modified detector probe (46). When the detector probe is hybridized to the target on the sensor surface, the ferrocene moieties mediate electron transfer to the gold electrode via a phenylacetylene molecular wire embedded in the electrode's SAM. In any microfabricated electrochemical sensor the SAM reduces background current by insulating the working electrode when a potential difference is applied between the working and reference electrodes (3). When our electrochemical sensor results are to be read, the sensor is placed in a potentiostat and a voltage of −200 mV is applied between the working and auxiliary electrodes, resulting in polarization of the working electrode with negative charges. HRP substrates, such as TMB, then serve to transfer electrons from the electrode surface to HRP across the SAM (11, 16, 27).

Electrochemical sensors directly detect nucleic acid targets by hybridization, so that sensitivity and specificity problems associated with nucleic acid amplification in the presence of biological inhibitors are avoided. Accuracy of the 'UTI Chip' was demonstrated for samples with significant amounts of somatic cells, urinary protein, and ranges of pH. In contrast, PCR detection assays for urine specimens are subject to false negative results due to DNA polymerase inhibitors, which may not be removed even after a nucleic acid purification step (24, 25). Application of PCR assays to complex mixtures of nucleic acids can produce biased target amplification resulting in problems with specificity (36, 44). We and others have encountered sensitivity and specificity problems related to sample contamination and/or urinary inhibitors in our attempts to use PCR for detection of uropathogens in clinical urine specimens (38, 45) (Møller et at, unpublished data). Electrical and fluidics systems can be miniaturized, so that electrochemical sensors are potentially less expensive and more portable than sophisticated optical detection systems currently being used in PCR detection assays. These intrinsic advantages may be critical when sensor technology is eventually applied in an automated point-of-care device.

We developed a library of species-specific probes that recognize over 90% of uropathogens submitted to the clinical microbiology laboratory. 16S rRNA was chosen as the sensor target because it exists in high copy number in bacterial cells and is an essential component of ribosomes. 16S rDNA sequences of the relevant species of bacteria are well characterized and contain regions of diversity and conservation that are useful for molecular diagnostic purposes (37). Similar to probes used for 16S rRNA-based fluorescence in situ hybridization assays, the oligonucleotide probes that were developed for use with the electrochemical sensor array hybridize with species-specific and surface-accessible regions of the 16S rRNA target molecule. The panel of probes described in the clinical feasibility study was able to detect and identify a broad range of Gram-negative uropathogens. The absence of a positive signal from the UNI probe effectively rules out a Gram-negative bacterial UTI. Our detection system had reduced sensitivity for Gram-positive uropathogens such as *Enterococcus* species and *S. saprophyticus*. The most likely explanation for this problem is resistance of the Gram-positive cell wall to the alkaline lysis method used in our study. Development of alternative lysis methods that would be applicable to all potential uropathogens is an area of active investigation in our laboratory.

A short time from specimen collection to readout is important to an approach intended for a point-of-care application. Our current detection strategy requires approximately 45 minutes, bacterial lysis for 5 mins, probe hybridization for 25 mins. and enzyme amplification for 15 mins. The amperometric reading is currently being measured at 60 sec, by which point the current flow has reached steady state (FIG. 1D). The reaction kinetics in each step of the protocol is limited by passive diffusion (concentration of molecules versus time). Ale anticipate that the sample preparation time can be further reduced by optimization of bacterial lysis efficiency and hybridization kinetics.

The optical-grade surface characteristics of the gold electrodes in our electrochemical sensor array allowed for formation of pinhole-free SAMs. Highly insulating SAMs improve sensitivity by reducing sensor background and increasing the signal-to-noise ratio. Sensitivity was also improved by integrating liquid-phase detector probe/target hybridization for maximum signal detection efficiency and solid-phase probe/sensor immobilization for maximum target capture efficiency (16). The standard diagnostic criterion for UTI is greater than $10^5$ cfu/ml from clean-catch voided urine sample (23), although actual concentrations of uropathogens in clinical urine specimens are frequently higher. A robust uropathogen diagnostic system should be able to detect and quantify bacteria over a wide spectrum of bacterial concentrations and urine parameters. The studies presented here indicate that the UTI Chip is able to detect uropathogens over wide range of clinical urine characteristics (Table 3) and bacterial concentrations as low as $4 \times 10^4$ cfu/ml (FIG. 5B). The results of the clinical feasibility study proved this to be an appropriate level of sensitivity for detection of clinically relevant concentrations of bacteria in urine. Given that only 4 μl of the 60 μl lysate-probe mixture, or one-fifteenth of the total, are applied to the sensor surface, the ability to detect as few as $4.0 \times 10^4$ cfu/ml (FIG. 38) translates to a total of 2600 bacteria. *E. coli* contain between $5 \times 10^3$ to $2 \times 10^4$ copies of 16S rRNA per cell (31). Therefore, we estimate that the rRNA detection limit of the sensor is within femtomolar ($3 \times 10^{-16}$) range, which compares favorably to other electrochemical DNA sensors (8).

This level of sensitivity is achieved using raw bacterial lysates from actual body fluids, and represents an important advance compared to previous studies.

The studies presented here demonstrated the analytical and clinical validity of an electrochemical DNA sensor for quantitative, species-specific detection of uropathogens. The culture- and PCR-independent molecular identification was achieved in 45 minutes. The ability of the sensor to provide genotypic identification of uropathogens and to differentiate between bacterial pathogens in a rapid time format is clearly superior to current clinical microbiology approaches which are limited by the growth rate of bacteria and typically require at least 48 hours from sample collection to reporting. While the sensor array and the detection assay, in their present form, are not yet ready for widespread application, these are important steps towards development of a fully automated approach. The electrochemical sensor and the simplicity of its sample preparation requirements are compatible with eventual integration with an automated microfluidics-based sample preparation module. Concentration of bacteria in the urine sample, coupled with active mixing of reagents instead of passive diffusion, would significantly reduce overall sample preparation time and enhance sensitivity, Our studies lay the foundation for analyses of the clinical utility of our UTI chip. Rapid detection and identification of uropathogens at the point-of-care will have a profound impact on clinical decision-making when managing a patient with suspected UTI.

REFERENCES

1. Abdel-Hamid, I., et al. 1999. Biosens Bioelectron 14:309-16.
2. Albers, J., et al. 2003. Anal Bioanal Chem 377:521-7.
3, Bard, A, J, and L. R. Faulkner. 2001. Electrochemical Methods. Fundamentals and Applications, 2nd ed. John Wiley & Sons, Inc., Hoboken, N.J.,
4. Basu, M., et al. 2004. Glycoconj J 21:487-96.
5, Campbell, C. N., et al. 2002. Anal Chem 74:158-62.
6. Chaki, N. K., and K. Vijayamohanan. 2002. Biosens Bioelectron 17:1-12.
7. Dequaire, M., and A. Heller. 2002. Anal Chem 74:4370-7.
8. Drummond, T. G., et al. 2003. Nat Biotechnol 21:1192-9.
9. Ercole, C., et al. 2002. Sens. Actuators B 83648-52.
10. Ertl, P., et al. 2003. Biosens Bioelectron 18:907-16.
11. Fanjul-Bolado, P., et al. 2005. Anal Bioanal Chem 382:297-302.
12. Foxman, B., et al. 2000. Ann Epidemiol 10:509-15.
13. Freedman, A. L. 2005. J Urol 173:949-54.
14. Fuchs, B. M., et al. 1998. Appl Environ Microbiol 64:4973-82.
15. Gabig-Ciminska, M., et al. 2004. Microb Cell Fact 3:2.
16. Gau, J. J., et al. 2001. Biosens Bioelectron 16:745-55.
17. Gau, V., et al. 2005. Methods 37:73-83.
18. Gooding, J. J. 2002. Electroanalysis 14:1149-1156.
19. Griebling, T. L. 2005. J Urol 173:1288-94.
20. Griebling, T. L. 2005. J Urol 173:1281-7.
21. Ivnitski, D., et al. 2000. Electrochemistry Communications 2.457-460.
22. Kunin, C. M. 1997. Care of the urinary catheter, Urinary Tract Infections: Detection. Prevention, and Management, 5th ed. Williams & Wilkins, Baltimore, Md.
23. Kunin, C. M., et al. 1993. Ann Intern Med 119:454-60.
24. Land, S., et al. 2002. J Clin Microbiol 40:2893-6.
25. Mahony, J., et al. 1993. J Clin Microbiol 36:3122-6.
26. Mazenko, R. S., et al. 1999. J Microbiol Methods 36:157-65.
27. Mecheri, B., et al. 2004. IEEE Sensors Journal 4:171-179.
28. Mehrvar, M., and M. Abdi. 2004. Anal Sci 20:1113-26.
29. Metz, C. E. 1986. Invest Radiol 21:720-33.
30. Mittelmann, A. S., et al. 2002. Anal Chem 74:903-7.
31. Neidhardt, F., and H. Umbarger. 1996. Chemical composition of *Escherichia coli*, p. 13-16. In F. Neidhardt (ed.), *Escherichia coli* and *Salmonella typhimurium*, Second ed. vol. I. ASM Press, Washington, D.C.
32. Nicolle, L. 2001. Infect Med 18:153-162.
33, Palecek, E., and F. Jelen. 2002. Crit Rev Anal Chem 3:261-270.
34. Pearson, J. E., et al. 2000. Ann Clin Biochem 37 (Pt 2):119-45.
35. Perez, F. G., et al. 1998. Anal Chem 70:2380-6.
36. Polz, M. F., and C. M. Cavanaugh. 1998. Appl Environ Microbiol 64:3724-30.
37. Relman, D. A. 1999. Science 284:1308-10.
38. Rosenstraus, M., et al. 1998. J Clin Microbiol 36:191-7.
39. Schappert, S. M. 1999. Vital Health Stat 13:i-iv, 1-39.
40. Sippy, N., et al. 2003. Biosens Bioelectron 18:741-9.
41. Stamm, W. E. 1991. Am J Med 91:65S-71S.
42. Sun, C. P., et al. 2005. Mol Genet Metab 84:90-9.
43. Susmel, S., et al. 2003. Biosens Bioelectron 18:881-9.
44. Suzuki, M. T., and S. 3. Giovannoni. 1996. Appl Environ Microbiol 62:625-30.
45. Toye, B., et al. 1998. J Clin Microbiol 36:2356-8.
46. Umek, R. M., et al. 2001. J Mol Diagn 3:74-84.
47. Wang, J. 2002. Anal Chim Acta 469:63-71.
48. Wang, J. 2002. Trends Anal Chem 21:226-232.
49. Warren, J. W. 1991. Med Clin North Am 75:481-93.
50. Williams, E., et al. 2003. Biosens Bioelectron 19:165-75.
51. Zhou, X., et al. 2002. Statistical methods in diagnostic medicine. Wiley & Sons Interscience, NY.

Example 2

Determinants of Signal Intensity for Bacterial Pathogen Detection Using an Electrochemical DNA Biosensor Array This example describes the determinants of electrochemical signal intensity using a sensor assay that involves hybridization of target rRNA to a fluorescein-modified detector probe and a biotin-modified capture probe anchored to streptavidin on the sensor surface. Signal is generated by an oxidation-reduction current produced by the action of horseradish peroxidase (HRP) conjugated to an anti-fluorescein monoclonal Fab bound to the detector probe. A 12-fold increase in electrochemical signal intensity for detection of Enterococcal 16S rRNA was achieved using a two-step approach involving initial treatment with Triton X-100 and lysozyme followed by alkaline lysis. This universal lysis system was shown to be effective for both Gram-positive and Gram-negative organisms. The location of fluorescein modification was found to be a determinant of signal intensity, indicating that the distance from the sensor surface at which the HRP-Fab conjugate binds to fluorescein is important. Signal intensity was consistently higher for 3'-modified than for 5'-modified detector probes, effectively moving fluorescein away from the sensor surface. Studies with Enterococcal cells found that 3'-fluorescein modification of the detector probe combined with elimination of the gap between the detector and capture probe hybridization sites increased signal intensity by 20-fold (or more: see Example 3, below). Automation would be greatly simplified by hybridization of target with mixtures of detector probes. A mixture of seven detector probes had no adverse effects on signal intensity and species-specific detection of bacterial 16S rRNA. These studies demonstrate the feasibility of rapid, automated molecular detection of bacterial pathogens using electrochemical DNA biosensors.

Figure 5:
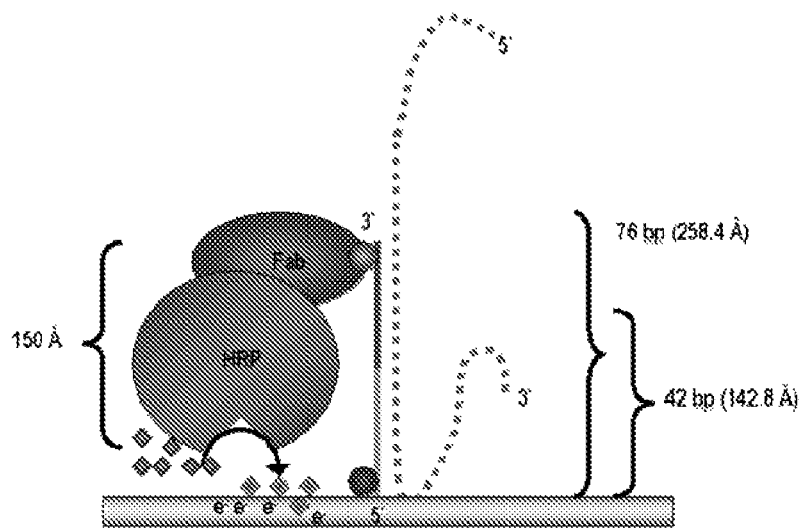
FIG. 5. Model of the electrochemical redox reporter complex. Components of the complex include the horseradish peroxidase (HRP)-Fab conjugate bound to the fluorescein (3' small circle)-modified detector probe (5' small circle). The fluorescein-modified detector probe and rRNA target (dashed line) are anchored to the sensor surface by the biotin-modified capture probe. The relative sizes of the electrochemical redox reporter complex components are provided indicating that the fluorescein of a 3'-modified detector probe would be $\leqq 25$ Å from the sensor surface. In contrast, the fluorescein of a 5-modified detector probe would be $\leqq 143$ Å from the sensor surface, indicating a role for steric hindrance to binding of the HRP-Fab conjugate to fluorescein at the 5' position of the detector probe.

Electrochemical DNA biosensors contain a recognition layer consisting of single-stranded oligonucleotides commonly known as capture probes. The mechanism of detection used for the electrochemical sensors in this study involves a redox reporter molecule that binds to a second oligonucleotide referred to as a detector probe. Binding of the capture and detector probes to the nucleic acid target functions as a three-component 'sandwich' assay to generate an electronic readout via the reporter molecule. Whole cell bacterial lysates are mixed with fluorescein-labeled detector probes for the initial target-probe hybridization in liquid phase. The target-probe hybrids are deposited on the sensor surface for the second, solid phase hybridization with the capture probe. The resulting capture-detector-target complex anchors the 16S rRNA to the sensor surface and provides for its detection (FIG. 5). Coupling the reporter enzyme (anti-fluorescein monoclonal Fab fragment conjugated to horseradish peroxidase) to the detector probe generates a redox reaction at the sensor surface when the enzyme substrate is added. Application of a fixed potential between the working and reference electrodes enables amperometric detection as the redox substrates are regenerated. The amplitude of the electroreduction current is related to the nucleic acid target concentration.

As in any assay system, the sensitivity of electrochemical sensors is affected by the signal-to-noise ratio. Reduction of background noise is largely determined by the precision of the microfabrication process and deposition of a uniform alkanethiolate self-assembled monolayer. This example examines a number of determinants of electrochemical signal intensity, namely, (1) Bacterial lysis and release of the 16S rRNA target molecules; (2) The distance of the redox reporter from the sensor surface; (3) The effect of a gap between the target hybridization regions of the capture and detector probes, and (4) Probe-probe and probe-target interactions during hybridization with mixtures of detector probes.

As shown in FIG. 5, the detection system involves hybridization of a biotin-labeled oligonucleotide capture probe and a fluorescein-labeled oligonucleotide detector probe to a nucleotide target (16S rRNA in this case). The biotin-label on the capture probe anchors the probe-target sandwich to the streptavidin self-assembled monolayer on the sensor surface. The fluorescein-label on the detector probe is not used for optical detection, rather as a binding site for the anti-fluorescein monoclonal Fab-horseradish peroxidase (HRP) conjugate. When a bias potential is applied, an electroreduction current is detected by working electrode due to the transfer of electrons by the HRP substrate between HRP and the surface of the working electrode. Signal intensity is correlated with the number of HRP molecules anchored to the sensor surface, which in turn is affected by variables including nucleotide target abundance and the configuration of the probe-target sandwich.

Sensor characterization and surface functional layer preparation. Microfabricated electrochemical sensor arrays with an alkanethiolate self-assembled monolayer (SAM) were obtained from GeneFluidics (Monterey Park, Calif.). SAM integrity was confirmed by cyclic voltammetry (CV) (1) using a 16-channel potentiostat (GeneFluidics). After CV characterization, sensor arrays were washed and dried. Washing steps were carried out by applying a stream of deionized $H_2O$ to the sensor surface for approximately 2-3 sec followed by 5 sec of drying under a stream of nitrogen. To functionalize the sensor surface, 2.5 µl of 0.5 U/ml streptavidin (Calbiochem, San Diego, Calif.) in 100 mM phosphate buffered saline, pH 7.4 was added to the alkanethiol activated sensors, incubated for 10 min at room temperature and washed off. Biotinylated capture probes (2.5 µl, 1 µM in GeneFluidics' Probe Diluent) were added to the streptavidin-coated sensors. After 30 min of incubation at room temperature, the sensor array was washed and dried, completing the surface preparation.

Bacterial strains and cultivation. Uropathogenic *Enterococcus fecalis* and *Escherichia coli* strains were obtained from the UCLA Uropathogen Strain Collection. Isolation of uropathogens from clinical urine specimens was approved by the UCLA Institutional Review Board. Isolates were inoculated into *Brucella* broth with 15% glycerol (BBL, Maryland) and were stored at $-70°$ C., Bacteria were grown overnight in Luria Broth (LB), inoculated into LB and grown to logarithmic phase as measured by $OD_{600}$. Concentration of the logarithmic phase specimens was determined by serial plating, typically yielding $10^7$-$10^8$ bacteria/ml.

Amperometric Detection of bacterial 16S rRNA. Logarithmic phase bacterial cells were concentrated by centrifugation at 10,000 rpm for 5 min. Lysis of bacterial cells was performed by addition of 10 µl of one or more of the following: 1 M NaOH, 0.1% Triton X-100 in 0.1 µM $KH_2PO_4$, 2 mM EDTA and 1 mg/ml lysozyme (Sigma). After incubation at room temperature, 50 µl of the detector probe (0.25 µM) in GeneFluidics' Probe Diluent with 2.5% bovine serum albumin (Sigma), were added to the bacterial lysate. The detector probe/bacterial lysate mixture was incubated for 10 min at 65° C. to allow hybridization of the detector probe to target rRNA. 4 µl of the bacterial lysate/detector probe mixture was deposited on each of the working electrodes in the sensor array. The sensor array was incubated for 10 min at 65° C. in a humidified chamber. After washing and drying, 2.5 µl of 0.5 U/ml anti-fluorescein horseradish peroxidase (HRP) Fab conjugate (Roche, diluted in 0.5% casein in 100 mM sodium phosphate buffer, pH 7.4) were deposited on each of the working electrodes for 10-15 min. After washing and drying, a prefabricated plastic well manifold (GeneFluidics) was bonded to the sensor array. 50 µl of HRP substrate solution (GeneFluidics) was placed on each of the sensors in the array so as to cover all three of the electrodes. Measurements were immediately and simultaneously taken for all 16 sensors. A negative control for each sensor was performed in which $H_2O$ was used instead of bacterial lysate. The entire assay protocol was completed within 45 min from the initiation of bacterial lysis. Amperometric current vs. time was measured using a multichannel potentiostat (GeneFluidics). The voltage was fixed at −200 mV (vs. reference), and the electroreduction current was measured at 60 sec after the HRP redox reaction reached steady state. All samples were analyzed in duplicate. For each experiment, negative control (NC) represents background signals in which $H_2O$ was used as the target. Positive signals are determined by comparing the signals with the background using paired T test.

Oligonucleotide probe design. Oligonucleotide probes were synthesized by MWG Biotech (High Point, N.C.). Capture probes are synthesized with 5' biotin. Detector probes with synthesized with 5'- and/or 3'-fluorescein modifications. The fluorescein molecule was used as a binding site for the anti-fluorescein monoclonal Fab-horseradish peroxidase (HRP) conjugate redox reporter. Oligonucleotide probe pairs were designed to bind to species-specific regions of the 16S rRNA molecules of *Escherichia coli* and *Enterococcus faecalis*. Studies also included oligonucleotide probe pairs specific for *Proteus mirabilis*, *Pseudomonas aeruginosa*, the *Klebsiella-Enterobacter* group, and for species belonging to the family of Enterobacteriaceae. Most experiments included a universal bacteria oligonucleotide probe pair as a positive control. The *Enterococcus* and *E. coli*-specific oligonucleotide probe pairs were studied with and without a six nucleotide interprobe gap between the hybridization regions of the capture and detector probes. The sequences of all oligonucleotide probe pairs used in this study are shown in Table 5.

Figure 6:
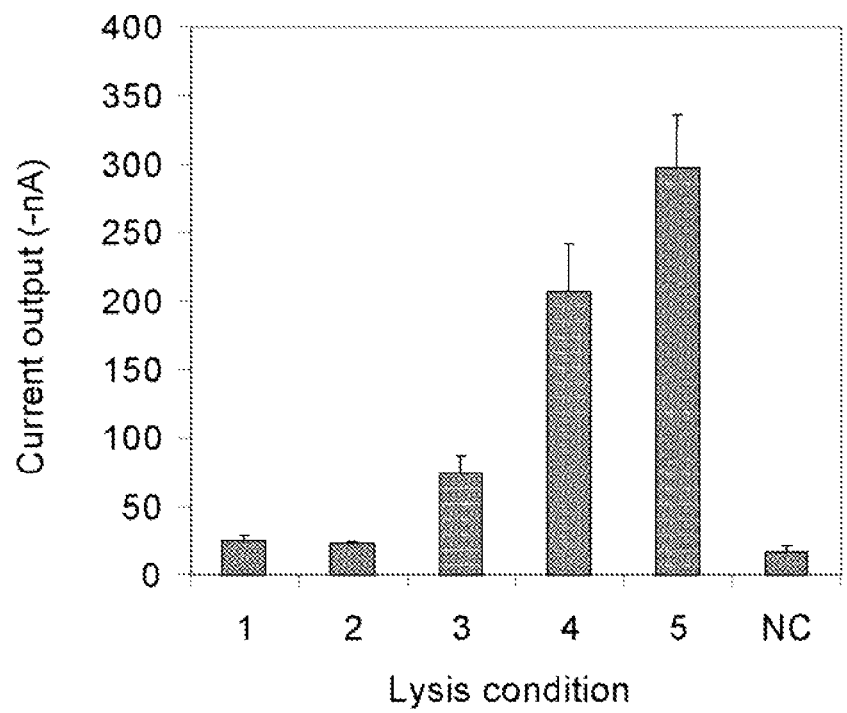
FIG. 6. The effect of lysis conditions on electrochemical signal intensity. *Enterococcus* organisms were treated with various lysis methods followed by direct electrochemical detection of 16S rRNA in the crude bacterial lysates. Under each condition, $10^5$ *Enterococcus* cells were treated at room temperature for a total of 10 min. The lysis methods are: 1) NaOH for 10 min; 2) Triton X-100 for 5 min then NaOH for 5 min; 3) Triton X-100 with lysozyme for 10 min; 4) NaOH for 5 min, then Triton X-100 with lysozyme for 5 min, 5) Triton X-100 with lysozyme for 5 min, then NaOH for 5 min. Background current output was measured using negative control (NC) sensors to which no cell lysates were applied. Current output was measured in duplicate for each lysis condition, Signal output was measured in nano-amperes (nA).

*fecalis*. Given the thicker peptidoglycan layer of Gram-positive organisms, we considered whether lysozyme would be useful component of a lysis strategy. As shown in FIG. 6, NaOH with or without Triton X-100 did not lyse *Enterococcus* cells sufficiently to detect 16S rRNA above background signal levels. However, the combination of Triton X-100 plus lysozyme resulted in signals 4 fold above background. The

TABLE 5

Sequences (5'-3') of oligonucleotide probes* used in Example 2.

Capture Probes

| | | |
|---|---|---|
| EF C207 (35-mer) | TTGGT GAGCC GTTAC CTCAC CAACT AGCTA ATGCA | (SEQ ID NO: 9) |
| EF C165 (35-mer) | GTCCA TCCAT CAGCG ACACC CGAAA CGCC TTTCA | (SEQ ID NO: 10) |
| UNI C782 (27-mer) | CATCG TTTAC GGCGT GGACT ACCAG GG | (SEQ ID NO: 13) |
| EC C434 (35-mer) | GTCAA TGAGC AAAGG TATTA ACTTT ACTCC CTTCC | (SEQ ID NO: 1) |
| EC C430 (35-mer) | GAGCA AAGGT ATTAA CTTTA CTCCC TTCCT CCCCG | (SEQ ID NO: 15) |
| EC C430 (20-mer) | ACTTT ACTCC CTTCC TCCCC | (SEQ ID NO: 16) |
| ENTBC C1241 (35-mer) | CGGAC TACGA CRYAC TTTAT GAGGT CCGCT TGCTC | (SEQ ID NO: 11) |
| PM C187 (35-mer) | GGGTT CATCC GATAG TGCAA GGTCC GAAGA GCCCC | (SEQ ID NO: 3) |
| KE C434 (35-mer) | GTCAA TCGMC RAGGT TATTA ACCTY AHCGC CTTCC | (SEQ ID NO: 5) |
| PA C102 (35-mer) | CCCAC TTTCT CCCTC AGGAC GTATG CGGTA TTAGC | (SEQ ID NO: 7) |

Detector Probes

| | | |
|---|---|---|
| EF D165 (35-mer) | GTCCA TCCAT CAGCG ACACC CGAAA GCGCC TTTCA | (SEQ ID NO: 10) |
| EF D207 (35-mer) | TTGGT GAGCC GTTAC CTCAC CAACT AGCTA ATGCA | (SEQ ID NO: 9) |
| EF D171 (35-mer) | CCGCG GGTCC ATCCA TCAGC GACAC CCGAA AGCGC | (SEQ ID NO. 17) |
| UNI D751 (31-mer) | TATCT AATCC TGTTT GCTCC CCACG CTTTC G | (SEQ ID NO: 14) |
| EC D393 (35-mer) | CTGAA AGTAC TTTAC AACCC GAAGG CCTTC TTCAT | (SEQ ID NO: 2) |
| ENTBC D1237 (35-mer) | GAGGT CGCTT CTCTT TGTAT RYGCC ATTGT AGCAC | (SEQ ID NO: 18) |
| PM D147 (35-mer) | GGTCC GTAGA CATTA TGCGG TATTA GCCAC CGTTT | (SEQ ID NO: 4) |
| KE D393 (35-mer) | CTGAA AGTGC TTTAC AACCC GAAGG CCTTC TTCAT | (SEQ ID NO: 6) |
| PA D68 (35-mer) | TTCCG GACGT TATCC CCCAC TACCA GGCAG ATTCC | (SEQ ID NO: 8) |

Test probes

| | | |
|---|---|---|
| 20-mer | CGTCA ATGAG CAAAG GTATT | (SEQ ID NO: 19) |
| 40-mer | CGTCA ATGAG CAAAG GTATT ACTCC CTTCC TCCCC GCTGA | (SEQ ID NO: 20) |
| 60-mer | CGTCA ATGAG CAAAG GTATT ACTCC CTTCC TCCCC GCTGA CGTCA ATGAG CAAAG GTATT | (SEQ ID NO: 21) |

*Capture probes were 5'- modified with biotin. Detector probes were 5'- and/or 3'-modified with fluorescein. Test probes were 5'-modified with biotin and 3'-modified with fluorescein. Probe sequence numbering based on *E. coli* 16S rDNA. Abbreviations for probe specificity: *Enterococcos* species (EF), *Escherichia coli* (EC), *Proteus mirabilis* (Pm), *Pseudomonas aeruginosa* (PA), the *Klebsiella-Enterobacter* group (KE), the *Enterobacteriaceae* family (EB), and universal bacterial (UNI) probes.

Results

Universal bacterial lysis strategy for release of 16S rRNA. Treatment of Gram-negative uropathogens such as E, coli with NaOH is an effective method for release of 16S rRNA. In contrast, a one-step alkaline lysis approach was not effective for Gram-positive uropathogens. In this example, we compared a variety of approaches for lysis and effective release of 16S rRNA from the Gram-positive organism, *Enterococcus* approach that yielded the greatest signal intensity was a two-step lysis strategy in which *Enterococcus* cells were initially treated with the combination of Triton X-100 and lysozyme for 5 min followed by treatment with NaOH for additional 5 min. Treatment of *Enterococcus* cells in reverse order, namely treatment with NaOH for 5 min followed by treatment with the combination of Triton X-100 and lysozyme for 5 min, was also successful but yielded lower signals. Although the results were not significantly better than lysis with NaOH alone, lysis of Gram-negative uropathogens (e.g. *E. coli, P. mirabilis, K. pneumoniae*, and *P. aeruginosa*) with Triton X-100 and lysozyme or Triton X-100 and lysozyme followed by NaOH resulted in successful electrochemical detection of 16S rRNA. Therefore, this two-step process can be considered a universal lysis strategy for release of bacterial 16S rRNA. Use of various concentrations of the denaturing detergent, sodium dodecyl sulfate, coupled with non-specific proteases (e.g. Proteinase K or Pronase) were not successful.

Figure 7:
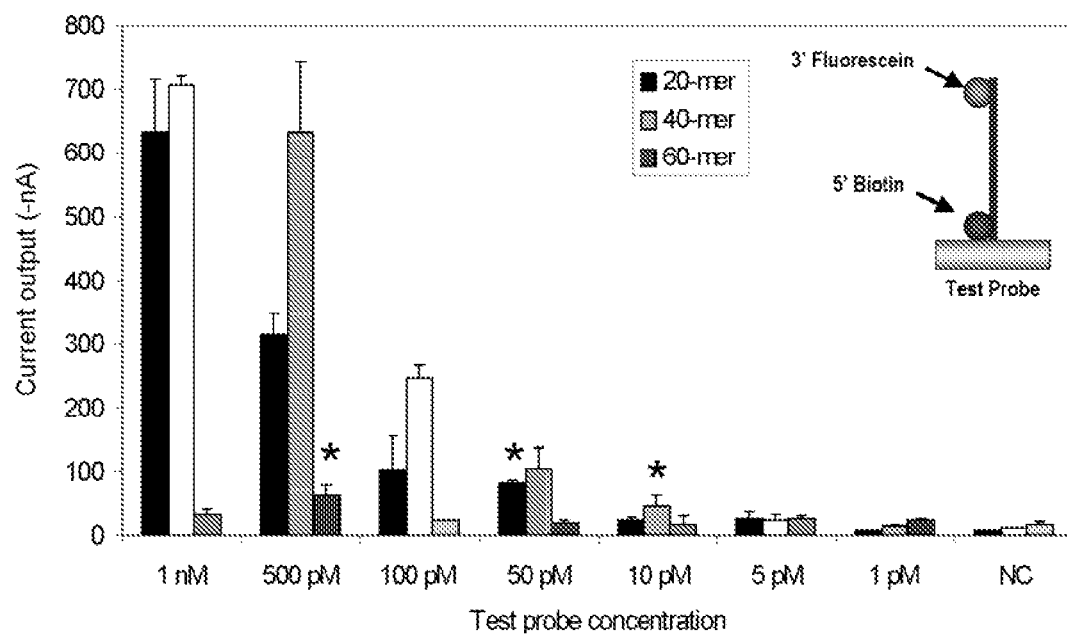
FIG. 7. The effect of oligonucleotide length on electrochemical signal intensity. Single stranded oligonucleotides ('Test Probes') ranging from 20-60 bps in length modified at the 5'- and 3'-ends with biotin and fluorescein, respectively, were tested to examine the effect of probe length on signal intensity. Hybridization was not required in these experiments because, as shown in the inset, the double-labeled probes served as a bridge between fluorescein and biotin on the electrochemical sensor surface. The highest signal output was obtained using the 40 bp probe, yielding a lower limit of detection at a concentration of 10 pM. Background current output was measured using negative control (NC) sensors to which no cell lysates were applied. Signal output was measured in nano-amperes (nA), Asterisks indicate lower limits of detection that differ significantly from background (two-tailed t test for paired samples, $P<0.05$).

Distance between fluorescein and the sensor surface. For amperometric sensors, the detection mechanism depends on the electron transfer between the signal transducer and the working electrode. For our detection approach, we considered whether the distance between the fluorescein (the binding site for the anti-fluorescein Fab-HRP conjugate) and the sensor surface would affect signal intensity. To examine this question, we tested a series of oligonucleotides of varying length, called 'Test Probes', which were modified with both biotin and fluorescein. The Test Probe was anchored on the sensor surface by the 5'-biotin modification and allowed binding of the Fab-HRP conjugate via its 3-fluorescein modification. Because both the anchoring and detection moieties were components of the same oligonucleotide, target hybridization was unnecessary for generation of an electrochemical signal. In this way, hybridization efficiency was eliminated as a confounding variable of signal intensity. Increasing the length of the Test Probe effectively increases the maximum distance between the fluorescein molecule and the sensor surface. As shown in FIG. 7, the 40mer Test Probe yielded higher signals than the 20mer Test Probe or the 60mer Test Probe across a range of different concentrations. The lower limit of detection was 10 pM concentration with the 40mer Test Probe.

Figure 8:
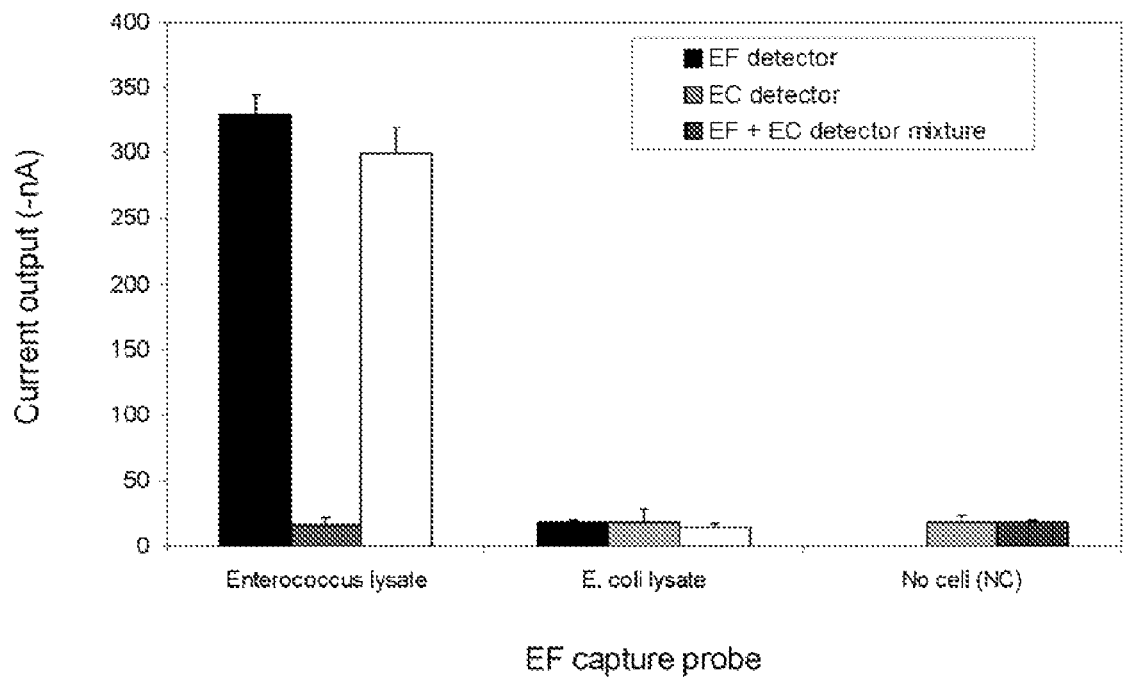
FIG. 8. Effects of a mixture of detector probes on electrochemical signal intensity. Lysates containing 16S rRNA from either *Enterococcus* or *E. coli* were hybridized with detector probes specific for *Enterococcus*, *E. coli* or a mixture of both detector probes. In each experiment, the detector probe-16S rRNA hybrids were applied to electrochemical sensors functionalized with an *Enterococcus*-specific capture probe. Mean and standard deviation of experiments performed in duplicate are shown. Background signal was determined in negative control (NC) experiments performed with capture and detector probes but without bacterial lysate. Experiments with the *Enterococcus* lysate show that there was no significant loss of signal intensity for detection of 16S rRNA target when hybridization was performed with a mixture of detector probes. Experiments with the *E. coli* lysate show that there was also no loss of capture probe specificity using a mixture of detector probes. Similar results were obtained with other 2-, 3-, and 5-detector probe mixtures.

The results of the Test Probe experiments setup indicated that the distance between fluorescein and the sensor surface could affect signal intensity. For this reason, we compared the signal intensity produced using 3'- vs. 5'-fluorescein detector probes. In the capture-detector-target complex, the fluorescein of 3'-modified detector probes would be farther away from the sensor surface than that of 5'-modified detector probes. Use of 3'-fluorescein modified detector probes resulted in greater signal intensity than 5'-fluorescein modified detector probes for detection of *Enterococcus* 16S rRNA (FIG. 8). As shown in Table 6, the effect of the location of fluorescein modification was examined for a variety of detector probes and targets. Some of the detector probes (UNI, ENTBC, EC) were also modified with fluorescein at both the 5' and 3' positions. Use of 3'-modified detector probes consistently yielded higher signals than 5'-modified detector probes, ranging from 1.4-5 fold increased signal intensity. Interestingly, fluorescein-labeling of the detector probe at both the 3' and 5' positions did not enhance signal strength beyond that achieved with 3' modification alone.

TABLE 6

Location of detector probe fluorescein modification and signal intensity[a]

| Target (Probe Pairs) | 5' (nA) | 3' (nA) (fold change) | 5' & 3' (nA) (fold change) |
|---|---|---|---|
| Ec (ENTBC D1137/C1241) | 1122 ± 25 | 2528 ± 101 (2.2×) | 2092 ± 6 (1.9×) |
| Pm (UNI D751/C782) | 1388 ± 10 | 1502 ± 33 (1.1×) | |
| Ec (UNI D751/C782) | 1890 ± 491 | 2053 ± 189 (1.1×) | 1736 ± 251 (0.9×) |
| Ec (EC D393/C434) | 1164 ± 100 | 1849 ± 141 (1.6×) | 1962 ± 244 (1.7×) |
| Ec (EC D393/C434) | 538 ± 31 | 1338 ± 24 (2.5×) | |
| Ec (EC D399/C434) | 451 ± 47 | 1258 ± 88 (2.8×) | |
| Ec (EC D393/C430) | 1588 ± 15 | 2215 ± 4 (1.4×) | |
| Ec (EC D393/C429) | 301 ± 8 | 672 ± 129 (2.2×) | |
| Pm (PM D187/C147) | 420 ± 58 | 806 ± 44 (1.9×) | |
| Pa (PA D68/C102) | 668 ± 73 | 1295 ± 237 (1.9×) | |
| Pa (PA D932/C972) | 393 ± 35 | 1314 ± 115 (3.3×) | |
| Ef (EF D165/C207) | 236 ± 59 | 1202 ± 85 (5×) | |
| Ef (EF D171/C207) | 1093 ± 32 | 1777 ± 57 (1.6×) | |

[a]Results expressed as mean of two independent measurements.
[b]Relative to results obtained with 5'-fluorescein modified detector probes.

Effect of distance between capture and detector probe hybridization sites on signal intensity. In the previous example, the capture and detector probes were typically designed with a 6-nucleotide gap between their hybridization sites. In this example, we addressed the question of whether the distance between the hybridization sites of the capture and detector probes would affect electrochemical signal intensity. Experiments involving a gap of >300 bp between the capture and detector probe produced no significant signal. We next tested capture and detector probes without a gap between their hybridization sites. There was a significant increase in signal intensity for probe pairs binding to adjacent regions of *Enterococcus* rRNA compared to probe pairs with a 6 bp gap between their hybridization sites. The combined effect of eliminating the gap between the capture and detector probe hybridization sites and moving the fluorescein modification from the 5' to the 3' end of the detector probe yielded an overall 7-fold increase in signal output. The increased signal intensity resulted in improved lower limits of detection by 25-fold. Similar trends in signal improvements were observed for modification of the *E. coli* probes (able 6), suggesting that the improvements are target sequence independent.

Effects of detector probe mixtures on signal intensity. Use of the electrochemical sensor array to identify unknown bacteria in clinical urine specimens would involve a panel of different capture and detector probes. For this reason, we examined whether hybridization of target 16S rRNA with mixtures of detector probes would affect signal intensity. When mixtures of detector probes are used, probe-probe and probe-target interactions could potentially reduce the sensitivity and specificity of the sensor. A representative experiment is shown in FIG. 8 in which *Enterococcal* 16S rRNA was hybridized with a mixture of the EF and EC detector probes versus EF detector probe alone. When the target-detector probe hybrids were applied to sensors functionalized with an EF capture probe, there was no significant difference in signal intensity between the results generated with the EF+EC detector probe mixture and results generated with the EF detector probe alone. Using the same detector and capture probes with *E. coli* 16S rRNA resulted in no significant signal, indicating that sensor specificity was retained despite hybridization of the *E. coli* target with the *E. coli*-specific detector probe. Likewise, no loss of sensitivity or specificity was observed with other 2-detector probe combinations including EC & PM, EC & KE, PA and EF. Similar results were obtained using a 3-detector-probe cocktail (EC, PM, & KE) and a 5-detector-probe cocktail (EC, PM, KE, PA, & EF), showing no significant reduction in overall signal output relative to experiments with single detector probes.

Figure 9:
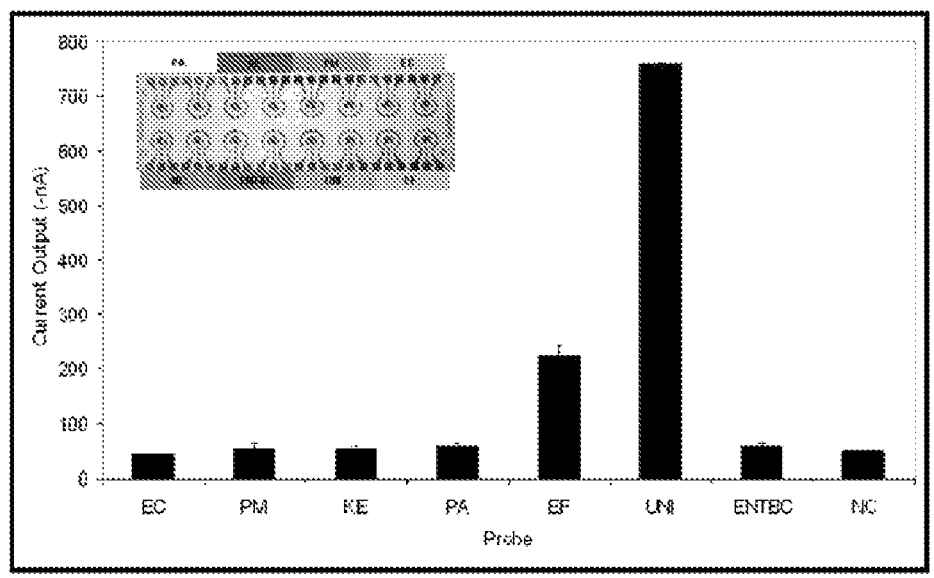
FIG. 9. Effects of hybridization with a mixture of seven detector probes on electrochemical sensor specificity. A single electrochemical sensor array immobilized with 7 different capture probes is shown schematically in the inset. $10^6$ *Enterococcus* cells were lysed and released rRNA hybridized with a mixture of seven different detector probes before application on the sensor array. Background current output was measured using negative control (NC) sensors to which no cell lysates were applied. Signal output was measured in nano-amperes (nA). The results demonstrate species-specific detection of *Enterococcus* using a mixture of seven detector probes. Asterisks indicate results that differ significantly from background (two-tailed t test for paired samples, P<0.05).

Sample preparation would be greatly simplified by including all the detector probes relevant to an entire sensor array in the target hybridization step. FIG. 9 shows results obtained when a 7-detector-probe mixture was hybridized with 16S rRNA derived from $10^6$ uropathogenic *Enterococcus*. A 16-sensor array was prepared with immobilization of 7 capture probes on pairs of sensors in duplicate. UNI capture probes were immobilized on the two negative control (NC) sensors to determine background signal levels using the 7-detector probe cocktail in the absence of target nucleic acids. The positive signals (EF and UNI) can be easily distinguished from non-specific capture probes and background signal (NC). Similar findings have been obtained when 16S rRNA derived from *E. coli, P. mirabilis, P. aeruginosa,* and *K. pneumoniae* was used as the target. These experiments indicate that signal intensity is not adversely affected by detector probe mixtures and that sensor specificity is a function of the immobilized capture probe. These studies demonstrate that a single detector probe mixture can be used as a common reagent for species-specific detection of uropathogens using an electrochemical sensor array.

This example demonstrates the determinants of signal intensity in a 40-minute DNA sandwich assay for direct molecular detection of uropathogens using a novel electrochemical sensor array. This provides an integrated point-of-care diagnostic system (lab-on-a-chip) for urinary tract infections. The sensor array would serve as the critical sensing component of an automated detection system when coupled with a microfluidics-based sample preparation module. The studies described here demonstrate the dependence of the system on the strategy for bacterial 16S rRNA release, the distance between the capture and detector probe hybridization sites on the rRNA target, and the location of the fluorescein on the detector probe relative to the sensor surface. We also demonstrate the feasibility of hybridizing bacterial target rRNA with a mixture of detector probes, which greatly simplifies the assay when using a sensor array functionalized with a panel of species- and group-specific capture probes.

A fundamental difference between Gram-positive and Gram-negative bacteria is the thicker peptidoglycan cell wall of Gram-positive organisms. We have observed that alkaline lysis is an effective lysis method for Gram-negative, but not Gram-positive, uropathogens. Given the objective of bacterial species identification in clinical specimens, we sought to devise a lysis strategy applicable to all bacterial uropathogens. Detection of intracellular biomarkers such as 16S rRNA requires effective bacterial lysis as the first step. To develop protocols and reagents compatible with eventual integration with a microfluidics-based sample preparation module, our studies were guided by the criteria of speed (<10 min), universal applicability (both Gram-positive and -negative uropathogens), overall simplicity, and compatibility with the electrochemical sensor array. This example shows that the optimal combination of using a non-denaturing detergent (Triton X-100) with lysozyme followed by alkaline treatment (NaOH) yielded highest the signals. The two-step lysis strategy was similarly effective for detection of Gram-negative bacteria. Use of other reagents such as the denaturing detergent sodium dodecyl sulfate (SOS) was not successful perhaps due to the denaturation of streptavidin on the sensor surface. The concentration of Triton X-100 (0.1%) was found to be a factor, since higher concentrations resulted in loss of surface tension of the crude lysate aliquot on the sensor surface and cross-contamination among adjacent sensors within the array. The total lysis time of 10-minute is a significant improvement over prior reports of 'rapid' bacterial lysis, which may take up to 1 hour incubation time. Using our lysis approach, direct detection of bacterial 16S rRNA without the need for additional nucleic acid purification step was successfully achieved.

The mechanism of signal production (i.e. current output) by the electrochemical sensor used in these studies involves cycling of HRP redox reaction products driven by the applied voltage potential at the sensor surface (2, 4). Because cycling is diffusion limited, the proximity of HRP (the signal transducer) and the sensor surface is likely to be an important determinant of overall signal strength. For this reason, we examined the effect of distance between the fluorescein molecule and the sensor surface on signal intensity. Experiments with 5'-biotin and 3'-fluorescein double-labeled oligonucleotides showed that signal intensity was higher for 40mers than for 20mers or 60mers (FIG. 9). These studies prompted an examination of the effect of fluorescein modification location of detector probes. As shown in FIG. 11 and Table 6, 3'-fluorescein modified detector probes consistently outperform 5'-fluorescein modified detector probes. The 3' modification effectively moves the fluorescein away from the sensor surface by 35 bp or 119 Å.

Coupled with the finding that both 3' modification and 40mer Test Probe yielded higher signals compared to their experimental counterparts (5' modification and 20mer Test Probe, respectively) in which the HRP would presumably be 'closer' to the sensor, we conclude that the while the proximity of the HRP to the sensor surface is important, optimal binding of the bulky anti-fluorescein Fab-HRP complex to the probe-target complex requires approximately 240 Å. Although the physical configurations and dimensions of the anti-fluorescein Fab-HRP complex are not known, their individual structures have been previously described: anti-fluorescein Fab fragment is 43×44×58 Å (6) and HRP is 40×67×117 Å (1). Assuming that each base pair adds 3.4 Å to the length of the DNA double helix (5), a 5' fluorescein-modified detector probe will be 36 bp or 122.4 Å from the sensor surface, whereas the 3' fluorescein-modified probe will be 70 bp or 238 Å.

While the actual size of the hybridization complex and the distance between HRP to the sensor surface in situ are likely dynamic, several mechanisms of signal reduction may be proposed if HRP is too close to the sensor surface. One interpretation of this result is that binding of the anti-fluorescein Fab-HRP to fluorescein may be sterically hindered. The observation that dual modification of the detector probe with 5' and 3' fluorescein molecules did not improve the signal may be explained by steric hindrance of efficient simultaneous binding of the anti-fluorescein Fab-HRP to both the 5' and 3' fluorescein. If the HRP is in physical contact (even transiently) with the sensor surface, the self-assembled monolayer may be locally disrupted and the electrical conductance impaired. The HRP substrates may also have limited access into the enzyme active site if it is too close to the sensor surface and thus affecting the electron transfer between oxidized substrates and the electrodes. The observations that a relatively short window of optimal distance between the HRP and the sensor surface illustrates the specificity of the detection strategy and that binding of detector probes to other regions of the 16S rRNA molecule would be unlikely contribute to signal intensity.

This example demonstrates that signal intensity is higher using *Enterococcus* and *E. coli*-specific capture and detector probe pairs that lack a gap between their hybridization sites.

DNA sandwich assays typically involve a short gap distance between the hybridization sites of the capture and detector probes or the utilization of a intervening unlabeled oligonucleotide. Recently, Metfies et at, have suggested that inclusion on a short unlabeled oligonucleotide between the capture and detector probe led to improved signals in their optical-based detection (3). In previous studies we noted that the shorter UNI probes, which have no gap between the capture and detector probe hybridization sties, consistently yielded higher signals (1.5-4 fold) then the species-specific probes which has 6 bp gap between the hybridization sites. We tested the effect of a 6 bp gap between the capture and detector probe hybridization sites, independent of the target sequence of the 16S rRNA and the length of the probes. FIG. 10 shows that for using EF probes of same length targeting the same region, removal of the interprobe gap distance resulted in 4-fold improvement of the signal output. Similar results are seen with removing the gap for EC probe hybridization site.

Without being bound by any particular theory, we postulate various non-mutually exclusive explanations for the improvement in signal strength by removal of the gap distance between the capture and detector probes. Changes in probe sequences by 6 bp to 'close the gap' may affect the hybridization kinetics by increasing the CG bps relative to AT bps. The observation that the improvement appears to hold across different sequences across 16S rRNA is suggestive that other physical characteristics irrespective of the sequence may explain that absence of a gap between capture and detector probes may be more thermodynamically stable. A single stranded gap sequence may be thermodynamically less favorable towards the hybridization of flanking capture and detector probes; whereas the absence of such single stranded sequences may render a more stable configuration. For RNA targets with complex secondary structures such as 16S rRNA, binding of the first probe may result in unwinding of rRNA helix structures and stabilize binding of the second probe. The thermodynamic advantages of such unwinding may be best realized with sequential binding of a flanking probe binding to a site immediately adjacent to the first probe. Others have suggested the use of an unlabeled bridging oligonucleotide between capture and detector probes to improve electrochemical signals (3). RNA degradation could affect the success of the sandwich formation if the probe hybridization sites are not contiguous are situated far apart.

In previous studies, detector probes were added separately to the bacterial lysate for hybridization then deposited on the sensor surface containing the capture probe. For each capture probe, therefore, a separate detector probe is added. Since the capture probes are designed from different areas within the 16S rDNA, a 'universal' detector probe from a fixed region of the 16S rDNA is not possible since the distance between the capture probes and the universal detector probe is likely too large. We tested whether it would be possible to mix the detector probes as a cocktail, in order for the use of detector probe mixtures to be successful, the following criteria need to be met-1) species-specificity conferred by capture probe; 2) no loss in signal output due to probe-probe hybridization; and 3) no significant increase in background noise resulting from non-specific binding of the detector probes to the target and the sensor surface.

Representative results shown in FIG. 8 indicate that comparable positive signals are obtained with the 2-detector-probe cocktail with the appropriate target compared to using a single detector probe. Specificity of the capture probes was retained despite using detector probe combinations. The 2-detector probe mixture did not contribute to higher background signals. The use of probe mixtures would greatly simplify the detection protocol when using a multiple detector probe mixture for identification of uropathogens in a clinical urine specimen. The advantage of using a detector probe mixture is indicated in FIG. 9 in which a 'UTI Chip' containing different capture probes is used to query a cultured specimen containing *Enterococcus* using the detector probe cocktail. The use of a detector probe mixture would facilitate the design and fabrication of the microfluidics-based sample preparation module since a single reservoir and channel can be used as supposed to individual reservoir and channel for each detector probe. We have initiated a clinical validation study using the detector probe mixture to test against unknown clinical urine specimens.

This example examines several aspects of an electrochemical DNA biosensor system for uropathogen detection to identify the determinants of signal intensity. A 'universal' lysis cocktail was developed, capable of releasing target nucleic acids from both Gram-positive and -negative uropathogens. The effects of probe length, fluorescein modification position, and distance between capture and detector probe hybridization sites were examined. Finally, the feasibility of a detector probe cocktail was demonstrated. Our findings will improve the performance of electrochemical sensors for detection of bacterial pathogens in clinical specimens. Simplified sample preparation will greatly reduce the design complexity of the microfluidics component when the sensor array is eventually integrated into an automated device. This provides for the development of a portable, point-of-care pathogen detection system that would revolutionize the diagnosis and management of infectious diseases.

LITERATURE CITED

1. Bard A J and Faulkner L R. Potential Sweep Methods. In: Electrochemical Methods: fundamentals and applications (second ed.). Hoboken: John Wiley & Sons, Inc. 2001, p. 226-260.
2. Berglund G I, et al. Nature 417: 463-468, 2002.
3. Drummond T G, et al. Nat Biotechnol 21: 1192-1199, 2003.
4. Gau J J, et al. Biosens Bioelectron 16: 745-755, 2001.
5, Griebling T L. J Urol 173: 1288-1294, 2005.
6. Griebling T L. J Urol 173, 1281-1287, 2005.
7. Metfies K, et al. Biosens Bioelectron 20: 1349-1357, 2005.
8. Pearson J E. et al. Ann Clin Biochem 37 (Pt 2): 119-145, 2000.
9. Watson J D and Crick F H. Nature 171: 737-738, 1953.
10. Whitlow M, et al. 1.85 Protein Eng 8: 749-761, 1995.

Example 3

Development of an Advanced Electrochemical DNA Biosensor

This example supplements Example 2 above with further data and additional probes for capture and detection.

The following flow chart shows the steps involved in the process of bacterial detection using the electrochemical sensor. Step 1: Bacterial lysis to release the 16S rRNA target. Step 2. Primary hybridization of the 16S rRNA target with the fluorescein-modified detector probe. Step 3. Secondary hybridization of the target-detector probe hybrid to the capture probe on the sensor surface. Step 4. Redox reaction generated by addition of anti-fluorescein horseradish peroxidase (αF-HRP), TMB substrate, and $H_2O_2$. The amount of time required for each step is shown. Washing occurs only before and after addition of αF-HRP. The entire assay was performed within 45 min.

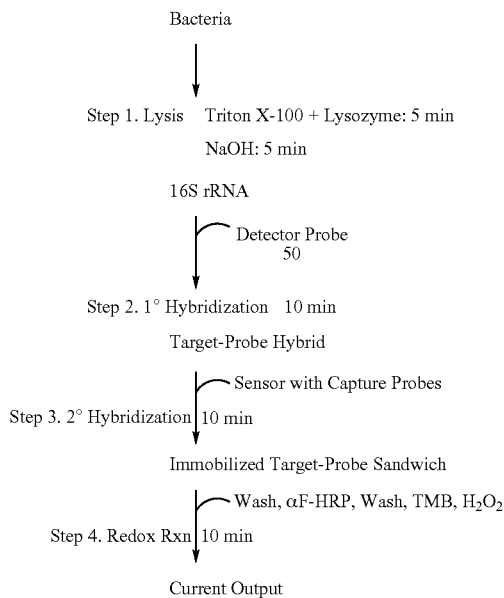

Bacterial Strains and Cultivation

The following American Type Culture Collection (ATCC) strains were obtained from the UCLA Clinical Microbiology Laboratory: *Escherichia coli* strain 35218, *Klebsiella pneumoniae* strain 13883, *K. oxytoca* strain 49131, *Enterobacter aerogenes* strain 13048. *E. cloacae* strain 13047, *Proteus mirabilis* strain 12453, *Pseudomonas aeruginosa* strain 10145, *Citrobacter freundii* strain 8090, and *Enterococcus faecalis* strain 49532. Additional strains of uropathogenic bacteria were obtained from the UCLA Uropathogen Specimen Bank: *E. coli* strain Ec103, *K. pneumoniae* strain Kp295, *P. mirabilis* strain Pm278, *P. aeruginosa* strain Pa3, and *E. faecalis* strain Eo111. Isolation of uropathogens from clinical urine specimens was approved by the UCLA and VA Greater Los Angeles Healthcare System institutional Review Boards. The identity of all clinical strains was determined by standard biochemical assays and verified by 16S rRNA gene sequencing. The 16S rRNA genes were PCR amplified with universal primers 8UA and 1485B.[17] The amplified product was purified by using the QIAquick PCR purification kit (QIAGEN, Inc., Chatsworth, Calif.) and directly sequenced using primer pairs 8UA/907B and 774A/1485B as described previously.[18] DNA sequencing was performed at the W. M. Keck Foundation Biotechnology Resource Laboratory (New Haven, Conn.). Isolates were inoculated into *Brucella* broth with 15% glycerol (BBL, Maryland) and were stored at −70° C. Bacteria were grown overnight in Luria Broth (LB), inoculated into LB and grown to logarithmic phase as measured by $OD_{600}$. Concentration of the logarithmic phase specimens was determined by serial plating, typically yielding $10^7$-$10^8$ bacteria/ml.

Oligonucleotide Probe Design

Oligonucleotide probes were synthesized by MWG Biotech (High Point, N.C.). Capture probes are synthesized with a 5' biotin modification, Detector probes were synthesized with 5'- and/or 3'-fluorescein modifications Oligonucleotide probe pairs were designed to hybridize with species-specific regions of the 16S rRNA molecules of *E. coli, E. faecalis, P. mirabilis,* and *P. aeruginosa*. Oligonucleotides were also designed as capture and detector probes for the *Klebsiella-Enterobacter* group, the family Enterobacteriaceae, and as universal bacterial probes. Probe pairs were studied with and without a gap between the hybridization regions on the 16S rRNA target. The sequences of all oligonucleotide probes used in this study are shown in Table 7.

TABLE 7

Sequences of oligonucleotide probes used in this work

Probe Designation[a] Sequence[b] (5'-3')

Capture Probes

EB1172C (35-mer)   CGGAC TACGA CRYAC TTTAT GAGGT CCGCT TGCTC (SEQ ID NO: 66)

EC434C  (36-mer)   GTCAA TGAGC AAAGG TATTA ACTTT ACTCC CTTCC (SEQ ID NO: 67)

EC430C  (35-mer)   GAGCA AAGGT ATTAA CTTTA CTCCC TTCCT CCCCG (SEQ ID NO: 68)

EF207C  (35-mer)   TTGGT GAGCC GTTAC CTCAC CAACT AGCTA ATGCA (SEQ ID NO: 69)

EF165C  (35-mer)   GTCCA TCCAT CAGCG ACACC CGAAA GCGCC TTTCA (SEQ ID NO: 70)

KE434C  (35-mer)   GTCAA TCGNC RAGGT TATTA ACCTY AHCGC CTTCC (SEQ ID NO: 71)

PA111C  (35-mer)   CCCAC TTTCT CCCTC AGGAC GTATG CGGTA TTAGC (SEQ ID NO: 72)

PA972C  (35-mer)   TGAGT TCCCG AAGGC ACCAA TCCAT CTCTG GAAAG (SEQ ID NO: 73)

PM188C  (35-mer)   GGGTT CATCC GATAG TGCAA GGTCC GAAGA GCCCC (SEQ ID NO: 74)

UNI782C (27-mer)   CATCG TTTAC GGCGT GGACT ACCAG GG          (SEQ ID NO: 75)

TABLE 7-continued

Sequences of oligonucleotide probes used in this work

Probe Designation[a] Sequence[b] (5'-3')

Detector Probes

| Probe | | Sequence | | | | | | |
|---|---|---|---|---|---|---|---|---|
| EB1137D | (35-mer) | GAGGT | CGCTT | CTCTT | TGTAT | RYGCC | ATTGT | AGCAC (SEQ ID NO: 76) |
| EB1141D | (35-mer) | TCGCG | AGGTC | GCTTC | TCTTT | GTATR | YGCCA | TTGTA (SEQ ID NO: 77) |
| EC393D | (35-mer) | CTGAA | AGTAC | TTTAC | AACCC | GAAGG | CCTTC | TTCAT (SEQ ID NO: 78) |
| EC394D | (35-mer) | GCTGA | AAGTA | CTTTA | CAACC | CGAAG | GCCTT | CTTCA (SEQ ID NO: 79) |
| EC395D | (35-mer) | CGCTG | AAAGT | ACTTT | ACAAC | CCGAA | GGCCT | TCTTC (SEQ ID NO: 80) |
| EC396D | (35-mer) | CCGCT | GAAAG | TACTT | TACAA | CCCGA | AGGCC | TTCTT (SEQ ID NO: 81) |
| EC397D | (35-mer) | CCCGC | TGAAA | GTACT | TTACA | ACCCG | AAGGC | CTTCT (SEQ ID NO: 82) |
| EC398D | (35-mer) | CCCCG | CTGAA | AGTAC | TTTAC | AACCC | GAAGG | CCTTC (SEQ ID NO: 83) |
| EC399D | (35-mer) | TCCCC | GCTGA | AGTA | CTTTA | CAACC | CGAAG | GCCTT (SEQ ID NO: 84) |
| EF165D | (35-mer) | GTCCA | TCCAT | CAGCG | ACACC | CGAAA | GCGCC | TTTCA (SEQ ID NO: 85) |
| EF171D | (35-mer) | CCGCG | GGTCC | ATCCA | TCAGC | GACAC | CCGAA | AGCGC (SEQ ID NO: 86) |
| EF207D | (35-mer) | TTGGT | GAGCC | GTTAC | CTCAC | CAACT | AGCTA | ATGCA (SEQ ID NO: 87) |
| KE393D | (35-mer) | CTGAA | AGTGC | TTTAC | AACCC | GAAGG | CCTTC | TTCAT (SEQ ID NO: 88) |
| KE399D | (35-mer) | TCCCC | GCTGA | AAGTG | CTTTA | CAACC | CGAAG | GCCTT (SEQ ID NO: 89) |
| PA68D | (35-mer) | TTCCG | GACGT | TATCC | CCCAC | TACCA | GGCAG | ATTCC (SEQ ID NO: 90) |
| PA74D | (35-mer) | GCCCG | TTTCC | GGACG | TTATC | CCCCA | CTACC | AGGCA (SEQ ID NO: 91) |
| PA932D | (35-mer) | CAGCA | TGTCA | AGGCC | AGGTA | AGGTT | CTTCG | CGTTG (SEQ ID NO: 92) |
| PM147D | (35-mer) | GGTCC | GTAGA | CATTA | TGCGG | TATTA | GCCAC | CGTTT (SEQ ID NO: 93) |
| PM153D | (35-mer) | TGCTT | TGGTC | CGTAG | ACATT | ATGCG | GTATT | AGCCA (SEQ ID NO: 94) |
| UNI751D | (31-mer) | TATCT | AATCC | TGTTT | GCTCC | CCACG | CTTTC | G (SEQ ID NO: 95) |

[a]Capture probes were 5'- modified with biotin. Detector probes were 5'- and/or 3'-modified with fluorescein. Probe sequence numbering based on *E. coli* 16S rDNA. Abbreviations for probe specificity: *Enterococcus* species (EF), *Eschernichia coli* (EC), *Proteus mirabilis* (Pm), *Pseudomonas aeruginosa* (PA), the *Klebsiella-Enterobacter* group (KE), the *Enterobacteriaceae* family (EB), and universal bacterial (UNI) probes.

Sensor Characterization and Surface Functional Layer Preparation

Microfabricated electrochemical sensor arrays with an alkanethiolate self-assembled monolayer (SAM) were obtained from GeneFluidics (Monterey Park, Calif.). SAM integrity was confirmed by cyclic voltammetry (CV)[19] using a 16-channel potentiostat (GeneFluidics). After CV characterization, sensor arrays were washed and dried. Washing steps were carried out by applying a stream of deionized $H_2O$ to the sensor surface for approximately 2-3 sec followed by 5 sec of drying under a stream of nitrogen. To functionalize the sensor surface, 2.5 µl of 0.5 U/ml streptavidin (Calbiochem, San Diego, Calif.) in 100 mM phosphate buffered saline, pH 7.4 was added to the alkanethiol activated sensors, incubated for 10 min at room temperature and washed off. Biotinylated capture probes (2.5 µl, 1 µM in 1 M phosphate buffer, pH 7.4) were added to the streptavidin-coated sensors. After 30 min of incubation at room temperature, the sensor array was washed and dried, completing the surface preparation.

Amperometric Detection of Bacterial 16S rRNA

Logarithmic phase bacterial cells were concentrated by centrifugation at 10.000 rpm for 5 min, Lysis of bacterial cells was performed by addition of 10 µl of one or more of the following 1 µM NaOH. 0.1% Triton X-100 in 20 mM Tris-HCl, pH 8.0, 2 mM EDTA and 1 mg/ml lysozyme (Sigma). After incubation at room temperature, 50 µl of the detector probe (0.25 µM) in 2.5% bovine serum albumin (Sigma)—1 M phosphate buffer, pH 7.4, was added to the bacterial lysate. The detector probe/bacterial lysate mixture was incubated for 10 min at 65° C. to allow hybridization of the detector probe to target rRNA. 4 µl of the bacterial lysate/detector probe mixture was deposited on each of the working electrodes in the sensor array. The sensor array was incubated for 10 min at 65° C. in a humidified chamber. After washing and drying, 4 µl of 0.5 U/mil anti-fluorescein horseradish peroxidase (HRP) Fab conjugate (Roche, diluted in 0.5% casein in 1 M sodium phosphate buffer, pH 7.4) were deposited on each of the working electrodes for 10-15 min. After washing and drying, a prefabricated plastic well manifold (GeneFluidics) was bonded to the sensor array. 50 µl of HRP substrate solution (K-Blue Aqueous TMB, Neogen, Lexington, Ky.) was placed on each of the sensors in the array so as to cover all three of the electrodes. Measurements were immediately and simultaneously taken for all 16 sensors. The entire assay protocol was completed within 45 min from the initiation of bacterial lysis. Amperometric current vs. time was measured using a multichannel potentiostat (GeneFluidics). The voltage was fixed at −200 mV (vs. reference), and the electroreduction current was measured at 60 sec after the HRP redox reaction reached steady state. Negative controls were included in each experiment in which 1 M phosphate buffer, pH 7.4, was used as the target instead of bacterial lysate. All samples were analyzed in duplicate.

Experiments were performed on ATCC strains to verify probe specificity using a 16-sensor array "UTI chip" in which the UNI782C, EB1176C, EC434C, KE434C, PM187C, PA102C, and EF207C 5'-biotinylated capture probes (defined in Table 1) were tested in duplicate. The two remaining sensors in the array served as negative controls (using capture probe UNI782C without bacterial lysate). Bacterial lysates were combined with a mixture of the following 3'-fluorescein labeled detector probes: UNI751D, EB1141D, EC399D, KE399D, PM153D, PA74D, and EF171D (defined in Table 7) The degree of variance in the electrochemical sensor measurements was determined by comparing duplicate measurements for all experiments. The background signal level was determined by averaging the log, results of the two negative control sensors. Positive signals were defined as signals greater than five standard deviations (in $\log_{10}$ units) over background.

Results

Universal Bacterial Lysis Strategy for Release of 16S rRNA

An effective 16S rRNA detection system for uropathogens requires efficient lysis of both Gram-negative as well as Gram-positive organisms. Previous work had shown that alkaline lysis efficiently released 16S rRNA from Gram-negative but not Gram-positive bacteria[16]. For this reason, we examined a variety of methods for rapid release of 16S rRNA from the Gram-positive uropathogen, E. faecalis. Given the thicker cell wall of Gram-positive organisms, we considered whether membrane-active detergents and/or peptidoglycan-specific enzymes would be useful components of an effective lysis strategy. As shown in FIG. 6, NaOH, with or without the detergent Triton X-100, did not lyse Enterococcus cells sufficiently for electrochemical detection of 16S rRNA above background signal levels. However, the combination of 0.1% Triton X-100 plus 1 mg/ml lysozyme resulted in a 3-fold increase in current output over background. The approach that yielded the highest electrochemical signal intensity was a strategy in which Enterococcus cells were initially treated with the combination of Triton X-100 and lysozyme for 5 min followed by treatment with NaOH for an additional 5 min. This two-step lysis method resulted in a 12-fold increase in electrochemical signal compared to alkaline lysis alone. The sequence in which these treatments were applied was important. Alkaline lysis prior to application of Triton X-100 and lysozyme was not as effective as treatment with NaOH after the detergent-enzyme combination. Longer periods of lysis did not further enhance signal intensity. Lysis of Gram-negative uropathogens (e.g. E. coli, P. mirabilis, K. pneumoniae, and P. aeruginosa) with Triton X-100 and lysozyme or Triton X-100 and lysozyme followed by NaOH resulted in successful electrochemical detection of 16S rRNA, although the results were not significantly better than lysis with NaOH alone. Therefore, this two-step process can be considered a universal lysis strategy for release of bacterial 16S rRNA. Use of various concentrations of the denaturing detergent, sodium dodecyl sulfate, coupled with non-specific proteases (e.g. Proteinase K or Pronase) did not further improve electrochemical signal strength.

Effect of Distance Between Capture and Detector Probe Hybridization Sites

The effect of distance between the capture and detector probe hybridization sites on the 16S rRNA target was examined. Experiments involving a variety of 16S rRNA targets using capture and detector probes with hybridization sites separated by a gap of >300 nt produced no significant electrochemical current output, even though these probes were known to function well as members of juxtaposed probe pairs. In contrast, capture and detector probes with hybridization sites separated by relative short interprobe gaps of up to 6 nt yielded positive signals. As shown in FIG. 10, there was a negative correlation (Pearson product-moment correlation coefficient r=−0.84) between signal intensity and the size of the gap between the capture and detector probe hybridization sites, even for very short interprobe gaps. Maximal signal intensity required eliminating the interprobe hybridization site gap between probe pairs specific for the Klebsiella-Enterobacter group, P. aeruginosa, and P. mirabilis (Table 8), which bind to various regions of the 16S rRNA target. These results indicate that the effect of an interprobe gap on signal intensity is independent of the 16S rRNA target hybridization site and species of origin.

TABLE 8

Effect of a gap between the capture and detector probe hybridization sites

| Target[a] (0 bp: 6 bp) | Probe Pair (Gap) | nA ± Std Dev | Probe Pair (Gap) | nA ± Std Dev | % change |
|---|---|---|---|---|---|
| Ec | EC 434C/393D[b] (6 nt) | 590 ± 65 | EC 434C/399D[b] (0 nt) | 3242 ± 85 | 549%* |
| Ef | EF 207C/165D[b] (6 nt) | 1202 ± 85 | EF 207C/171D[b] (0 nt) | 1777 ± 57 | 148% |
| Kp | KP 434C/393D[b] (6 nt) | 2106 ± 186 | KE 434C/399D[b] (0 nt) | 7789 ± 93 | 370%* |
| Kp | KP 972C/932D[c] (6 nt) | 1438 ± 151 | KE 972C/938D[c] (0 nt) | 2975 ± 610 | 207%* |
| Pa | PA 102C/68D[b] (6 nt) | 2483 ± 85 | PA 102C/74D[b] (0 nt) | 5455 ± 35 | 220%* |
| Pm | PM 187C/147D[b] (6 nt) | 908 ± 19 | PM 187C/153D[b] (0 nt) | 3361 ± 248 | 370%* |

*Current output measurements significantly (>5 standard deviations) greater than background
[a]Species abbreviations: Ec, Escherichia coli; Ef, Enterococcus faecalis; Kp, Klebsiella pneumoniae; Pa, Pseudomonas aeruginosa; Pm, Proteus mirabilis.
[b]3'-fluorescein-modified detector probe
[c]5'-fluorescein-modified detector probe Effect of Location of Fluorescein-Modification on the Detector Probe We considered whether the location of the fluorescein (the binding site for the anti-fluorescein Fab-HRP conjugate) on the detector probe affected signal intensity. To examine this question, we compared the signal intensity produced using 3'-vs. 5'-fluorescein modified detector probes. Use of 3'-fluorescein modified detector probes resulted in greater signal intensity than 5'-fluorescein modified detector probes for detection of both *Enterococcus faecalis* (FIG. 12A) and *E. coli* (FIG. 12B) 16S rRNA. As shown in FIGS. 11A-B, there was an additive effect of removing the interprobe gap between the capture and detector probe hybridization sites and moving the fluorescein modification from the 5' to the 3' end of the detector probe. Experiments using five-fold dilutions of enterococcal and *E. coli* cells showed that the probe pair with a 0 nucleotide gap and a 3'-fluorescein modified detector probe had a 24-29 fold lower limit of detection sensitivity compared to the probe pair with a 6 nucleotide gap and a 5'-fluorescein modified detector probe (FIG. 12).

As shown in Table 9, we examined whether the effect of the location of fluorescein modification was generalizable for a variety of detector probes and targets. Some of the detector probes (UNI751D, EB1137D, EC399D) were also modified with fluorescein at both the 5' and 3' positions. Significant increases in electrochemical current output were achieved using fluorescein modification at the 3, position compared to the 5' position for all the species-specific detector probes. Interestingly, the location of fluorescein-modification had no effect on signal intensity in the case of the universal (UNI751D) bacterial detector probe. In addition, fluorescein-labeling of the detector probe at both the 3' and 5' positions did not enhance signal strength beyond that achieved with 3' modification alone.

TABLE 9

Effect of location of detector probe fluorescein modification[a]

| Target[a] | Probe Pair | 5' Fluorescein (nA ± Std Dev) | 3' Fluorescein (nA ± Std Dev) | % change (3':5') |
|---|---|---|---|---|
| Ef | EF 207C/165D[b] | 236 ± 59 | 1202 ± 85 | 510%* |
| Ef | EF 207C/171D[c] | 1093 ± 32 | 1777 ± 57 | 163%* |
| Ec | EC 434C/399D[c] | 2837 ± 569 | 3242 ± 85 | 114% |
| Ec | EC 434C/393D[b] | 291 ± 33 | 590 ± 65 | 203%* |
| Ec | EC 430C/393D[c] | 1060 ± 173 | 1531 ± 26 | 144% |
| Ec | EB 1176C/1137D[d] | 1122 ± 35 | 2528 ± 144 | 225%* |
| Ec | UNI 782C/751D[c] | 1890 ± 491 | 2053 ± 189 | 109% |
| Pm | PM 188C/147D[b] | 420 ± 58 | 806 ± 45 | 192%* |
| Pm | UNI 782C/751D[c] | 1388 ± 10 | 1502 ± 33 | 108% |
| Pa | PA 111C/68D[b] | 668 ± 73 | 1295 ± 238 | 194%* |
| Pa | PA 972C/932D[b] | 393 ± 35 | 1314 ± 115 | 334%* |

*Current output measurements significantly (>5 standard deviations) greater than background
[a]Species abbreviations: Ef, *Enterococcus faecalis*; Ec, *Escherichia coli*; Pm, *Proteus mirabilis*; Pa, *Pseudomonas aeruginosa*.
[b]6 nucleotide gap between the capture and detector probe hybridization sites.
[c]0 nucleotide gap between the capture and detector probe hybridization sites.
[d]4 nucleotide gap between the capture and detector probe hybridization sites.

Effects of Detector Probe Mixtures on Signal Intensity

Use of the electrochemical sensor array to identify unknown bacteria in clinical urine specimens would be greatly simplified by including all relevant detector probes in a single hybridization step. However, probe-probe and probe-target interactions could potentially reduce the sensitivity and specificity of the sensor when a 16S rRNA target is hybridized with mixtures of detector probes. For this reason, we systematically examined the effect of probe-target hybridization using mixtures of detector probes on signal intensity. A representative experiment is shown in FIG. 8 in which *Enterococcal* 16S rRNA was hybridized with a mixture of the EF165D and EC393D detector probes versus hybridization with the EF165D detector probe alone. When the target-detector probe hybrids were applied to sensors functionalized with the EF207C capture probe, there was no significant difference in signal intensity between the results generated with the EF165D+EC393D detector probe mixture and results generated with the EF16SD detector probe alone. Hybridization of these same detector and capture probe mixtures with *E. coli* 16S rRNA resulted in no significant signal, indicating that sensor specificity was retained despite hybridization of the *E. coli* 16S rRNA target with the *E. coli*-specific EC393D detector probe, Likewise, no loss of sensitivity or specificity was observed with other 2-detector probe combinations including EC393D & PM147D, EC393D & KE393D, PA68D & EF165D. Similar results were obtained using a 3-detector-probe cocktail (EC393D, PM147D, & KE393D) and a 5-detector-probe cocktail (EC393D, PM147D, KE393D, PA68D, & EF165D), showing no significant reduction in electrochemical signal output compared to experiments with single detector probes Sensor Validation Using Control Bacterial Strains A panel of well-characterized bacterial strains from the American Type Culture Collection was tested to validate the species specificity of the "UTI Chip" using a 7-detector-probe mixture (UNI7511D, EB1141D, EC399D, PM153D, KE399D, PA74D, & EF171 D) The UNI782C capture probe detected all bacterial uropathogens tested. As expected, the EB1172C capture probe was positive for all members of the family Enterobacteriaceae tested and negative for *P. aeruginosa* and *E. faecalis*. The KE434C capture probe was positive for all Enterobacteriaceae except *E. coli*. The only species-specific capture probes positive for *E. coli* was EC434C, Likewise the PM188C, PA111C and EF207C capture probes were specific for *P. mirabilis, P. aeruginosa,* and *E. faecalis*, respectively. FIG. 13 shows the results when the lysate of *K. pneumonia* strain 13883 was hybridized with the detector probe mixture and applied to the UTI Chip. As expected, *K. pneumoniae* 16S RNA was detected by sensors using capture probes UNI782C, EB1176C. and KE434C, but not those using capture probes EC434C, PA102C, PM187C, and EF207C.

Statistical Analysis

Figure 14:
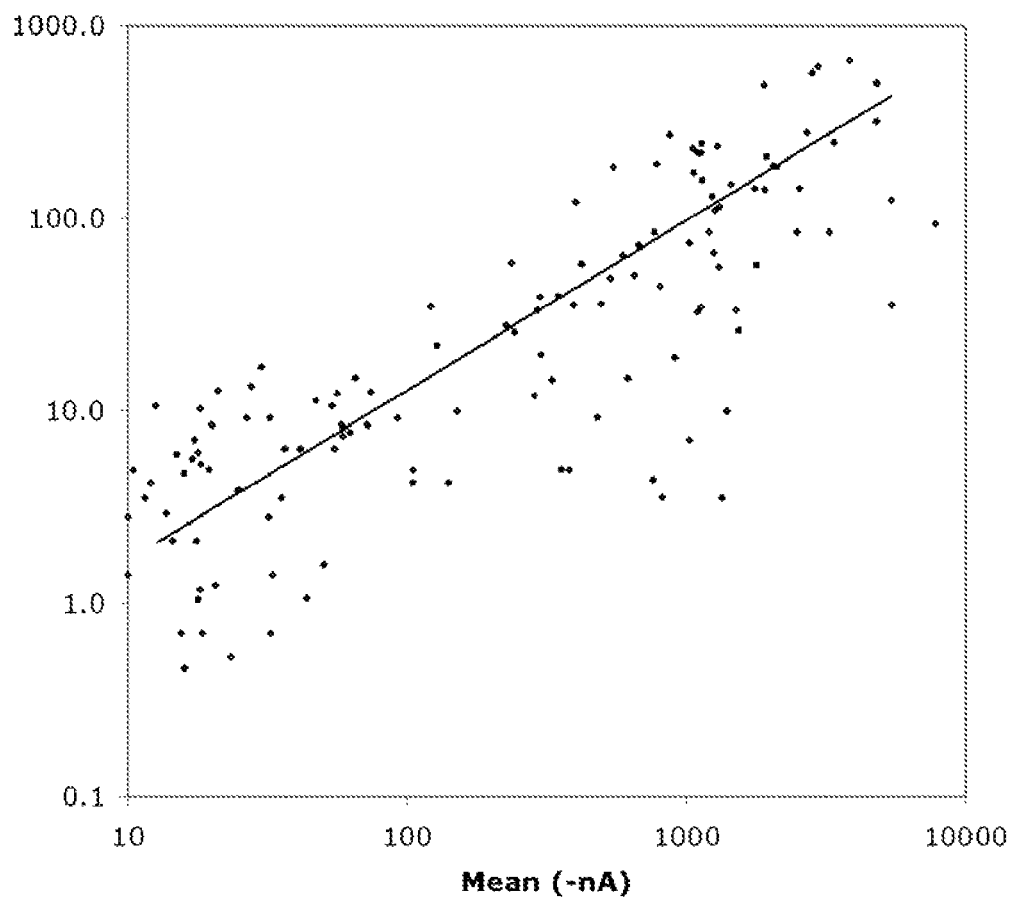
FIG. 14. Effect of signal intensity on standard deviation. The mean signal intensity and standard deviation for all 164 experiments reported in this study were performed in duplicate and included in this figure. There was a linear correlation between the mean signal intensity and the standard deviation. The duplicate residual errors were found to have a log normal distribution, as suggested by the clustering of the data points in this figure about the best fit line. The standard deviation of the duplicates was roughly constant at a value of 0.062 log units.

Variance of signal intensity measurements obtained using the electrochemical sensor was determined by comparing the results from duplicate experiments. As shown in FIG. 14, the standard deviation was found to correlate with the mean signal intensity. As reported in a previous study,[16] duplicate residual errors were found to have a log normal distribution. Sensor specific error was determined by pooling the residual errors for all experiments involving each of the bacterial species tested, and varied from 0.040 log units for *E. faecalis* to 0.105 log units for *K. oxytoca* (Table 10). An overall estimate of the standard deviation was 0.062 log units, obtained by pooling the residual errors for all 164 experiments reported in this study. Significant differences between results were determined by comparing mean log current output +/−5 standard deviations (0.31 log units), as a relatively conservative test of statistical significance.

TABLE 10

Effect of bacterial species on signal variance

| Species | Duplicate experiments (N) | Standard deviation about mean (log units) |
|---|---|---|
| *Citrobacter freundii* | 7 | .049 |
| *Enterobacter aerogenes* | 7 | .081 |
| *Enterobacter cloacae* | 7 | .084 |
| *Enterococcus faecalis* | 40 | .040 |

TABLE 10-continued

Effect of bacterial species on signal variance

| Species | Duplicate experiments (N) | Standard deviation about mean (log units) |
|---|---|---|
| Escherichia coli | 41 | .041 |
| Klebsiella oxytoca | 7 | .105 |
| Klebsiella pneumoniae | 11 | .063 |
| Proteus mirabilis | 13 | .099 |
| Pseudomonas aeruginosa | 13 | .077 |
| Pooled results | 164 | .062 |

Discussion

The sensor assay system for direct electrochemical detection of the bacteria that cause urinary tract infection relies on efficient lysis and release of target 16S rRNA molecules. While alkaline lysis was sufficient for release of 16S rRNA from Gram-negative bacteria this approach did not work well for the *Enterococcus*. To break down the thicker cell wall of the Gram-positive uropathogens, we developed a rapid two-step lysis method involving a detergent-enzyme treatment, followed by alkaline lysis. The detection system involves oligonucleotide capture and detector probes that bind to ribosomal RNA present in high copy number within the bacterial cytoplasm. The biotinylated capture probe anchors the target 16S rRNA molecule to the streptavidin-coated sensor surface, while the fluorescein modification on the detector probe mediates binding of the anti-fluorescein conjugated horseradish peroxidase reporter enzyme.

We found that current output was highly dependent on the distance between the capture and detector probe hybridization sites, and on the location of the fluorescein modification on the detector probe.

A fundamental difference between Gram-negative and -positive bacteria is the thicker peptidoglycan cell wall of Gram-positive organisms, We had previously observed that treatment with sodium hydroxide is an efficient lysis method for release of 16S rRNA from Gram-negative, but not Gram-positive, uropathogens.[16] This problem in the critical first step of the electrochemical sensor assay system seriously limited its effectiveness for detection of uropathogens, because Gram-positive enterococci are frequent urine culture isolates. We found that pretreatment with the cell-wall active enzyme, lysozyme, was found to greatly enhance alkaline lysis. In this study, we demonstrate that a combination of a non-denaturing detergent (Triton X-100) with lysozyme followed by alkaline treatment (NaOH) yielded optimal electrochemical signals for detection of the *Enterococcus*. The Triton X-100 may have additional beneficial effects, such as removal of ribosomal proteins from the 16S rRNA target molecule. Other reagents, such as the denaturing detergent sodium dodecyl sulfate (SOS), were examined and found not to be useful. One problem with SDS may be denaturation of proteins, especially the streptavidin on the sensor surface. The concentration of Triton X-100 (0.1%) was found to be important; higher Triton X-100 concentrations resulted in loss of surface tension when the whole cell lysate was applied to the sensor surface, resulting in cross-contamination of adjacent sensors within the array. The total lysis time of 10-minute is a significant improvement over prior reports of lysis of Gram-positive organisms with lysozyme, which may take up to 1 hour incubation time.[20] This two-step lysis strategy was also effective against Gram-negative bacteria, indicating its potential as a universal bacterial lysis method.

The results presented here demonstrate that maximal signal intensity requires capture and detector probes without a gap between their 16S rRNA hybridization sites. In a previous study, species-specific capture and detector probes were designed with a 6-nucleotide gap between their hybridization sites.[16] However, we noted that the juxtaposed hybridization sites of the capture-detector probe pair (UNI) used to detect all bacterial 16S rRNA molecules consistently yielded higher signals than the species-specific probe pairs. For this reason, we tested the hypothesis that the distance between the capture and detector probe hybridization sites on the 16S rRNA target affects electrochemical signal intensity. For gaps $\leqq 6$ nucleotides, there was a strong correlation between signal intensity and the number of nucleotides between the capture and detector probe hybridization sites (FIG. 11). A variety of different bacterial species-specific probe pairs without a gap between the capture and detector probe hybridization sites consistently produced higher current outputs using the electrochemical sensor than those with 6 nucleotide gaps (Table 8). This finding was independent of which part of the 16S rRNA molecule was targeted by the probe pairs; capture and detector probe pairs binding to adjacent segments of helices 6, 10, 18, and 37 of the 16S rRNA molecule of *P. aeruginosa, P. mirabilis, E. coli*, and *K. pneumoniae*, respectively, all outperformed similar probe pairs that differed only in the detector probe hybridization site.

Cooperative interactions between probes hybridizing to adjacent sites on nucleic acid targets have previously been reported.[21-24] Flow cytometric measurement of fluorescein-modified oligonucleotide probe hybridization to *E. coli* 16S rRNA revealed significant signal enhancement by addition of unlabeled "helper" probes binding to adjacent sites.[21] Using an electrochemical sensor assay similar to ours, signal intensity was enhanced using a helper oligonucleotide binding to the region between the capture and detector probe hybridization sites of rRNA from a marine dinoflagellate.[22] Gaps as short as one nucleotide between the hybridization sites of the helper oligonucleotide and biotinylated capture probe reduced detection of a double-stranded PCR product using a streptavidin coated BIAcore sensor.[23] Oligonucleotide binding to immediately adjacent sites creates a base pair stacking interaction that stabilizes hybridization.

The beneficial base pair stacking effect may also relate to the effect of the location of the detector probe fluorescein modification on signal intensity. Use of 3'-fluorescein modified detector probes resulted in higher electrochemical sensor current output than the same detector probes modified at the 5' position. The effect of fluorescein modification location on signal strength was generalizable across a broad range of bacterial 16S rRNA molecules and probe hybridization sites (Table 9). For detection of enterococcal 16S rRNA, the increase in signal intensity produced by moving the fluorescein modification from the 5' to 3' position on the detector probe was additive to the effect of eliminating the interprobe hybridization gap (FIG. 12A). Several explanations for the positional effect of detector probe fluorescein modification are possible. Because the 5' end of the detector probe abuts the 3' end of the capture probe, when both probes are bound to the 16S rRNA target, a 5' fluorescein modification would sterically disrupt base pair stacking between the probes. Another explanation could involve the interaction of the fluorescein with the pocket of the antibody-binding site on the anti-fluorescein Fab fragment. Depending on the depth of the pocket, the high affinity interaction of fluorescein with the Fab fragment could require destabilization of target-probe hybridization of the 5'-end of the detector probe, again disrupting the beneficial interprobe base pair stacking effect.

The disruption of interprobe base pair stacking by the 5' fluorescein modification of detector probe EF171D 5° F. probe (no interprobe gap) may explain why the signal output using that probe is roughly equal to that using the 3'-fluorescein modified detector probe EF165D 3° F. with the 6 nucleotide interprobe gap (FIGS. 12A-B).

The increases in signal intensity from eliminating the interprobe hybridization site gap and from moving the detector probe fluorescein modification to the 3' position resulted in a dramatic improvement in sensitivity of bacterial detection using the electrochemical sensor. As shown in FIG. 12, the sensitivity limit for detection improved 24-25 fold in experiments involving serial five-fold dilutions of *E. faecalis* and *E. coli*. This result confirms that increases in current output using the electrochemical sensor translate to improved sensitivity. The shape of the curves illustrated in FIG. 12 indicates that the log of signal intensity varies as a linear function of the log of target concentration. In other words, there is an exponential relationship between bacterial target concentration and signal intensity. Increases in bacterial concentration should yield increases in 16S rRNA target concentration, probe-target complexes, and ultimately horseradish peroxidase molecules on the sensor surface. However, the efficiency of these hybridization and binding steps would affect the relationship between bacterial target concentration and current output, as evidenced by the earlier and steeper increase obtained using the 3'-fluorescein labeled detector probe EF171D than that slope obtained using the 5'-fluorescein labeled detector probe EF165D in FIG. 12A. Assuming known relationship constants for the same set of capture and detector probe and reagent concentrations, it should be possible to predict bacterial target concentration using the electrochemical sensor by incorporating an internal standard into the sensor array assay.

The findings reported here demonstrate the feasibility of using mixtures of detector probes as a common reagent for species-specific detection of uropathogens using an electrochemical sensor array. In previous studies, detector probes were added separately to the bacterial lysate for hybridization prior to deposition onto the surface of individual sensors, each coated with a different capture probe.[16] That is, a separate detector probe hybridization was performed for each capture probe. Because the capture probes are designed to hybridize to different areas of the 16S rRNA target, a 'universal' detector probe for each of the capture probes was not possible. We examined the possibility of simplifying the detector probe hybridization step in a series of experiments measuring the effect of hybridizing the 16S rRNA target with a mixture of detector probes. As shown in FIG. 8, a representative experiment involving two detector probes, mixtures of detector probes did not reduce the intensity of the positive signal. Our results also demonstrated that detector probe mixtures did not increase background signal, indicating that the sequence of the capture probe alone was adequate to ensure specificity. The use of a probe mixture greatly simplifies the detection protocol when faced with a specimen containing unknown targets because the 'universal detector probe mixture' can be used for urine specimens containing unknown bacteria. The performance of a detector probe mixture is illustrated in FIG. 13 in which a 'UTI Chip' array, containing sensors coated with different capture probes, correctly identified 16S rRNA from a well-characterized ATCC strain of *K. pneumoniae*.

REFERENCES

1. See reference 8 of Example 1
2. See reference 16 of Example 1
3. See reference 18 of Example 1
4. See reference 33 of Example 1
5. See reference 47 of Example 1
6. See reference 19 of Example 1
7. See reference 20 of Example 1
8. See reference 17 of Example 1
9. See reference 5 of Example 1
10. See reference 7 of Example 1
11. See reference 46 of Example 1
12. See reference 50 of Example 1
13. See reference 11 of Example 1
14. See reference 27 of Example 1
15. See reference 42 of Example 1
16. Liao J C et al., J Clin Microbiol 2006, 44.561-570
17. Brosius J et al., Proc Natl Acad Sci USA 1978, 75:4801-4805
18. Summanen P H et al., J Clin Microbiol 2005, 43:4455-4459
19. See reference 1 of Example 2
20. Chassy S M, Giuffrida A, Appl Environ Microbiol 1980, 39:153-158
21. Fuchs B M et al., Appl Environ Microbiol 2000, 66:3603-3607
22. See reference 7 of Example 2
23. O'Meara D et al. Anal Biochem 1998, 255:195-203
24. Niemeyer C M et al., Angew Chem Int Ed 1998, 37:2265-2268

Example 4

Development of an Assay for Antibiotic Resistance

This example demonstrates the feasibility of using the 16S-rRNA electrochemical sensor assay to measure the phenotypic response of uropathogens to antibiotics. Antibiotic resistance mechanisms of uropathogens are diverse. For this reason, development of reliable and comprehensive genotypic tests for antibiotic resistance would pose a potentially insurmountable challenge. By contrast, a phenotypic assay, such as measurement of 16S rRNA levels using the electrochemical sensor, would be applicable to a broad array of organisms and antibiotics and would remain accurate, even as new antibiotic resistance mechanisms emerge.

The 16S rRNA level is an excellent surrogate marker for the physiologic state of bacterial cells (3). The method takes advantage of the strong correlation between ribosome levels and growth rate, ribosome levels increase rapidly when organisms are placed into growth medium (4, 5). Antibiotics adversely affect bacterial growth and physiology by interfering with the function of a variety of targets. The effect of antibiotics on 16S rRNA levels has been determined for some bacteria and some antibiotics (1, 2).

Figure 15:
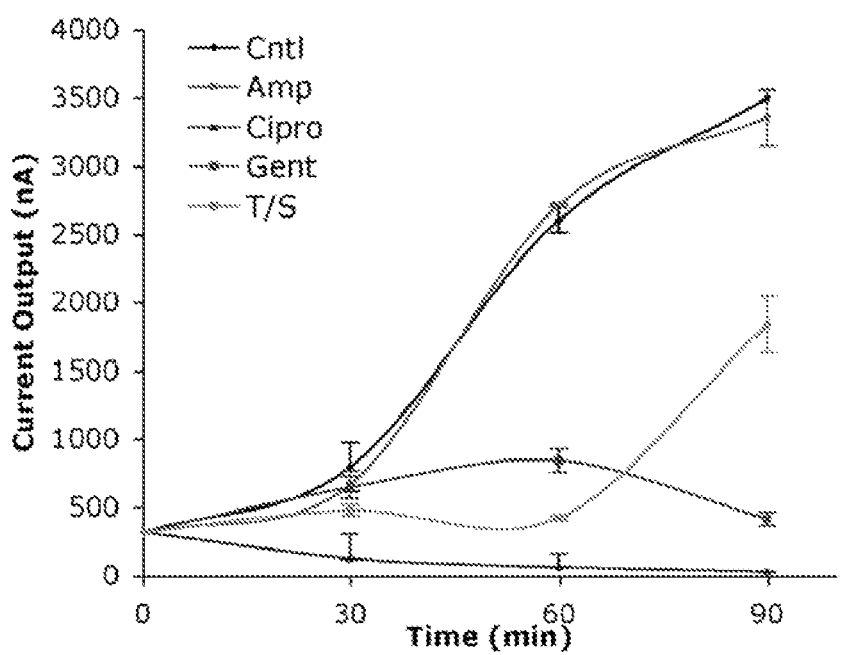
FIG. 15. Electrochemical signal of an ampicillin-resistant *E. coli* uropathogen in response to antibiotics. *E. coli* clinical urine isolates with a variety of antibiotic resistance profiles were inoculated into growth medium at 37° C. with and without relevant antibiotics. Biosensor assays and colony forming units (CFU) measurements were performed at 30, 60, and 90 min after inoculation. In each case, there was a significant difference in biosensor current output between antibiotic resistance and susceptibility within 60 min.

*E. coli* clinical urine isolates with a variety of antibiotic resistance profiles were inoculated into growth medium at 37° C. with and without relevant antibiotics. Biosensor assays and colony forming units (CFU) measurements were performed at 30, 60, and 90 min after inoculation. FIG. 15 illustrates the results of a representative study of an ampicillin-resistant E. coli uropathogen. In each case, there was a significant difference in biosensor current output between antibiotic resistance and susceptibility within 60 min.

The next question was whether the assay could be performed directly on bacteria in clinical urine specimens as a rapid determination of antibiotic susceptibility profile. We have performed a pilot antibiotic susceptibility study of blinded clinical urine specimens obtained from patients suspected to have urinary tract infection. The concentration of bacteria in each specimen was estimated using a rapid ATP bioluminescence assay to determine the amount of urine needed to achieve an inoculum of $10^5$ CFU/ml in samples of growth medium with and without the following six antibiotics: ampicillin, cephalothin, ciprofloxacin, gentamicin, nitrofurantoin, and trimethoprim/sulfamethoxazole (Tmp/Smx). CFU measurements and biosensor assays using the universal bacterial probe pair were performed after incubation at 37° C. for 120 min. To date we have tested 14 specimens containing a variety of uropathogens including E Coli, K. pneumoniae, P. mirabilis, C. freundii, and C. koseri. Comparison of the biosensor results to those obtained by the UCLA Clinical Microbiology Laboratory found an overall accuracy rate of 80/82=983% Two failures in the antimicrobial susceptibility biosensor assay occurred: In one case an organism appeared to be falsely susceptible to nitrofurantoin and another was falsely resistant to tmp/smx. These data suggest that the biosensor can be used to rapidly and reliably determine the antibiotic susceptibility profile of uropathogens in clinical specimens.

| | Antimicrobial Susceptibility Results using the 16S rRNA Biosensor* | |
|---|---|---|
| Antibiotic | Susceptible Organisms (# Correct/Total = % Correct) | Resistant Organisms (# Correct/Total = % Correct) |
| Ampicillin | 7/7 = 100% | 7/7 = 100% |
| Gentamicin | 12/12 = 100% | 1/1 = 100% |
| Cephazolin | 11/11 = 100% | 3/3 = 100% |
| Ciprofloxacin | 11/11 = 100% | 3/3 = 100% |
| Nitrofurantoin | 12/12 = 100% | 0/1 = 0% |
| Tmp/Smx | 9/10 = 90% | 4/4 = 100% |

*UCLA Clinical Microbiology Laboratory results were used as the gold standard. Gentamicin and nitrofurantoin totals do not add up to 14 because 1 result in each case was "intermediate" susceptibility.
1. Cangelosi, G. A., and W. H. Brabant. 1997. J Bacteriol 179: 4457-63.
2. Cangelosi, G. A. et al. 1996. Antimicrob Agents Chemother 40: 1790-5.
3. Condon, C. et al. 1995. Microbiol Rev 59: 623-45.
4. Gausing, K. 1980, in E. coli. In G. R. C. G. Chambliss et al. (ed.), Ribosomes: structure, function, and genetics. University Park Press, Baltimore.
5. Schaechter, M. et al. 1958. J Gen Microbiol 19: 592-606.

Example 5

Short Oligonucleotide Probes Useful at Ambient Temperature

This example examines oligonucleotide probe pairs ranging from 10-22 nucleotides in length designed to distinguish 7 groups of urinary tract pathogens. Probe pairs as short as 10 nucleotides in length were able to produce a significant electrochemical signal when hybridization was performed at ambient temperature. Signal intensity was found to vary with probe length and hybridization location, and correlated with the base-stacking method of calculating meting temperature. For example, changing the length of the E. coli-specific probe from 35 nucleotides to 15 nucleotides caused a change in mean current from 184 to 1605 negative nanoamperes, an eight fold improvement in signal intensity. Targeting the highly accessible and sequence variable helix 18 of the E. coli 16S rRNA allowed us to develop probe pairs as short as 15 nucleotides in length that retained both species specificity and high current output. The sensitivity of the E. coli-specific 15mer probe pairs was approximately 173 cells, demonstrating attomolar (8.8×10-16 M) sensitivity for the target 16S rRNA molecules. This example describes short oligonucleotide probe pairs with attomolar sensitivity for species-specific identification of uropathogens at ambient temperature using an electrochemical sensor. Molecular identification of bacteria at ambient temperature will be advantageous for use with a point-of-care detection device.

Bacterial strains and cultivation. The following American Type Culture Collection (ATCC) strains were obtained from the UCLA Clinical Microbiology Laboratory: Escherichia coli strain 35218, Klebsiella pneumoniae strain 13883, Klebsiella oxytoca strain 49131, Enterobacter aerogenes strain 13048, Enterobacter cloacae strain 13047, Proteus mirabilis strain 12453, Pseudomonas aeruginosa strain 10145, Citrobacter freundii strain 8090, and Enterococcus faecalis strain 49532. Additional strains of uropathogenic bacteria were obtained from the UCLA Uropathogen Specimen Bank: E. coli strain Eo103, K. pneumoniae strain Kp114 and Kp101, P. mirabilis strain Pm278 and Pm193, P. aeruginosa strain Pa3, E. faecalis strain Eo111, Enterobacter aerogenes Ea203, and Citrobacter freundii Cf364. Isolation of uropathogens from clinical urine specimens was approved by the UCLA and VA Greater Los Angeles Healthcare System institutional Review Boards. The identity of all clinical strains was determined by standard biochemical assays and verified by 16S rRNA gene sequencing. The 16S rRNA genes were PCR amplified with universal primers 8UA and 1485B. (2) The amplified product was purified by using the QIAquick PCR purification kit (QIAGEN, Inc., Chatsworth, Calif.) and directly sequenced using primer pairs 8UA/907B and 774A/1485B as described previously. (11) DNA sequencing was performed at the W, M. Keck Foundation Biotechnology Resource Laboratory (New Haven, Conn.). Isolates were inoculated into Brucella broth with 15% glycerol (BBL, Maryland) and were stored at −70° C. All experiments reported here involved bacteria grown overnight in Bacto™ Tryptic Soy Broth (TSB). Becton, Dickinson (Sparks, Md.), inoculated into TSB and grown to logarithmic phase as measured by $OD_{600}$. Concentration of the logarithmic phase specimens was determined by serial plating, typically yielding $10^7$-$10^8$ bacteria/ml.

Oligonucleotide probe design. Oligonucleotide probes were synthesized by MWG Biotech (High Point, N.C.) and Sigma (ST. Louis, Mo.). Capture probes are synthesized with a 5' biotin modification. Detector probes were synthesized with 3'-fluorescein modifications. Oligonucleotide probe pairs were designed to hybridize with species-specific regions of the 16S rRNA molecules of E. coli, E. faecalis, P. mirabilis, K. pneumoniae, C. freundii, and P. aeruginosa. Oligonucleotides were also designed as capture and detector probes for the family Enterobacteriaceae, and as universal bacterial probes. The sequences of ail oligonucleotide probes used in this study are shown in Table 11.

TABLE 11

Sequences of Oligonucleotide Probes Used in this Example

Probe   Designation (length)   Sequence (5'-3')

*Escherichia coli* (EC) Probe Pairs

| Capture EC435C (10 mer) | 5'-TACTCCCTTC-3' | (SEQ ID NO. 96) |
| Detector EC425D (10 mer) | 5'-CTCCCCGCTG-3' | (SEQ ID NO. 97) |
| Capture EC436C (10 mer) | 5'-TTACTCCCTT-3' | (SEQ ID NO: 98) |
| Detector EC426D (10 mer) | 5'-CCTCCCCGCT-3' | (SEQ ID NO: 99) |
| Capture EC437C (10 mer) | 5'-TTTACTCCCT-3' | (SEQ ID NO: 100) |
| Detector EC427 (10 mer) | 5'-TCCTCCCCGC-3' | (SEQ ID NO: 101) |
| Capture EC438C (10 mer) | 5'-CTTTACTCCC-3' | (SEQ ID NO: 102) |
| Detector EC428D (10 mer) | 5'-TTCCTCCCCG-3' | (SEQ ID NO: 103) |
| Capture EC439C (10 mer) | 5'-ACTTTACTCC-3' | (SEQ ID NO: 104) |
| Detector EC429D (10 mer) | 5'-CTTCCTCCCC-3' | (SEQ ID NO: 105) |
| Capture EC440C (10 mer) | 5'-AACTTTACTC-3' | (SEQ ID NO: 106) |
| Detector EC430D (10 mer) | 5'-CCTTCCTCCC-3' | (SEQ ID NO: 107) |
| Capture EC441C (10 mer) | 5'-TAACTTTACT-3' | (SEQ ID NO: 108) |
| Detector EC431D (10 mer) | 5'-CCCTTCCTCC-3' | (SEQ ID NO: 109) |
| Capture EC442C (10 mer) | 5'-TTAACTTTAC-3' | (SEQ ID NO: 110) |
| Detector EC432D (10 mer) | 5'-TCCCTTCCTC-3' | (SEQ ID NO: 111) |
| Capture EC443C (10 mer) | 5'-ATTAACTTTA-3' | (SEQ ID NO: 112) |
| Detector EC433D (10 mer) | 5'-CTCCCTTCCT-3' | (SEQ ID NO: 113) |
| Capture EC444C (10 mer) | 5'-TATTAACTTT-3' | (SEQ ID NO: 114) |
| Detector EC434D (10 mer) | 5'-ACTCCCTTCC-3' | (SEQ ID NO: 115) |
| Capture EC429C (11 mer) | 5'-AACTTTACTCC-3' | (SEQ ID NO: 116) |
| Detector EC428D (11 mer) | 5'-CTTCCTCCCCG-3' | (SEQ ID NO: 117) |
| Capture EC439C (12 mer) | 5'-TAACTTTACTCC-3' | (SEQ ID NO: 118) |
| Detector EC427D (12 mer) | 5'-CTTCCTCCCCGC-3' | (SEQ ID NO: 119) |
| Capture EC439C (13 mer) | 5'-TTAACTTTACTCC-3' | (SEQ ID NO: 120) |
| Detector EC426D (13 mer) | 5'-CTTCCTCCCCGCT-3' | (SEQ ID NO: 121) |
| Capture EC439C (14 mer) | 5'-ATTAACTTTACTCC-3' | (SEQ ID NO: 122) |
| Detector EC425D (14 mer) | 5'-CTTCCTCCCCGCTG-3' | (SEQ ID NO: 123) |
| Capture EC439C (15 mer) | 5'-TATTAACTTTACTCC-3' | (SEQ ID NO: 44) |
| Detector EC424D (15 mer) | 5'-CTTCCTCCCCGCTGA-3' | (SEQ ID NO: 45) |
| Capture EC439C (20 mer) | 5'-AAAGGTATTAACTTTACTCC-3' | (SEQ ID NO: 124) |
| Detector EC419D (20 mer) | 5'-CTTCCTCCCCGCTGAAAGTA-3' | (SEQ ID NO: 125) |
| Capture EC439C (25 mer) | 5'-TGAGCAAAGGTATTAACTTTACTCC-3' | (SEQ ID NO: 126) |
| Detector EC414D (25 mer) | 5'-CTTCCCTGAAAGTACTTTACAACCC-3' | (SEQ ID NO: 127) |
| Capture EC439C (30 mer) | 5'-GTCAATGAGCAAAGGTATTAACTTTACTCC-3' | (SEQ ID NO: 128) |
| Detector EC409D (30 mer) | 5'-CTTCCCTGAAAGTACTTTACAACCCGAAGG-3' | (SEQ ID NO: 129) |
| Capture EC439C (35 mer) | 5'-TGAGCGTCAATGAGCAAAGGTATTAACTTTACTCC-3' | (SEQ ID NO: 130) |
| Detector EC404D (35 mer) | 5'-CTTCCCTGAAAGTACTTTACAACCCGAAGGCCTTC-3' | (SEQ ID NO: 131) |

*Proteus mirabilis* (PM) Probe Pairs

| Capture PM434C (12 mer) | 5'-TTATCACCTTCC-3' | (SEQ ID NO: 132) |
| Detector PM422D (12 mer) | 5'-TCCCCGCTGAAA-3' | (SEQ ID NO: 133) |
| Capture PM435C (12 mer) | 5'-CTTATCACCTTC-3' | (SEQ ID NO: 134) |
| Detector PM423D (12 mer) | 5'-CTCCCCGCTGAA-3' | (SEQ ID NO: 135) |
| Capture PM436C (12 mer) | 5'-CCTTATCACCTT-3' | (SEQ ID NO: 136) |
| Detector PM424D (12 mer) | 5'-CCTCCCCGCTGA-3' | (SEQ ID NO: 137) |
| Capture PM437C (11 mer) | 5'-CCTTATCACCT-3' | (SEQ ID NO: 138) |
| Detector PM426D (11 mer) | 5'-TCCTCCCCGCT-3' | (SEQ ID NO: 139) |
| Capture PM438C (12 mer) | 5'-AACCTTATCACC-3' | (SEQ ID NO: 140) |
| Detector PM426D (12 mer) | 5'-TTCCTCCCCGCT-3' | (SEQ ID NO: 141) |

TABLE 11-continued

Sequences of Oligonucleotide Probes Used in this Example

| Probe | Designation (length) | Sequence (5'-3') | |
|---|---|---|---|
| Capture | PM439C (13 mer) | 5'-TTAACCTTATCAC-3' | (SEQ ID NO: 142) |
| Detector | PM426D (13 mer) | 5'-CTTCCTCCCCGCT-3' | (SEQ ID NO: 143) |
| Capture | PM440C (13 mer) | 5'-ATTAACCTTATCA-3' | (SEQ ID NO: 144) |
| Detector | PM427D (13 mer) | 5'-CCTTCCTCCCCGC-3' | (SEQ ID NO: 145) |
| Capture | PM197C (21 mer) | 5'-CATCCGATAGTGCAAGGTCCG-3' | (SEQ ID NO: 46) |
| Detector | PM176D (21 mer) | 5'-AAGAGCCCCTGCTTTGGTCCG-3' | (SEQ ID NO: 47) |

*Klebsiella* pneumoniae (KP) Probe Pairs

| | | | |
|---|---|---|---|
| Capture | KP434C (9 mer) | 5'-(ACT)CGCCTTCC-3' | |
| Detector | KP425D (9 mer) | 5'-TCCCCGCTG-3' | |
| Capture | KP435C (11 mer) | 5'-T(TC)A(ACT)CGCCTTC-3' | (SEQ ID NO: 146) |
| Detector | KP424D (11 mer) | 5'-CTCCCCGCTGA-3' | (SEQ ID NO: 147) |
| Capture | KP436C (11 mer) | 5'-CT(TC)A(ACT)CGCCTT-3' | (SEQ iD NO: 48) |
| Detector | KP425D (11 mer) | 5'-CCTCCCCGCTG-3' | (SEQ ID NO: 49) |
| Capture | KP437C (10 mer) | 5'-CT(TC)A(ACT)CGCCT-3' | (SEQ ID NO: 148) |
| Detector | KP427D (10 mer) | 5'-TCCTCCCCGC-3' | (SEQ ID NO: 149) |
| Capture | KP438C (11 mer) | 5'-CCT(TC)A(ACT)CGCC-3' | (SEQ ID NO: 150) |
| Detector | KP428D (10 mer) | 5'-TTCCTCCCCG-3' | (SEQ ID NO: 151) |
| Capture | KP439C (11 mer) | 5'-AACCT(TC)A(ACT)CGC-3' | (SEQ ID NO: 152) |
| Detector | KP428D (11 mer) | 5'-CTTCCTCCCCG-3' | (SEQ ID NO: 153) |
| Capture | KP440C (12 mer) | 5'-TTAACCT(TC)A(ACT)CG-3' | (SEQ ID NO: 154) |
| Detector | KP428D (12 mer) | 5'-CCTTCCTCCCCG-3' | (SEQ ID NO: 155) |

*Pseudomonas aeruginosa* (PA) Probe Pairs

| | | | |
|---|---|---|---|
| Capture | PA122C (11 mer) | 5'-CTTTCTCCCTC-3' | (SEQ ID NO: 156) |
| Detector | PA112D (11 mer) | 5'-AGGACGTATGC-3' | (SEQ ID NO: 157) |
| Capture | PA122C (12 mer) | 5'-ACTTTCTCCCTC-3' | (SEQ ID NO: 158) |
| Detector | PA110D (12 mer) | 5'-AGGACGTATGCG-3' | (SEQ ID NO: 159) |
| Capture | PA122C (13 mer) | 5'-CACTTTCTCCCTC-3' | (SEQ ID NO: 160) |
| Detector | PA109D (13 mer) | 5'-AGGACGTATGCGG-3' | (SEQ ID NO: 161) |
| Capture | PA122C (15 mer) | 5'-CCACTTTCTCCCTC-3' | (SEQ ID NO: 50) |
| Detector | PA107D (15 mer) | 5'-AGGACGTATGCGGTA-3' | (SEQ ID NO: 51) |
| Capture | PA122C (20 mer) | 5'-GATCCCCCACTTTCTCCCTC-3' | (SEQ ID NO: 162) |
| Detector | PA102D (20 mer) | 5'-AGGACGTATGCGGTATTAGC-3' | (SEQ ID NO: 163) |
| Capture | PA836C (15 mer) | 5'-GCCACTAAGATCTCA-3' | (SEQ ID NO: 164) |
| Detector | PAS21D (15 mer) | 5'-AGGATCCCAACGGCT-3' | (SEQ ID NO: 165) |
| Capture | PA836C (20 mer) | 5'-GCTGCGCCACTAAGATCTCA-3' | (SEQ ID NO: 166) |
| Detector | PA816D (20 mer) | 5'-AGGATCCCAACGGCTAGTCG-3' | (SEQ ID NO: 167) |

*Enterococcus* spp. (EF) Probe Pair

| | | | |
|---|---|---|---|
| Capture | EF187C (20 mer) | 5'-ACCGCGGGTCCATCCATCAG-3' | (SEQ ID NO: 52) |
| Detector | EF167D (20 mer) | 5'-CGACACCCGAAAGCGCCTTT-3' | (SEQ ID NO: 53) |

Enterobacteriaceae (EB) Probe Pair

| | | | |
|---|---|---|---|
| Capture | EB1275C (23 mer) | 5'-ACTTTATGAGGTCCGCTTGCTCT-3' | (SEQ ID NO: 54) |
| Detector | EB1252D (23 mer) | 5'-CGCGAGGTCGCCTTCCTTTGTAT-3, | (SEQ ID NO: 55) |

Universal Bacterial (UNI) Probe Pair

| | | | |
|---|---|---|---|
| Capture | UNI782C (19 mer) | 5'-ACGGCGTGGACTACCAGGG-3' | (SEQ ID NO: 56) |
| Detector | UNI763D (19 mer) | 5'-TATCTAATCCTGTTTGCTC-3' | (SEQ ID NO: 57) |

TABLE 12

Sequences of Oligonucleotide Probes Used in the 16 Sensor Array

| Probe | Position[a] (length) | Sequence (5'-3') | |
|---|---|---|---|
| *Escherichia coli* (EC) | | | |
| Capture EC439C | (15 mer) | 5'-TATTAACTTTAGTCG-3' | (SEQ ID NO: 44) |
| Detector EC424D | (15 mer) | 5'-CTTCCTCCCCGCTGA-3' | (SEQ ID NO: 45) |
| *Proteus mirabilis* (PM) | | | |
| Capture PM197C | (21 mer) | 5'-CATCCGATAGTGCAAGGTCCG-3' | (SEQ ID NO: 46) |
| Detector PM176D | (21 mer) | 5'-AAGAGCCCCTGCTTTGGTCCG-3' | (SEQ ID NO: 47) |
| *Klebsiella poeumoniae* (KP) | | | |
| Capture KP436C | (11 mer) | 5'-CT(TC)A(ACT)CGCCTT-3' | (SEQ ID NO: 48) |
| Detector KP425D | (11 mer) | 5'-CCTCCCCGCTG-3' | (SEQ ID NO: 49) |
| *Pseudomonas aeruginosa* (PA) | | | |
| Capture PA122C | (15 mer) | 5'-CCCACTTTCTCCCTC-3' | (SEQ ID NO: 50) |
| Detector PA107D | (15 mer) | 5'-AGGACGTATGCGGTA-3' | (SEQ ID NO: 51) |
| *Enterococcus spp.* (EF) | | | |
| Capture EF187C | (20 mer) | 5'-ACCGCGGGTCCATCCATCAG-3' | (SEQ ID NO: 52) |
| Detector EF107D | (20 mer) | 5'-CGACACCCGAAAGCGCCTTT-3' | (SEQ ID NO: 53) |
| *Enterobacteriaceae* (EB) | | | |
| Capture EB1275C | (23 mer) | 5'-ACTTTATCAGCTCCGCTTGCTCT-3' | (SEQ ID NO: 54) |
| Detector EB1252D | (23 mer) | 5'-CGCGAGGTCGCCTTCCTTTGTAT-3' | (SEQ ID NO: 55) |
| Universal Bacterial (UNI) | | | |
| Capture UNI782C | (19 mer) | 5'-ACGGCGTGGACTACCAGGG-3' | (SEQ ID NO: 56) |
| Detector UNI763D | (19 mer) | 5'-TATCTAATCCTGTTTGCTC-3' | (SEQ ID NO: 57) |

TABLE 13

Species specificity of probe pairs used with electrochemical sensor array.

| Capture Probe detected[a] | Detector Probe | Species detected[a] | Species not |
|---|---|---|---|
| EC439C (15 mer) | EC424D (15 mer) | Ec | Ea, Ef, Kp, Pa*, Pm |
| PM197C (21 mer) | PM176D (21 mer) | Pm | Ea, Ec, Ef, Kp, Pa |
| KP436C (11 mer) | KP425D (11 mer) | Kp | Ea, Ec, Ef, Pa, Pm |
| PA122C (15 mer) | PA107D (15 mer) | Pa | Ea, Ec, Ef, Kp, Pm* |
| EF187C (20 mer) | EF167D (20 mer) | Ef | Ea, Ec, Kp, Pa, Pm |
| EB1275C (23 mer) | EB1252C (23 mer) | Ec, Kp, Pm, Ea | Pa, Ef |
| UNI1782C (19 mer) | UNI1763D (19 mer) | Ea, Ec, Ef, Kp, Pa, Pm | None |

[a]Species abbreviations, Ec: *Escherichia coli*; Ea: *E. aerogenes*; Ef: *Enterococcus faecalis*; Pm: *Proteus mirabilis*; Kp: *Klebsiella pneumoniae*; Pa: *Pseudomonas aeruginosa*.
*Cross-reactivity with this species at a level significantly less than with the target species.

Sensor Characterization and Surface Functional Layer Preparation. Micro-fabricated electrochemical sensor arrays with an alkanethiolate self-assembled monolayer (SAM) were obtained from GeneFluidics (Monterey Park, Calif.). SAM integrity was confirmed by cyclic voltammetry (CV) (1) using a 16-channel potentiostat (GeneFluidics). After CV characterization, sensor arrays were washed and dried. Washing steps were carried out by applying a stream of deionized $H_2O$ to the sensor surface for approximately 2-3 sec followed by 5 sec of drying under a stream of nitrogen. To functionalize the sensor surface, 4 µl of 0.5 mg/ml streptavidin (Calbiochem, San Diego, Calif.) in $H_2O$ was added to the alkanethiol activated sensors, incubated for 10 min at room temperature and washed off. Biotinylated capture probes (4 µl, 1 µM in 1 M phosphate buffer, pH 7.4) were added to the streptavidin-coated sensors. 1 M phosphate buffer, pH 7.4, was prepared by mixing 1 M $NaH_2PO_4$ and 1 M $K_2HPO_4$ in a 19:81 (vol/vol) ratio, respectively, and adjusting the pH to 7.4. After 30 min of incubation at room temperature, the sensor array was washed and dried, completing the surface preparation.

Amperometric Detection of bacterial 16S rRNA. Logarithmic phase bacterial cells were concentrated by centrifugation at 10,000 rpm for 5 min. Lysis of bacterial cells was performed by addition of 10 µl of one or more of the following: 1 M NaOH; 0.1% Triton X-100 in 20 mM Tris-HCl, pH 8.0, 2 mM EDTA and 1 mg/ml lysozyme (Sigma). After incubation at room temperature, 50 µl of the detector probe (0.25 µM) in 2.5% bovine serum albumin (Sigma)—1 M phosphate buffer, pH 7.4, was added to the bacterial lysate. The detector probe/bacterial lysate mixture was incubated for 10 min at room temperature to allow hybridization of the detector probe to target rRNA. 4 µl of the bacterial lysate/detector probe mixture was deposited on each of the working electrodes in the sensor array. The sensor array was incubated for 15 min at room temperature in a humidified chamber. After washing and drying, 4 µl of 0.5 U/ml anti-fluorescein horseradish peroxidase (HRP) Fab conjugate (Roche, diluted in 0.5% casein in 1 M phosphate buffer, pH 7.4) were deposited on each of the working electrodes for 10-15 min. After washing and drying, a prefabricated plastic well manifold (GeneFluidics) was bonded to the sensor array. 50 µl of HRP substrate solution (K-Blue Enhanced K-Blue® TMB Substrate, Neogen, Lexington, Ky.) was placed on each of the sensors in the array so as to cover all three of the electrodes. Measurements were immediately and simultaneously taken for all 16 sensors. The entire assay protocol was completed within 45 min from the initiation of bacterial lysis. Amperometric current vs. time was measured using a multichannel potentiostat (GeneFluidics). The voltage was fixed at −200 mV (vs. reference), and the electroreduction current was measured at 60 sec after the HRP redox reaction reached steady state. Negative controls were included in each experiment in which detector probe mixture, pH 7.4, was used as the target instead of bacterial lysate. All samples were analyzed in duplicate.

Experiments were performed on ATCC strains to verify probe specificity using a 16-sensor array "UTI chip" in which the UNI782C, EB1275C, EC439C, KP436C, PM197C, PA122C, and EF187C. 5'-biotinylated capture probes (defined in Table 11) were tested in duplicate. The two remaining sensors in the array served as negative controls (using capture probe UNI7820 in 1 M phosphate buffer, pH 7.4, instead of bacterial lysate). Bacterial lysates were combined with a mixture of the following 3'-fluorescein labeled detector probes: UNI763D, EB1252D, EC424D, KP425D, PM176D, PA107D, and EF167D (defined in Table 11). The degree of variance in the electrochemical sensor measurements was determined by comparing duplicate measurements for all experiments. The background signal level was determined by averaging the $\log_{10}$ results of the two negative control sensors. Positive signals were defined as signals greater than five standard deviations (in $\log_{10}$ units) over background.

Results

The effect of probe hybridization location on signal intensity was examined. Experiments were performed at room temperature involving a series of 10mer capture and detector probes specific for *E. coli* helix 18. As shown in FIG. 16, probe pairs with junctions hybridizing in the helix 18 bulge between positions 432 and 439 resulted in significant current output over background. However, when the junction between probe pairs was in the double-stranded region of helix 18, little or no current output signal was detectable. These results demonstrate the importance of non-double stranded regions in accessibility to probe binding.

The effect of probe length on signal intensity was examined. Experiments were performed at room temperature involving a series of capture and detector probes, where both members of the probe pair were of equal length. In these experiments, probes ranging from 10 to 35 nucleotides in length were used, in each case the junction between probe hybridization sites was between positions 438 and 439. As shown in FIG. 17, increases in probe length resulted in increases in signal intensity until a length of 20 nucleotides was reached. Above 20 nucleotides, signal intensity was lost. Previous sensor studies had been performed with 35mer detector and capture probes using a hybridization temperature of 65° C. These results demonstrate the relationship between probe length and signal intensity, and the importance of using shorter probes for hybridization at ambient temperature. When capture probes of varying length were paired with a 13mer detector probe, a two-fold increase in signal intensity was observed for 10mer vs. 20mer capture probes (FIG. 21A). In contrast, when detector probes of varying length were paired with a 13mer capture probe, no effect on signal intensity was observed (FIG. 21B). These results demonstrate that the effect of probe length on signal intensity was primarily a function of capture probe length.

Figure 20A:
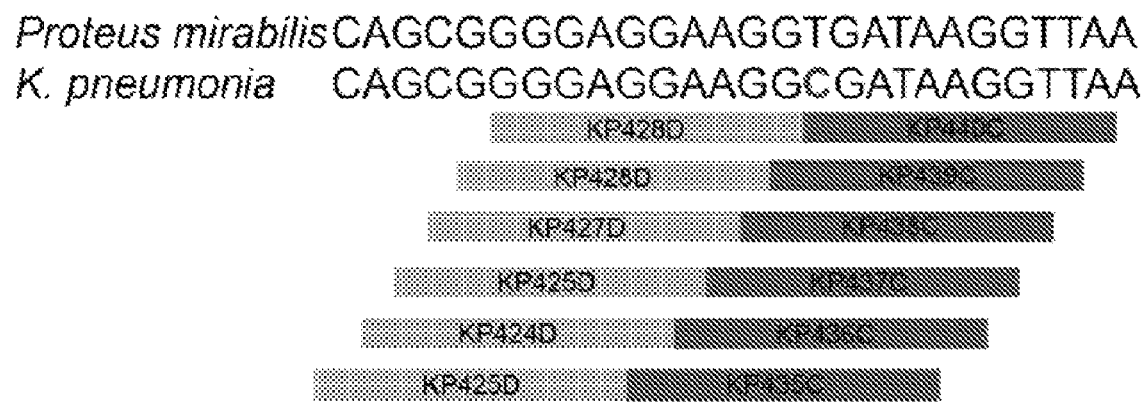
FIG. 20A. Discrimination of 16S rRNA single nucleotide polymorphism as a function of probe hybridization location. The 16S rRNA sequences of K. pneumoniae (SEQ ID NO: 169) and P. mirabilis (SEQ ID NO: 170) differ by a single nucleotide at position 440, where a Thymidine in P. mirabilis is replaced by Cytosine (bold) in K. pneumoniae.
Figures 20B, 22A, 22B:
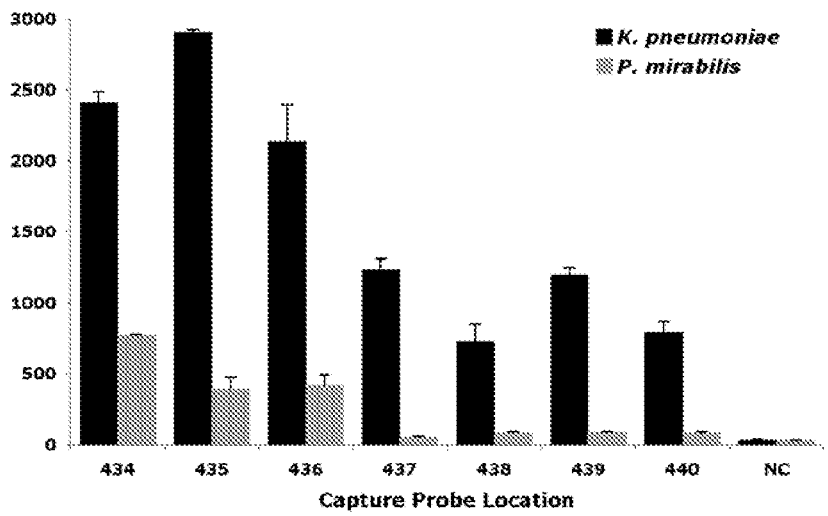
FIG. 20B. Hybridization locations of the capture and detection probes. Current output (in nanoamperes) was measured using a series of K. pneumoniae specific capture and detector probes hybridized to 16S rRNA released from K. pneumoniae and P. mirabilis. The nucleotide location at the junction of the capture and detector probe hybridization sites is shown on the horizontal axis. Mean and SD of experiments performed in duplicate are shown. Background signal was determined in negative control (NC) experiments performed with capture and detector probes but without bacterial lysate.
FIGS. 22A-B. Alignment of pathogen 16S rRNA sequences (SEQ ID NOS: 171-182). The positions of unique nucleotides (shown italicized and in lighter type) and sites of detector and capture probe hybridization are shown for P. mirabilis and E. faecalis (FIG. 22A) and K. pneumoniae and E. coli (FIG. 22B).

Specificity was affected by probe length. When probe pairs of varying length designed to hybridize to *E. coli* helix 18 were examined for specificity using a variety of bacteria, it was found that 20mer probes had significant cross-reactivity with *P. aeruginosa*. For this reason, further studies were performed with *E. coli*-specific capture and detector probes 15 nucleotides in length. Experiments involving fivefold dilutions of *E. coli* cells showed that the 15mer capture and detector probes had a sensitivity threshold of approximately 250 cells (FIG. 22). This level of detection sensitivity is similar to that of 35mer capture and detector probes using a 65° C. hybridization temperature (8).

Ambient temperature hybridization using relatively short probes was able to distinguish between organisms with nearly identical sequences. In helix 18, the *K. pneumoniae* and *P. mirabilis* 16S rRNA sequences differ by only a single nucleotide at position 440. Experiments were performed using a series of capture and detector probe pairs with hybridization site junctions near position 440. As shown in FIG. 20, the junction of the probe pairs affected signal intensity for detection of both organisms, but in each case, the signal for *K. pneumoniae* was significantly greater than for *P. mirabilis*. These results demonstrate the exquisite specificity achievable using shorter probes and ambient temperature hybridization.

A 16 sensor array was validated for hybridization at ambient temperature using a panel of well-characterized bacterial strains from the ATCC. Species specific probe pairs specific for *E. coli, K. pneumoniae, P. mirabilis, P. aeruginosa*, and *E. faecalis*. A universal bacterial probe pair and a probe pair able to detect all members of the family Enterobacteriaceae were also included in the array. As shown in FIG. 21, the sensor array allowed species-specific identification of all five target organisms. Weak cross-reactivity of the *E. coli* probes with *P. aeruginosa* 16S and of the *P. aeruginosa* probes for *P. mirabilis* 16S was easily differentiated from specific reactions by comparison of the species-specific signal with that of the universal probe. In previous studies, it had not been possible to design a probe pair able to distinguish between *Klebsiella* and *Enterobacter* species (7, 8). These results demonstrate the utility of using combinations of probe pairs in an electrochemical sensor array.

REFERENCES

1. Bard, A. J., and L. R. Faulkner. 2001. Electrochemical Methods. Fundamentals and Applications, 2nd ed. John Wiley & Sons, Inc., Hoboken, N.J.
2. Brosius, J., et al. 1978. Proc Natl Acad Sci USA 75:4801-5.
3. Erickson, K. A., and P. Wilding 1993. Clin Chem 39:283-7.
4. Fuchs, B. M., et al. 1998. Appl Environ Microbiol 64:4973-82.
5. Gau, J. J., et al. 2001. Biosens Bioelectron 16:745-55.
6. Gau, V., et al. 2005. Methods 37:73-83.
7. Liao, J. C., et al 2006. J Clin Microbiol 44:561-70.

8. Liao, J. C., et al. 2007. J Mol Diagn 9(2):158-68.
9. Newman, J. D., and A. P. Turner. 2005. Biosens Bioelectron 20:2435-53.
10. Ronkainen-Matsuno, N. J., et al. 2002. Trends Anal Chem 21:213-225.
11. Summanen, P. H., et al. 2005. J Clin Microbiol 43:4455-9.
12. Sun, C. P., et al. 2005. Mot Genet Metab 84:90-9.
13. Wang, J. 2006. Analytical Electrochemistry. J. Wiley, New York.
14. Wang. J. 2006. Biosens Bioelectron 21:1887-92.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A pair of oligonucleotide probes, the pair consisting of a capture probe and a detector probe, each of which is 10-15 bases in length, and that specifically hybridize under highly stringent conditions to adjacent regions of a target nucleic acid molecule that consists of a target capture region and a target detector region, respectively, of bacterial ribosomal RNA (rRNA), wherein the target capture region and target detector region are, or are fully complementary to, nucleic acid molecules substantially corresponding to a pair of sequences consisting of:

SEQ ID NO: 28, target capture region of E. coli, and
SEQ ID NO: 29, target detector region of E. coli
wherein the highly stringent conditions comprise hybridization and washes at 20° C. to 39° C. in 1M phosphate buffer at native pH, and wherein the probes share 100% identity or complementarity to SEQ ID NO: 28 and 29.

2. The pair of oligonucleotide probes of claim 1 that is a pair of nucleic acid sequences consisting of:

*Escherichia coli* capture probe, SEQ ID NO: 44; and detector probe, SEQ ID NO: 45.

3. The pair of oligonucleotide probes of claim 1, wherein the detector probe is labeled with a detectable marker.

4. A method for detecting the presence of E. coli in a specimen, the method comprising:

(a) contacting a lysate of the specimen with a capture probe immobilized on a substrate, wherein the capture probe comprises an oligonucleotide that specifically hybridizes with a first target nucleic acid sequence region of the pathogen, wherein the first target nucleic acid sequence region is SEQ ID NO: 28, and wherein the contacting occurs under conditions that permit hybridization of the capture probe with the first target nucleic acid sequence;

wherein the lysate is in contact with a detector probe that comprises a detectably labeled oligonucleotide that specifically hybridizes with a second target nucleic acid sequence region of the pathogen, wherein the target nucleic acid sequence region is SEQ ID NO: 29, and wherein the capture probe and detector probe are each 10-15 bases in length and share 100% identity or complementarity to SEQ ID NO: 28 and 29, respectively; and (b) determining the presence of the detector probe, whereby detection of the detector probe complexed with the substrate is indicative of the presence of E. coli in the specimen.

5. The method of claim 4, wherein the conditions that permit hybridization are a temperature of 20° C. to 39° C. and a buffered saline solution.

6. The method of claim 5, wherein the conditions that permit hybridization are a temperature of 20° C. to 25° C. and a buffered saline solution.

7. The method of claim 4, wherein the lysate is brought into contact with the detector probe prior to the contacting of the lysate with the capture probe.

8. The method of claim 4, wherein the lysate is brought into contact with the detector probe after the contacting of the lysate with the capture probe.

9. The method of claim 4, wherein the lysate is prepared by contacting the specimen with a first lysis buffer comprising a non-denaturing detergent and lysozyme.

10. The method of claim 9, wherein the lysate is further prepared by contacting the specimen with a second lysis buffer comprising NaOH.

11. The method of claim 10, wherein the contacting of the specimen with the second lysis buffer occurs prior to the contacting of the specimen with the first lysis buffer.

12. The method of claim 10, wherein the contacting of the specimen with second lysis buffer occurs after the contacting of the specimen with the first lysis buffer.

13. The method of claim 10, wherein the contacting of the specimen with the first and/or second lysis buffers occurs at 20° C. to 39° C.

14. The method of claim 10, wherein the contacting of the specimen with the first and/or second lysis buffers occurs for about 5 minutes per lysis buffer.

15. The method of claim 4, wherein the detectable label is at the 3' end of the detector probe.

16. The method of claim 4, wherein the oligonucleotide probes are 15 bases in length.

17. The method of claim 4, wherein the determining comprises an electrochemical sensor assay and the presence of detector probe is determined by measuring current output.

18. The method of claim 17, wherein the determining comprises comparing current output at 15 minutes after contacting the specimen with the growth medium.

19. The method of claim 4, wherein the specimen is a bodily fluid.

20. The method of claim 19, wherein the specimen is urine.

21. A method for detecting antibiotic susceptibility of a specimen, the method comprising:
   (a) detecting the presence of *E. coli* in the specimen according to the method of claim 4;
   (b) quantifying the *E. coli* detected in step (a);
   (c) contacting the lysate of the specimen with a capture probe immobilized on a substrate, wherein the capture probe specifically hybridizes with a first target nucleic acid sequence region of *E. coli* ribosomal RNA wherein the lysate is in contact with a detector probe that comprises a detectably labeled oligonucleotide that specifically hybridizes with a second target nucleic acid sequence region of *E. coli* ribosomal RNA; and
   (d) inoculating the specimen into a growth medium;
   (e) repeating step (d) in the presence of an antibiotic; and
   (f) comparing the amount of labeled oligonucleotide complexed with the substrate, whereby detection of less labeled oligonucleotide complexed with the substrate in the presence of antibiotic is indicative of susceptibility to the antibiotic.

22. An assay kit for detecting a plurality of pathogens comprising:
   (a) an electrochemical sensor array comprising a plurality of electrodes;
   (b) a plurality of paired oligonucleotide probes that specifically hybridize to target capture and detector nucleic acid sequence regions of bacterial ribosomal RNA, wherein a pair of the oligonucleotide probes comprises:
      (i) a capture probe bound to one of the electrodes, the capture probe having a first detectable label, wherein the target capture nucleic acid sequence region is, or is fully complementary to, nucleic acid molecules substantially corresponding to SEQ ID NO: 28; and
      (ii) a detector probe having a second detectable label, wherein the target detector nucleic acid sequence region is, or is fully complementary to, nucleic acid molecules substantially corresponding to SEQ ID NO: 29;
   wherein the capture probe and detector probes are 10-15 bases in length and specifically hybridize at 20° C. to 39° C. in 1M phosphate buffer to adjacent nucleic acid sequences of bacterial ribosomal RNA, and wherein the probes share 100% identity or complementarity to SEQ ID NO: 28 and 29.

23. The assay kit of claim 22, wherein the second detectable label is at the 3' end of the detector probe.

24. The assay kit of claim 22, wherein the oligonucleotide probes are 15 bases in length.

25. The assay kit of claim 22, wherein the bacterial ribosomal RNA is 5S, 16S or 23S ribosomal RNA.

26. The pair of oligonucleotide probes of claim 1, wherein the oligonucleotide probes are 15 bases in length.

* * * * *

UNITED STATES PATENT AND TRADEMARK OFFICE
CERTIFICATE OF CORRECTION

PATENT NO.        : 7,763,426 B2
APPLICATION NO. : 11/743071
DATED             : July 27, 2010
INVENTOR(S)       : Haake et al.

It is certified that error appears in the above-identified patent and that said Letters Patent is hereby corrected as shown below:

On the Letters Patent Title page and Col. 1, item (54) the title should read: PROBES AND METHODS FOR DETECTION OF ~~ESCHERIDIA~~ *ESCHERICHIA* COLI AND ANTIBIOTIC RESISTANCE Signed and Sealed this Twenty-eighth Day of September, 2010

David J. Kappos
*Director of the United States Patent and Trademark Office*

SEQUENCE LISTING

<160> NUMBER OF SEQ ID NOS: 182

<210> SEQ ID NO 1
<211> LENGTH: 35
<212> TYPE: DNA
<213> ORGANISM: Escherichia coli

<400> SEQUENCE: 1
gtcaatgagc aaaggtatta actttactcc cttcc        35

<210> SEQ ID NO 2
<211> LENGTH: 35
<212> TYPE: DNA
<213> ORGANISM: Escherichia coli

<400> SEQUENCE: 2
ctgaaagtac tttacaaccc gaaggccttc ttcat        35

<210> SEQ ID NO 3
<211> LENGTH: 35
<212> TYPE: DNA
<213> ORGANISM: Proteus mirabilis

<400> SEQUENCE: 3
gggttcatcc gatagtgcaa ggtccgaaga gcccc        35

<210> SEQ ID NO 4
<211> LENGTH: 35
<212> TYPE: DNA
<213> ORGANISM: Proteus mirabilis

<400> SEQUENCE: 4
ggtccgtaga cattatgcgg tattagccac cgttt        35

<210> SEQ ID NO 5
<211> LENGTH: 35
<212> TYPE: DNA
<213> ORGANISM: Enterobacter sp.

<400> SEQUENCE: 5
gtcaatcgmc raggttatta acctyahcgc cttcc        35

<210> SEQ ID NO 6
<211> LENGTH: 35
<212> TYPE: DNA
<213> ORGANISM: Enterobacter sp.

<400> SEQUENCE: 6
ctgaaagtgc tttacaaccc gaaggccttc ttcat        35

<210> SEQ ID NO 7
<211> LENGTH: 35
<212> TYPE: DNA

<213> ORGANISM: Pseudomonas aeruginosa

<400> SEQUENCE: 7
cccactttct ccctcaggac gtatgcggta ttagc                              35

<210> SEQ ID NO 8
<211> LENGTH: 35
<212> TYPE: DNA
<213> ORGANISM: Pseudomonas aeruginosa

<400> SEQUENCE: 8
ttccggacgt tatcccccac taccaggcag attcc                              35

<210> SEQ ID NO 9
<211> LENGTH: 35
<212> TYPE: DNA
<213> ORGANISM: Enterococcus sp.

<400> SEQUENCE: 9
ttggtgagcc gttacctcac caactagcta atgca                              35

<210> SEQ ID NO 10
<211> LENGTH: 35
<212> TYPE: DNA
<213> ORGANISM: Enterococcus sp.

<400> SEQUENCE: 10
gtccatccat cagcgacacc cgaaagcgcc tttca                              35

<210> SEQ ID NO 11
<211> LENGTH: 35
<212> TYPE: DNA
<213> ORGANISM: Enterobacter sp.

<400> SEQUENCE: 11
cggactacga catactttat gaggtccgct tgctc                              35

<210> SEQ ID NO 12
<211> LENGTH: 35
<212> TYPE: DNA
<213> ORGANISM: Enterobacter sp.

<400> SEQUENCE: 12
gaggtcgctt ctctttgtat atgccattgt agcac                              35

<210> SEQ ID NO 13
<211> LENGTH: 27
<212> TYPE: DNA
<213> ORGANISM: Artificial sequence
<220> FEATURE:
<223> OTHER INFORMATION: synthetic oligonucleotide probe

<400> SEQUENCE: 13
catcgtttac ggcgtggact accaggg                                       27

<210> SEQ ID NO 14
<211> LENGTH: 31
<212> TYPE: DNA
<213> ORGANISM: Artificial sequence
<220> FEATURE:
<223> OTHER INFORMATION: synthetic oligonucleotide probe

<400> SEQUENCE: 14
tatctaatcc tgtttgctcc ccacgctttc g                                  31

<210> SEQ ID NO 15
<211> LENGTH: 35
<212> TYPE: DNA
<213> ORGANISM: Escherichia coli

<400> SEQUENCE: 15
gagcaaaggt attaacttta ctcccttcct ccccg                          35

<210> SEQ ID NO 16
<211> LENGTH: 20
<212> TYPE: DNA
<213> ORGANISM: Escherichia coli

<400> SEQUENCE: 16
actttactcc cttcctcccc                                           20

<210> SEQ ID NO 17
<211> LENGTH: 35
<212> TYPE: DNA
<213> ORGANISM: Enterococcus sp.

<400> SEQUENCE: 17
ccgcgggtcc atccatcagc gacacccgaa agcgc                          35

<210> SEQ ID NO 18
<211> LENGTH: 35
<212> TYPE: DNA
<213> ORGANISM: Enterobacter sp.

<400> SEQUENCE: 18
gaggtcgctt ctctttgtat rygccattgt agcac                          35

<210> SEQ ID NO 19
<211> LENGTH: 20
<212> TYPE: DNA
<213> ORGANISM: Artificial sequence
<220> FEATURE:
<223> OTHER INFORMATION: synthetic oligonucleotide probe

<400> SEQUENCE: 19
cgtcaatgag caaaggtatt                                           20

<210> SEQ ID NO 20
<211> LENGTH: 40
<212> TYPE: DNA
<213> ORGANISM: Artificial sequence
<220> FEATURE:
<223> OTHER INFORMATION: synthetic oligonucleotide probe

<400> SEQUENCE: 20
cgtcaatgag caaaggtatt actcccttcc tccccgctga                     40

<210> SEQ ID NO 21
<211> LENGTH: 60
<212> TYPE: DNA
<213> ORGANISM: Artificial sequence
<220> FEATURE:
<223> OTHER INFORMATION: synthetic oligonucleotide probe

<400> SEQUENCE: 21
cgtcaatgag caaaggtatt actcccttcc tccccgctga cgtcaatgag caaaggtatt   60

<210> SEQ ID NO 22

```
<211> LENGTH: 21
<212> TYPE: DNA
<213> ORGANISM: Proteus mirabilis

<400> SEQUENCE: 22
cggaccttgc actatcggat g                                              21

<210> SEQ ID NO 23
<211> LENGTH: 21
<212> TYPE: DNA
<213> ORGANISM: Proteus mirabilis

<400> SEQUENCE: 23
cggaccaaag cagggctct t                                               21

<210> SEQ ID NO 24
<211> LENGTH: 20
<212> TYPE: DNA
<213> ORGANISM: Enterococcus faecalis

<400> SEQUENCE: 24
ctgatggatg gacccgcggt                                                20

<210> SEQ ID NO 25
<211> LENGTH: 20
<212> TYPE: DNA
<213> ORGANISM: Enterococcus faecalis

<400> SEQUENCE: 25
aaaggcgctt tcgggtgtcg                                                20

<210> SEQ ID NO 26
<211> LENGTH: 11
<212> TYPE: DNA
<213> ORGANISM: Klebsiella pneumoniae

<400> SEQUENCE: 26
aaggcgdtra g                                                         11

<210> SEQ ID NO 27
<211> LENGTH: 11
<212> TYPE: DNA
<213> ORGANISM: Klebsiella pneumoniae

<400> SEQUENCE: 27
cagcggggag g                                                         11

<210> SEQ ID NO 28
<211> LENGTH: 15
<212> TYPE: DNA
<213> ORGANISM: Escherichia coli

<400> SEQUENCE: 28
ggagtaaagt taata                                                     15

<210> SEQ ID NO 29
<211> LENGTH: 15
<212> TYPE: DNA
<213> ORGANISM: Escherichia coli

<400> SEQUENCE: 29
tcagcgggga ggaag                                                     15
```

```
<210> SEQ ID NO 30
<211> LENGTH: 23
<212> TYPE: DNA
<213> ORGANISM: Enterobacter sp.

<400> SEQUENCE: 30
agagcaagcg gacctcataa agt                                              23

<210> SEQ ID NO 31
<211> LENGTH: 23
<212> TYPE: DNA
<213> ORGANISM: Enterobacter sp.

<400> SEQUENCE: 31
atacaaagga aggcgacctc gcg                                              23

<210> SEQ ID NO 32
<211> LENGTH: 15
<212> TYPE: DNA
<213> ORGANISM: Pseudomonas aeruginosa

<400> SEQUENCE: 32
gagggagaaa gtggg                                                       15

<210> SEQ ID NO 33
<211> LENGTH: 15
<212> TYPE: DNA
<213> ORGANISM: Pseudomonas aeruginosa

<400> SEQUENCE: 33
taccgcatac gtcct                                                       15

<210> SEQ ID NO 34
<211> LENGTH: 16
<212> TYPE: DNA
<213> ORGANISM: Acinetobacter baumannii

<400> SEQUENCE: 34
ggagcctact ttagtt                                                      16

<210> SEQ ID NO 35
<211> LENGTH: 15
<212> TYPE: DNA
<213> ORGANISM: Acinetobacter baumannii

<400> SEQUENCE: 35
cactttaagc gagga                                                       15

<210> SEQ ID NO 36
<211> LENGTH: 22
<212> TYPE: DNA
<213> ORGANISM: Enterobacter aerogenes

<400> SEQUENCE: 36
gcgataaggt taataacctt gt                                               22

<210> SEQ ID NO 37
<211> LENGTH: 22
<212> TYPE: DNA
<213> ORGANISM: Enterobacter aerogenes

<400> SEQUENCE: 37
agtactttca gcgaggagga ag                                               22
```

```
<210> SEQ ID NO 38
<211> LENGTH: 16
<212> TYPE: DNA
<213> ORGANISM: Serratia marcescens

<400> SEQUENCE: 38
ggaaggtggt gaactt                                                    16

<210> SEQ ID NO 39
<211> LENGTH: 15
<212> TYPE: DNA
<213> ORGANISM: Serratia marcescens

<400> SEQUENCE: 39
cactttcagc gagga                                                     15

<210> SEQ ID NO 40
<211> LENGTH: 16
<212> TYPE: DNA
<213> ORGANISM: Stenotrophomonas maltophilia

<400> SEQUENCE: 40
agaaatccag ctggtt                                                    16

<210> SEQ ID NO 41
<211> LENGTH: 18
<212> TYPE: DNA
<213> ORGANISM: Stenotrophomonas maltophilia

<400> SEQUENCE: 41
aagccctttt gttgggaa                                                  18

<210> SEQ ID NO 42
<211> LENGTH: 19
<212> TYPE: DNA
<213> ORGANISM: Artificial sequence
<220> FEATURE:
<223> OTHER INFORMATION: synthetic oligonucleotide probe

<400> SEQUENCE: 42
ccctggtagt ccacgccgt                                                 19

<210> SEQ ID NO 43
<211> LENGTH: 19
<212> TYPE: DNA
<213> ORGANISM: Artificial sequence
<220> FEATURE:
<223> OTHER INFORMATION: synthetic oligonucleotide probe

<400> SEQUENCE: 43
gagcaaacag gattagata                                                 19

<210> SEQ ID NO 44
<211> LENGTH: 15
<212> TYPE: DNA
<213> ORGANISM: Escherichia coli

<400> SEQUENCE: 44
tattaacttt actcc                                                     15

<210> SEQ ID NO 45
<211> LENGTH: 15
<212> TYPE: DNA
<213> ORGANISM: Escherichia coli
```

```
<400> SEQUENCE: 45
cttcctcccc gctga                                                    15

<210> SEQ ID NO 46
<211> LENGTH: 21
<212> TYPE: DNA
<213> ORGANISM: Proteus mirabilis

<400> SEQUENCE: 46
catccgatag tgcaaggtcc g                                             21

<210> SEQ ID NO 47
<211> LENGTH: 21
<212> TYPE: DNA
<213> ORGANISM: Proteus mirabilis

<400> SEQUENCE: 47
aagagcccct gctttggtcc g                                             21

<210> SEQ ID NO 48
<211> LENGTH: 11
<212> TYPE: DNA
<213> ORGANISM: Klebsiella pneumoniae

<400> SEQUENCE: 48
ctyahcgcct t                                                        11

<210> SEQ ID NO 49
<211> LENGTH: 11
<212> TYPE: DNA
<213> ORGANISM: Klebsiella pneumoniae

<400> SEQUENCE: 49
cctccccgct g                                                        11

<210> SEQ ID NO 50
<211> LENGTH: 15
<212> TYPE: DNA
<213> ORGANISM: Pseudomonas aeruginosa

<400> SEQUENCE: 50
cccactttct ccctc                                                    15

<210> SEQ ID NO 51
<211> LENGTH: 15
<212> TYPE: DNA
<213> ORGANISM: Pseudomonas aeruginosa

<400> SEQUENCE: 51
aggacgtatg cggta                                                    15

<210> SEQ ID NO 52
<211> LENGTH: 20
<212> TYPE: DNA
<213> ORGANISM: Enterococcus sp.

<400> SEQUENCE: 52
accgcgggtc catccatcag                                               20

<210> SEQ ID NO 53
<211> LENGTH: 20
<212> TYPE: DNA
```

<213> ORGANISM: Enterococcus sp.

<400> SEQUENCE: 53
cgacacccga aagcgccttt                                                   20

<210> SEQ ID NO 54
<211> LENGTH: 23
<212> TYPE: DNA
<213> ORGANISM: Enterobacter sp.

<400> SEQUENCE: 54
actttatgag gtccgcttgc tct                                               23

<210> SEQ ID NO 55
<211> LENGTH: 23
<212> TYPE: DNA
<213> ORGANISM: Enterobacter sp.

<400> SEQUENCE: 55
cgcgaggtcg ccttcctttg tat                                               23

<210> SEQ ID NO 56
<211> LENGTH: 16
<212> TYPE: DNA
<213> ORGANISM: Acinetobacter baumannii

<400> SEQUENCE: 56
aactaaagta ggctcc                                                       16

<210> SEQ ID NO 57
<211> LENGTH: 15
<212> TYPE: DNA
<213> ORGANISM: Acinetobacter baumannii

<400> SEQUENCE: 57
tcctcgctta aagtg                                                        15

<210> SEQ ID NO 58
<211> LENGTH: 22
<212> TYPE: DNA
<213> ORGANISM: Enterobacter aerogenes

<400> SEQUENCE: 58
acaaggttat taaccttatc gc                                                22

<210> SEQ ID NO 59
<211> LENGTH: 22
<212> TYPE: DNA
<213> ORGANISM: Enterobacter aerogenes

<400> SEQUENCE: 59
cttcctcctc gctgaaagta ct                                                22

<210> SEQ ID NO 60
<211> LENGTH: 16
<212> TYPE: DNA
<213> ORGANISM: Serratia marcescens

<400> SEQUENCE: 60
aagttcacca ccttcc                                                       16

<210> SEQ ID NO 61
<211> LENGTH: 15

<212> TYPE: DNA
<213> ORGANISM: Serratia marcescens

<400> SEQUENCE: 61
gtgaaagtcg ctcct                                                    15

<210> SEQ ID NO 62
<211> LENGTH: 16
<212> TYPE: DNA
<213> ORGANISM: Stenotrophomonas maltophilia

<400> SEQUENCE: 62
aaccagctgg atttct                                                   16

<210> SEQ ID NO 63
<211> LENGTH: 18
<212> TYPE: DNA
<213> ORGANISM: Stenotrophomonas maltophilia

<400> SEQUENCE: 63
ttcccaacaa aagggctt                                                 18

<210> SEQ ID NO 64
<211> LENGTH: 19
<212> TYPE: DNA
<213> ORGANISM: Artificial sequence
<220> FEATURE:
<223> OTHER INFORMATION: synthetic oligonucleotide probe

<400> SEQUENCE: 64
acggcgtgga ctaccaggg                                                19

<210> SEQ ID NO 65
<211> LENGTH: 19
<212> TYPE: DNA
<213> ORGANISM: Artificial sequence
<220> FEATURE:
<223> OTHER INFORMATION: synthetic oligonucleotide probe

<400> SEQUENCE: 65
tatctaatcc tgtttgctc                                                19

<210> SEQ ID NO 66
<211> LENGTH: 35
<212> TYPE: DNA
<213> ORGANISM: Enterobacter sp.

<400> SEQUENCE: 66
cggactacga cryactttat gaggtccgct tgctc                              35

<210> SEQ ID NO 67
<211> LENGTH: 35
<212> TYPE: DNA
<213> ORGANISM: Escherichia coli

<400> SEQUENCE: 67
gtcaatgagc aaaggtatta actttactcc cttcc                              35

<210> SEQ ID NO 68
<211> LENGTH: 35
<212> TYPE: DNA
<213> ORGANISM: Escherichia coli

<400> SEQUENCE: 68

-continued gagcaaaggt attaacttta ctcccttcct ccccg                              35

<210> SEQ ID NO 69
<211> LENGTH: 35
<212> TYPE: DNA
<213> ORGANISM: Enterococcus sp.

<400> SEQUENCE: 69
ttggtgagcc gttacctcac caactagcta atgca                              35

<210> SEQ ID NO 70
<211> LENGTH: 35
<212> TYPE: DNA
<213> ORGANISM: Enterococcus sp.

<400> SEQUENCE: 70
gtccatccat cagcgacacc cgaaagcgcc tttca                              35

<210> SEQ ID NO 71
<211> LENGTH: 35
<212> TYPE: DNA
<213> ORGANISM: Klebsiella pneumoniae

<400> SEQUENCE: 71
gtcaatcgmc raggttatta acctyahcgc cttcc                              35

<210> SEQ ID NO 72
<211> LENGTH: 35
<212> TYPE: DNA
<213> ORGANISM: Pseudomonas aeruginosa

<400> SEQUENCE: 72
cccactttct ccctcaggac gtatgcggta ttagc                              35

<210> SEQ ID NO 73
<211> LENGTH: 35
<212> TYPE: DNA
<213> ORGANISM: Pseudomonas aeruginosa

<400> SEQUENCE: 73
tgagttcccg aaggcaccaa tccatctctg gaaag                              35

<210> SEQ ID NO 74
<211> LENGTH: 35
<212> TYPE: DNA
<213> ORGANISM: Proteus mirabilis

<400> SEQUENCE: 74
gggttcatcc gatagtgcaa ggtccgaaga gcccc                              35

<210> SEQ ID NO 75
<211> LENGTH: 27
<212> TYPE: DNA
<213> ORGANISM: Artificial sequence
<220> FEATURE:
<223> OTHER INFORMATION: synthetic oligonucleotide probe

<400> SEQUENCE: 75
catcgtttac ggcgtggact accaggg                                       27

<210> SEQ ID NO 76
<211> LENGTH: 35
<212> TYPE: DNA
<213> ORGANISM: Enterobacter sp.

<400> SEQUENCE: 76
gaggtcgctt ctctttgtat rygccattgt agcac　　　　　　　　　　　　　　　35

<210> SEQ ID NO 77
<211> LENGTH: 35
<212> TYPE: DNA
<213> ORGANISM: Enterobacter sp.

<400> SEQUENCE: 77
tcgcgaggtc gcttctcttt gtatrygcca ttgta　　　　　　　　　　　　　　　35

<210> SEQ ID NO 78
<211> LENGTH: 35
<212> TYPE: DNA
<213> ORGANISM: Escherichia coli

<400> SEQUENCE: 78
ctgaaagtac tttacaaccc gaaggccttc ttcat　　　　　　　　　　　　　　　35

<210> SEQ ID NO 79
<211> LENGTH: 35
<212> TYPE: DNA
<213> ORGANISM: Escherichia coli

<400> SEQUENCE: 79
gctgaaagta ctttacaacc cgaaggcctt cttca　　　　　　　　　　　　　　　35

<210> SEQ ID NO 80
<211> LENGTH: 35
<212> TYPE: DNA
<213> ORGANISM: Escherichia coli

<400> SEQUENCE: 80
cgctgaaagt actttacaac ccgaaggcct tcttc　　　　　　　　　　　　　　　35

<210> SEQ ID NO 81
<211> LENGTH: 35
<212> TYPE: DNA
<213> ORGANISM: Escherichia coli

<400> SEQUENCE: 81
ccgctgaaag tactttacaa cccgaaggcc ttctt　　　　　　　　　　　　　　　35

<210> SEQ ID NO 82
<211> LENGTH: 35
<212> TYPE: DNA
<213> ORGANISM: Escherichia coli

<400> SEQUENCE: 82
cccgctgaaa gtactttaca acccgaaggc cttct　　　　　　　　　　　　　　　35

<210> SEQ ID NO 83
<211> LENGTH: 35
<212> TYPE: DNA
<213> ORGANISM: Escherichia coli

<400> SEQUENCE: 83
ccccgctgaa agtactttac aacccgaagg ccttc　　　　　　　　　　　　　　　35

<210> SEQ ID NO 84
<211> LENGTH: 35
<212> TYPE: DNA

<213> ORGANISM: Escherichia coli

<400> SEQUENCE: 84
tccccgctga aagtacttta aacccgaag gcctt　　　　　　　　　　　　　35

<210> SEQ ID NO 85
<211> LENGTH: 35
<212> TYPE: DNA
<213> ORGANISM: Enterococcus sp.

<400> SEQUENCE: 85
gtccatccat cagcgacacc cgaaagcgcc tttca　　　　　　　　　　　　　35

<210> SEQ ID NO 86
<211> LENGTH: 35
<212> TYPE: DNA
<213> ORGANISM: Enterococcus sp.

<400> SEQUENCE: 86
ccgcgggtcc atccatcagc gacacccgaa agcgc　　　　　　　　　　　　　35

<210> SEQ ID NO 87
<211> LENGTH: 35
<212> TYPE: DNA
<213> ORGANISM: Enterococcus sp.

<400> SEQUENCE: 87
ttggtgagcc gttacctcac caactagcta atgca　　　　　　　　　　　　　35

<210> SEQ ID NO 88
<211> LENGTH: 35
<212> TYPE: DNA
<213> ORGANISM: Klebsiella-Enterobacter Group

<400> SEQUENCE: 88
ctgaaagtgc tttacaaccc gaaggccttc ttcat　　　　　　　　　　　　　35

<210> SEQ ID NO 89
<211> LENGTH: 35
<212> TYPE: DNA
<213> ORGANISM: Klebsiella-Enterobacter Group

<400> SEQUENCE: 89
tccccgctga aagtgcttta aacccgaag gcctt　　　　　　　　　　　　　35

<210> SEQ ID NO 90
<211> LENGTH: 35
<212> TYPE: DNA
<213> ORGANISM: Pseudomonas aeruginosa

<400> SEQUENCE: 90
ttccggacgt tatccccccac taccaggcag attcc　　　　　　　　　　　　　35

<210> SEQ ID NO 91
<211> LENGTH: 35
<212> TYPE: DNA
<213> ORGANISM: Pseudomonas aeruginosa

<400> SEQUENCE: 91
gcccgtttcc ggacgttatc ccccactacc aggca　　　　　　　　　　　　　35

<210> SEQ ID NO 92
<211> LENGTH: 35

```
<212> TYPE: DNA
<213> ORGANISM: Pseudomonas aeruginosa

<400> SEQUENCE: 92
cagcatgtca aggccaggta aggttcttcg cgttg                          35

<210> SEQ ID NO 93
<211> LENGTH: 35
<212> TYPE: DNA
<213> ORGANISM: Proteus mirabilis

<400> SEQUENCE: 93
ggtccgtaga cattatgcgg tattagccac cgttt                          35

<210> SEQ ID NO 94
<211> LENGTH: 35
<212> TYPE: DNA
<213> ORGANISM: Proteus mirabilis

<400> SEQUENCE: 94
tgctttggtc cgtagacatt atgcggtatt agcca                          35

<210> SEQ ID NO 95
<211> LENGTH: 31
<212> TYPE: DNA
<213> ORGANISM: Artificial sequence
<220> FEATURE:
<223> OTHER INFORMATION: synthetic oligonucleotide probe

<400> SEQUENCE: 95
tatctaatcc tgtttgctcc ccacgctttc g                              31

<210> SEQ ID NO 96
<211> LENGTH: 10
<212> TYPE: DNA
<213> ORGANISM: Escherichia coli

<400> SEQUENCE: 96
tactcccttc                                                      10

<210> SEQ ID NO 97
<211> LENGTH: 10
<212> TYPE: DNA
<213> ORGANISM: Escherichia coli

<400> SEQUENCE: 97
ctccccgctg                                                      10

<210> SEQ ID NO 98
<211> LENGTH: 10
<212> TYPE: DNA
<213> ORGANISM: Escherichia coli

<400> SEQUENCE: 98
ttactccctt                                                      10

<210> SEQ ID NO 99
<211> LENGTH: 10
<212> TYPE: DNA
<213> ORGANISM: Escherichia coli

<400> SEQUENCE: 99
cctccccgct                                                      10
```

```
<210> SEQ ID NO 100
<211> LENGTH: 10
<212> TYPE: DNA
<213> ORGANISM: Escherichia coli

<400> SEQUENCE: 100
tttactccct                                                                 10

<210> SEQ ID NO 101
<211> LENGTH: 10
<212> TYPE: DNA
<213> ORGANISM: Escherichia coli

<400> SEQUENCE: 101
tcctccccgc                                                                 10

<210> SEQ ID NO 102
<211> LENGTH: 10
<212> TYPE: DNA
<213> ORGANISM: Escherichia coli

<400> SEQUENCE: 102
ctttactccc                                                                 10

<210> SEQ ID NO 103
<211> LENGTH: 10
<212> TYPE: DNA
<213> ORGANISM: Escherichia coli

<400> SEQUENCE: 103
ttcctccccg                                                                 10

<210> SEQ ID NO 104
<211> LENGTH: 10
<212> TYPE: DNA
<213> ORGANISM: Escherichia coli

<400> SEQUENCE: 104
actttactcc                                                                 10

<210> SEQ ID NO 105
<211> LENGTH: 10
<212> TYPE: DNA
<213> ORGANISM: Escherichia coli

<400> SEQUENCE: 105
cttcctcccc                                                                 10

<210> SEQ ID NO 106
<211> LENGTH: 10
<212> TYPE: DNA
<213> ORGANISM: Escherichia coli

<400> SEQUENCE: 106
aactttactc                                                                 10

<210> SEQ ID NO 107
<211> LENGTH: 10
<212> TYPE: DNA
<213> ORGANISM: Escherichia coli

<400> SEQUENCE: 107
ccttcctccc                                                                 10
```

<210> SEQ ID NO 108
<211> LENGTH: 10
<212> TYPE: DNA
<213> ORGANISM: Escherichia coli

<400> SEQUENCE: 108
taactttact                                                          10

<210> SEQ ID NO 109
<211> LENGTH: 10
<212> TYPE: DNA
<213> ORGANISM: Escherichia coli

<400> SEQUENCE: 109
cccttcctcc                                                          10

<210> SEQ ID NO 110
<211> LENGTH: 10
<212> TYPE: DNA
<213> ORGANISM: Escherichia coli

<400> SEQUENCE: 110
ttaactttac                                                          10

<210> SEQ ID NO 111
<211> LENGTH: 10
<212> TYPE: DNA
<213> ORGANISM: Escherichia coli

<400> SEQUENCE: 111
tcccttcctc                                                          10

<210> SEQ ID NO 112
<211> LENGTH: 10
<212> TYPE: DNA
<213> ORGANISM: Escherichia coli

<400> SEQUENCE: 112
attaacttta                                                          10

<210> SEQ ID NO 113
<211> LENGTH: 10
<212> TYPE: DNA
<213> ORGANISM: Escherichia coli

<400> SEQUENCE: 113
ctcccttcct                                                          10

<210> SEQ ID NO 114
<211> LENGTH: 10
<212> TYPE: DNA
<213> ORGANISM: Escherichia coli

<400> SEQUENCE: 114
tattaacttt                                                          10

<210> SEQ ID NO 115
<211> LENGTH: 10
<212> TYPE: DNA
<213> ORGANISM: Escherichia coli

<400> SEQUENCE: 115

-continued

```
actcccttcc                                                          10

<210> SEQ ID NO 116
<211> LENGTH: 11
<212> TYPE: DNA
<213> ORGANISM: Escherichia coli

<400> SEQUENCE: 116
aactttactc c                                                        11

<210> SEQ ID NO 117
<211> LENGTH: 11
<212> TYPE: DNA
<213> ORGANISM: Escherichia coli

<400> SEQUENCE: 117
cttcctcccc g                                                        11

<210> SEQ ID NO 118
<211> LENGTH: 12
<212> TYPE: DNA
<213> ORGANISM: Escherichia coli

<400> SEQUENCE: 118
taactttact cc                                                       12

<210> SEQ ID NO 119
<211> LENGTH: 12
<212> TYPE: DNA
<213> ORGANISM: Escherichia coli

<400> SEQUENCE: 119
cttcctcccc gc                                                       12

<210> SEQ ID NO 120
<211> LENGTH: 13
<212> TYPE: DNA
<213> ORGANISM: Escherichia coli

<400> SEQUENCE: 120
ttaactttac tcc                                                      13

<210> SEQ ID NO 121
<211> LENGTH: 13
<212> TYPE: DNA
<213> ORGANISM: Escherichia coli

<400> SEQUENCE: 121
cttcctcccc gct                                                      13

<210> SEQ ID NO 122
<211> LENGTH: 14
<212> TYPE: DNA
<213> ORGANISM: Escherichia coli

<400> SEQUENCE: 122
attaacttta ctcc                                                     14

<210> SEQ ID NO 123
<211> LENGTH: 14
<212> TYPE: DNA
<213> ORGANISM: Escherichia coli

<400> SEQUENCE: 123
```
cttcctcccc gctg                                                           14

<210> SEQ ID NO 124
<211> LENGTH: 20
<212> TYPE: DNA
<213> ORGANISM: Escherichia coli

<400> SEQUENCE: 124
aaaggtatta actttactcc                                                     20

<210> SEQ ID NO 125
<211> LENGTH: 20
<212> TYPE: DNA
<213> ORGANISM: Escherichia coli

<400> SEQUENCE: 125
cttcctcccc gctgaaagta                                                     20

<210> SEQ ID NO 126
<211> LENGTH: 25
<212> TYPE: DNA
<213> ORGANISM: Escherichia coli

<400> SEQUENCE: 126
tgagcaaagg tattaacttt actcc                                               25

<210> SEQ ID NO 127
<211> LENGTH: 25
<212> TYPE: DNA
<213> ORGANISM: Escherichia coli

<400> SEQUENCE: 127
cttccctgaa agtactttac aaccc                                               25

<210> SEQ ID NO 128
<211> LENGTH: 30
<212> TYPE: DNA
<213> ORGANISM: Escherichia coli

<400> SEQUENCE: 128
gtcaatgagc aaaggtatta actttactcc                                          30

<210> SEQ ID NO 129
<211> LENGTH: 30
<212> TYPE: DNA
<213> ORGANISM: Escherichia coli

<400> SEQUENCE: 129
cttccctgaa agtactttac aacccgaagg                                          30

<210> SEQ ID NO 130
<211> LENGTH: 35
<212> TYPE: DNA
<213> ORGANISM: Escherichia coli

<400> SEQUENCE: 130
tgagcgtcaa tgagcaaagg tattaacttt actcc                                    35

<210> SEQ ID NO 131
<211> LENGTH: 35
<212> TYPE: DNA
<213> ORGANISM: Escherichia coli

```
<400> SEQUENCE: 131
cttccctgaa agtactttac aacccgaagg ccttc                                35

<210> SEQ ID NO 132
<211> LENGTH: 12
<212> TYPE: DNA
<213> ORGANISM: Proteus mirabilis

<400> SEQUENCE: 132
ttatcacctt cc                                                         12

<210> SEQ ID NO 133
<211> LENGTH: 12
<212> TYPE: DNA
<213> ORGANISM: Proteus mirabilis

<400> SEQUENCE: 133
tccccgctga aa                                                         12

<210> SEQ ID NO 134
<211> LENGTH: 12
<212> TYPE: DNA
<213> ORGANISM: Proteus mirabilis

<400> SEQUENCE: 134
cttatcacct tc                                                         12

<210> SEQ ID NO 135
<211> LENGTH: 12
<212> TYPE: DNA
<213> ORGANISM: Proteus mirabilis

<400> SEQUENCE: 135
ctccccgctg aa                                                         12

<210> SEQ ID NO 136
<211> LENGTH: 12
<212> TYPE: DNA
<213> ORGANISM: Proteus mirabilis

<400> SEQUENCE: 136
ccttatcacc tt                                                         12

<210> SEQ ID NO 137
<211> LENGTH: 12
<212> TYPE: DNA
<213> ORGANISM: Proteus mirabilis

<400> SEQUENCE: 137
cctccccgct ga                                                         12

<210> SEQ ID NO 138
<211> LENGTH: 11
<212> TYPE: DNA
<213> ORGANISM: Proteus mirabilis

<400> SEQUENCE: 138
ccttatcacc t                                                          11

<210> SEQ ID NO 139
<211> LENGTH: 11
<212> TYPE: DNA
<213> ORGANISM: Proteus mirabilis
```

<400> SEQUENCE: 139
tcctccccgc t                                                           11

<210> SEQ ID NO 140
<211> LENGTH: 12
<212> TYPE: DNA
<213> ORGANISM: Proteus mirabilis

<400> SEQUENCE: 140
aaccttatca cc                                                          12

<210> SEQ ID NO 141
<211> LENGTH: 12
<212> TYPE: DNA
<213> ORGANISM: Proteus mirabilis

<400> SEQUENCE: 141
ttcctccccg ct                                                          12

<210> SEQ ID NO 142
<211> LENGTH: 13
<212> TYPE: DNA
<213> ORGANISM: Proteus mirabilis

<400> SEQUENCE: 142
ttaaccttat cac                                                         13

<210> SEQ ID NO 143
<211> LENGTH: 13
<212> TYPE: DNA
<213> ORGANISM: Proteus mirabilis

<400> SEQUENCE: 143
cttcctcccc gct                                                         13

<210> SEQ ID NO 144
<211> LENGTH: 13
<212> TYPE: DNA
<213> ORGANISM: Proteus mirabilis

<400> SEQUENCE: 144
attaacctta tca                                                         13

<210> SEQ ID NO 145
<211> LENGTH: 13
<212> TYPE: DNA
<213> ORGANISM: Proteus mirabilis

<400> SEQUENCE: 145
ccttcctccc cgc                                                         13

<210> SEQ ID NO 146
<211> LENGTH: 11
<212> TYPE: DNA
<213> ORGANISM: Klebsiella pneumoniae

<400> SEQUENCE: 146
tyahcgcctt c                                                           11

<210> SEQ ID NO 147
<211> LENGTH: 11
<212> TYPE: DNA

<213> ORGANISM: Klebsiella pneumoniae

<400> SEQUENCE: 147
ctccccgctg a                                                            11

<210> SEQ ID NO 148
<211> LENGTH: 10
<212> TYPE: DNA
<213> ORGANISM: Klebsiella pneumoniae

<400> SEQUENCE: 148 ctyahcgcct                                                              10

<210> SEQ ID NO 149
<211> LENGTH: 10
<212> TYPE: DNA
<213> ORGANISM: Klebsiella pneumoniae

<400> SEQUENCE: 149
tcctccccgc                                                              10

<210> SEQ ID NO 150
<211> LENGTH: 10
<212> TYPE: DNA
<213> ORGANISM: Klebsiella pneumoniae

<400> SEQUENCE: 150 cctyahcgcc                                                              10

<210> SEQ ID NO 151
<211> LENGTH: 10
<212> TYPE: DNA
<213> ORGANISM: Klebsiella pneumoniae

<400> SEQUENCE: 151
ttcctccccg                                                              10

<210> SEQ ID NO 152
<211> LENGTH: 11
<212> TYPE: DNA
<213> ORGANISM: Klebsiella pneumoniae

<400> SEQUENCE: 152
aacctyahcg c                                                            11

<210> SEQ ID NO 153
<211> LENGTH: 11
<212> TYPE: DNA
<213> ORGANISM: Klebsiella pneumoniae

<400> SEQUENCE: 153
cttcctcccc g                                                            11

<210> SEQ ID NO 154
<211> LENGTH: 12
<212> TYPE: DNA
<213> ORGANISM: Klebsiella pneumoniae

<400> SEQUENCE: 154
ttaacctyah cg                                                           12

<210> SEQ ID NO 155
<211> LENGTH: 12

```
<212> TYPE: DNA
<213> ORGANISM: Klebsiella pneumoniae

<400> SEQUENCE: 155
ccttcctccc cg                                                        12

<210> SEQ ID NO 156
<211> LENGTH: 11
<212> TYPE: DNA
<213> ORGANISM: Pseudomonas aeruginosa

<400> SEQUENCE: 156
ctttctccct c                                                         11

<210> SEQ ID NO 157
<211> LENGTH: 11
<212> TYPE: DNA
<213> ORGANISM: Pseudomonas aeruginosa

<400> SEQUENCE: 157
aggacgtatg c                                                         11

<210> SEQ ID NO 158
<211> LENGTH: 12
<212> TYPE: DNA
<213> ORGANISM: Pseudomonas aeruginosa

<400> SEQUENCE: 158
actttctccc tc                                                        12

<210> SEQ ID NO 159
<211> LENGTH: 12
<212> TYPE: DNA
<213> ORGANISM: Pseudomonas aeruginosa

<400> SEQUENCE: 159
aggacgtatg cg                                                        12

<210> SEQ ID NO 160
<211> LENGTH: 13
<212> TYPE: DNA
<213> ORGANISM: Pseudomonas aeruginosa

<400> SEQUENCE: 160
cactttctcc ctc                                                       13

<210> SEQ ID NO 161
<211> LENGTH: 13
<212> TYPE: DNA
<213> ORGANISM: Pseudomonas aeruginosa

<400> SEQUENCE: 161
aggacgtatg cgg                                                       13

<210> SEQ ID NO 162
<211> LENGTH: 20
<212> TYPE: DNA
<213> ORGANISM: Pseudomonas aeruginosa

<400> SEQUENCE: 162 gatccccac tttctccctc                                                 20

<210> SEQ ID NO 163
```

```
<211> LENGTH: 20
<212> TYPE: DNA
<213> ORGANISM: Pseudomonas aeruginosa

<400> SEQUENCE: 163
aggacgtatg cggtattagc                                              20

<210> SEQ ID NO 164
<211> LENGTH: 15
<212> TYPE: DNA
<213> ORGANISM: Pseudomonas aeruginosa

<400> SEQUENCE: 164
gccactaaga tctca                                                   15

<210> SEQ ID NO 165
<211> LENGTH: 15
<212> TYPE: DNA
<213> ORGANISM: Pseudomonas aeruginosa

<400> SEQUENCE: 165
aggatcccaa cggct                                                   15

<210> SEQ ID NO 166
<211> LENGTH: 20
<212> TYPE: DNA
<213> ORGANISM: Pseudomonas aeruginosa

<400> SEQUENCE: 166
gctgcgccac taagatctca                                              20

<210> SEQ ID NO 167
<211> LENGTH: 20
<212> TYPE: DNA
<213> ORGANISM: Pseudomonas aeruginosa

<400> SEQUENCE: 167
aggatcccaa cggctagtcg                                              20

<210> SEQ ID NO 168
<211> LENGTH: 61
<212> TYPE: RNA
<213> ORGANISM: Escherichia coli

<400> SEQUENCE: 168
guucagcggg gaggaaggga guaaaguuaa uaccuuugcu cauugacguu acccgcagaa  60
c                                                                  61

<210> SEQ ID NO 169
<211> LENGTH: 27
<212> TYPE: DNA
<213> ORGANISM: Proteus mirabilis

<400> SEQUENCE: 169
cagcggggag gaaggtgata aggttaa                                      27

<210> SEQ ID NO 170
<211> LENGTH: 27
<212> TYPE: DNA
<213> ORGANISM: Klebsiella pneumoniae

<400> SEQUENCE: 170
cagcggggag gaaggcgata aggttaa                                      27
```

<210> SEQ ID NO 171
<211> LENGTH: 54
<212> TYPE: DNA
<213> ORGANISM: Pseudomonas aeruginosa

<400> SEQUENCE: 171
gagggagaaa gtgggggatc ttcggacctc acgctatcag atgagcctag gtcg        54

<210> SEQ ID NO 172
<211> LENGTH: 54
<212> TYPE: DNA
<213> ORGANISM: Enterobacter aerogenes

<400> SEQUENCE: 172
caagaccaaa gtgggggacc ttcgggcctc atgccatcag atgtgcccag atgg        54

<210> SEQ ID NO 173
<211> LENGTH: 54
<212> TYPE: DNA
<213> ORGANISM: Klebsiella pneumoniae

<400> SEQUENCE: 173
caagaccaaa gtgggggacc ttcgggcctc atgccatcag atgtgcccag atgg        54

<210> SEQ ID NO 174
<211> LENGTH: 54
<212> TYPE: DNA
<213> ORGANISM: Proteus mirabilis

<400> SEQUENCE: 174
acggaccaaa gcagggctc ttcggaccttgcactatcgg atgaacccat atgg        54

<210> SEQ ID NO 175
<211> LENGTH: 54
<212> TYPE: DNA
<213> ORGANISM: Escherichia coli

<400> SEQUENCE: 175
caagaccaaa gaggggacc ttcgggcctc ttgccatcgg atgtgccag atgg        54

<210> SEQ ID NO 176
<211> LENGTH: 56
<212> TYPE: DNA
<213> ORGANISM: Enterococcus faecalis

<400> SEQUENCE: 176
catggcataa gagtgaaagg cgctttcggg tgtcgctgat ggatggaccc gcggtg      56

<210> SEQ ID NO 177
<211> LENGTH: 46
<212> TYPE: DNA
<213> ORGANISM: Pseudomonas aeruginosa

<400> SEQUENCE: 177
aagtactttc agcgaggagg aaggcgttaa ggttaataac cttgtc                 46

<210> SEQ ID NO 178
<211> LENGTH: 46
<212> TYPE: DNA
<213> ORGANISM: Enterobacter aerogenes

<400> SEQUENCE: 178

```
aagtactttc agcgaggagg aaggcgttaa ggttaataac cttgtc                46

<210> SEQ ID NO 179
<211> LENGTH: 46
<212> TYPE: DNA
<213> ORGANISM: Klebsiella pneumoniae

<400> SEQUENCE: 179
aagcactttc agcggggagg aaggcgataa ggttaataac ctyrtc                46

<210> SEQ ID NO 180
<211> LENGTH: 46
<212> TYPE: DNA
<213> ORGANISM: Proteus mirabilis

<400> SEQUENCE: 180
aagtactttc agcggggagg aaggtgataa ggttaatacc cttatc                46

<210> SEQ ID NO 181
<211> LENGTH: 46
<212> TYPE: DNA
<213> ORGANISM: Escherichia coli

<400> SEQUENCE: 181
aagtactttc agcggggagg aagggagtaa agttaatacc tttgct                46

<210> SEQ ID NO 182
<211> LENGTH: 46
<212> TYPE: DNA
<213> ORGANISM: Enterococcus faecalis

<400> SEQUENCE: 182
aaactctgtt gttagagaag aacaaggacg ttagtaactg aacgtc                46
```